US010377821B2

(12) United States Patent
Pannequin et al.

(10) Patent No.: US 10,377,821 B2
(45) **Date of Patent: *Aug. 13, 2019**

(54) MONOCLONAL ANTIBODIES TO PROGASTRIN AND THEIR USES

(71) Applicants: LES LABORATOIRES SERVIER, Suresnes (FR); INSTITUT NATIONAL DE LA SANTÉ DE LA RECHERCHE MÉDICALE (INSERM), Paris (FR); CENTRE NATIONAL DE LA RECHERCHE SCIENTIFIQUE (CNRS), Paris (FR)

(72) Inventors: Julie Pannequin, Sète (FR); Laure Boudier, Saint-Yorre (FR); Dominique Joubert, Sète (FR); Frédéric Hollande, Les Matelles (FR)

(73) Assignees: Les Laboratoires Servier, Suresnes (FR); Institut National de la Santé et de la Recherche Médicale (INSERM), Paris (FR); Centre National de la Recherche Scientifique (CNRS), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/451,275

(22) Filed: Mar. 6, 2017

(65) Prior Publication Data

US 2017/0306012 A1 Oct. 26, 2017

Related U.S. Application Data

(62) Division of application No. 12/906,041, filed on Oct. 15, 2010, now Pat. No. 9,611,320.

(60) Provisional application No. 61/252,625, filed on Oct. 16, 2009.

(51) Int. Cl.
*A61K 39/00* (2006.01)
*C07K 16/26* (2006.01)
*G01N 33/574* (2006.01)

(52) U.S. Cl.
CPC ....... *C07K 16/26* (2013.01); *G01N 33/57419* (2013.01); *G01N 33/57488* (2013.01); *A61K 2039/505* (2013.01); *C07K 2317/24* (2013.01); *C07K 2317/33* (2013.01); *C07K 2317/34* (2013.01); *C07K 2317/565* (2013.01); *C07K 2317/567* (2013.01); *C07K 2317/73* (2013.01); *C07K 2317/76* (2013.01); *C07K 2317/92* (2013.01); *G01N 2333/595* (2013.01)

(58) Field of Classification Search
CPC ............................................... A61K 2039/505
See application file for complete search history.

(56) References Cited

U.S. PATENT DOCUMENTS

| | | | |
|---|---|---|---|
| 7,854,932 | B2 | 12/2010 | Singh |
| 2011/0318380 | A1 | 12/2011 | Brix |

FOREIGN PATENT DOCUMENTS

| | | | | |
|---|---|---|---|---|
| WO | WO 2006/032980 | A1 | 3/2006 | |
| WO | WO 2008/076454 | A1 | 6/2006 | |
| WO | WO 2007/135542 | A2 | 11/2007 | |

OTHER PUBLICATIONS

Horbach et al. (PLoS One. Oct. 12, 2017; 12 (10): e0186281; pp. 1-16).*
Chatterjee (Science. Feb. 16, 2007; 315 (5814): 928-31).*
Esquenet et al. (J. Steroid Biochem. Mol. Biol. Aug. 1997; 62 (5-6): 391-9).*
Napier et al. (J. Biol. Chem. Feb. 9, 2007; 282 (6): 3433-41).*
Baldwin et al., 1998 "Gastrin, gastrin receptors and colorectal carcinoma," *Gut* 42:581-584.
Barderas et al., 2008 "Designing antibodies for the inhibition of gastrin activity in tumoral cell lines," *Int J Cancer* 122(10):2351-2359.
Caldas et al., 2003 "Humanization of the anti-CD18 antibody 6.7: an unexpected effect of a framework residue in binding to antigen," *Mol Immunol* 39(15):941-952.
Campbell (Monoclonal Antibody Technology, Laboratory Techniques in Biochemistry and Molecular Biology, 1984, Elsevier Science Publishers B.V.: Amsterdam, The Netherlands, vol. 13, pp. 1-32).
Casset et al., 2003 "A peptide mimetic of an anti-CD4 monoclonal antibody by rational design," *Biochem Biophys Res Commun* 307(1):198-205.
Chien et al., 1989 "Significant structural and functional change of an antigen-binding site by a distant amino acid substitution: Proposal of a structural mechanism," *Proc Natl Acad Sci USA* 86(14):5532-5536.
Ciccotosto et al., 1995 "Expression, Processing and Secretion of Gastrin in Patients with Colorectal Carcinoma," *Gastroenterology* 109:1142-1153.

(Continued)

*Primary Examiner* — Stephen L Rawlings
(74) *Attorney, Agent, or Firm* — Buchanan, Ingersoll & Rooney PC

(57) ABSTRACT

The present disclosure is directed to progastrin monoclonal antibodies, fragments thereof, compositions comprising progastrin monoclonal antibodies, and methods of making and using progastrin monoclonal antibodies and compositions thereof. The present disclosure is directed to methods of treating colorectal cancer with progastrin monoclonal antibodies and compositions comprising progastrin monoclonal antibodies or fragments thereof. The present disclosure is further directed to methods comprising detection of progastrin, including methods of diagnosing colorectal cancer and methods of monitoring efficacy of anti-cancer therapy in subjects suffering from colorectal cancer.

20 Claims, 33 Drawing Sheets

Figure 3A:
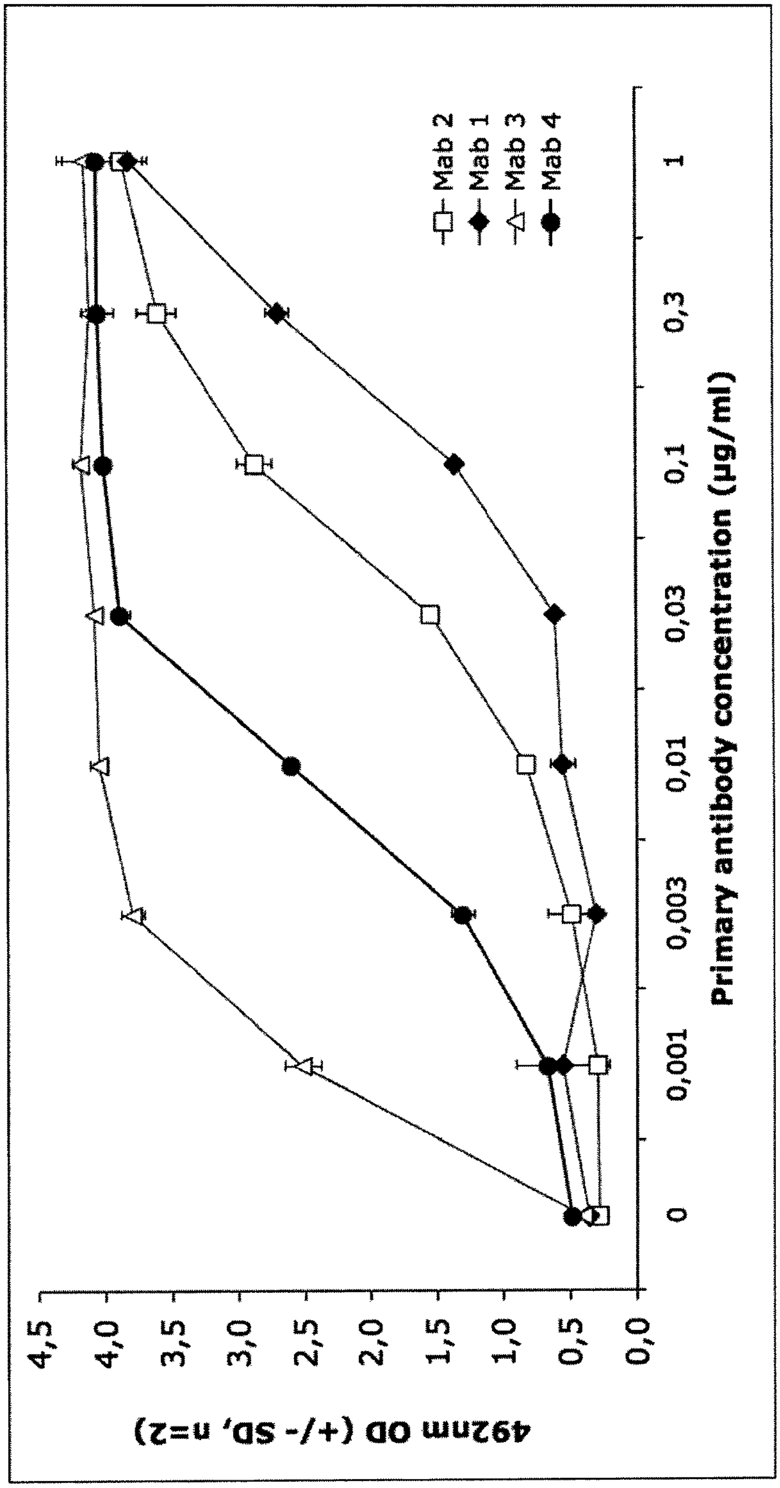

Specification includes a Sequence Listing.

(56) References Cited

OTHER PUBLICATIONS

De Pascalis et al., 2002 "Grafting of "Abbreviated" Complementarity-Determining Regions Containing Specificity-Determining Residues Essential for Ligand Contact to Engineer a Less Immunogenic Humanized Monoclonal Antibody," *J Immunol*169(6):3076-3084.

George et al., 1998 "Differential Effects of Anti-$\beta_2$-Glycoprotein I Antibodies on Endothelial Cells and on the Manifestations of Experimental Antiphospholipid Syndrome," *Circulation* 97:900-906.

Giusti et al., 1987 "Somatic diversification of S107 from an antiphosphocholine to an anti-DNA autoantibody is due to a single base change in its heavy chain variable region," *Proc Natl Acad Sci USA* 84(9):2926-2930.

Gussow et al., 1991 "Humanization of monoclonal antibodies," *Methods Enzymol* 203:99-121.

Holm et al., 2007 "Functional mapping and single chain construction of the anti-cytokeratin 8 monoclonal antibody TS1," *Mol Immunol* 44(6):1075-1084.

Hornbeck et al., 2001 "Enzyme-Linked Immunosorbent Assays (ELISA)," *Current Protocols in Molecular Biology*, Wiley, Ch. 11., p. 11.2.1-11.2.22.

Larrik et al., 1989 "Polymerase Chain Reaction Using Mixed Primesr: Cloning of Human Monoclonal Antibody Variable Region Genes from Single Hybridoma Cells," *Bio/Technology*, Nature Publishing Co., New York, U.S., v. 7, p. 934-938.

Larrik et al., 1989 "Rapid Cloning of Rearranged Immunoglobulin Genes from Human Hybridoma Cells Using Mixed Primers and the Polymerase Chain Reaction," *Biochemical and Biophysical Research Communications*, Academic Press Inc., Orlando, Fl., U.S., v. 160, p. 1250-1256.

Mariuzza et al., 1987 "The Structural Basis of Antigen-Antibody Recognition," *Annu Rev Biophys Biophys Chem* 16:139-159.

MacCallum et al., 1996 "Antibody-antigen Interactions: Contact Analysis and Binding Site Topography," *J Mol Biol* 262(5):732-745.

Ottewell et al., 2005 "COOH-terminal 26-amino acid residues of progastrin are sufficient for stimulation in murine colonic epithelium in vivo," *Am J Physiol Gastrointest Liver Physiol* 288:G541-549.

Rehfeld et al., 2004 "Naming progastrin-derived peptides," *Regul Pept* 120(1-3). 177-183.

Rudikoff et al., 1982 "Single amino acid substitution altering antigen-binding specificity," *Proc Natl Acad Sci USA* 79:1979-1983.

Singh et al., 2000 "Progastrin Expression Predisposes Mice to Colon Carcinomas," *Gastroenterology* 119:162-171.

Singh et al., 2007 "Development of Progastrin (PG) Specific Monoclonal Antibodies (Mabs) and PG Specific Vaccine For Attenuating Growth Factor Effects Of Autocrine And Endocrine PG-Like Pepticles On Colon Cancer Cells And Colon Carcinogenesis, respectively," *Proceedings of the American Association for Cancer Research Annual Meeting* (Apr. 2007, vol. 48, p. 845) and *98th Annual Meeting of the American Association for Cancer Research*, Los Angeles, CA (Abstract).

Toleikis et al., 2004 "Cloning Single-Chain Antibody Fragments (SCFV) From Hybridoma Cells," *Methods in Molecular Medicine*, Humana Press, Totowa, NJ, U.S., v. 94, p. 447-458.

Tom et al., 1976, "Human Colonic Adenocarcinoma Cells; 1. Establishment and Description of a New Line," In Vitro 12(3):180-191.

Vajdos et al., 2002 "Comprehensive Functional Maps of the Antigenbinding Site of an Anti-ErbB2 Antibody Obtained with Shotgun Scanning Mutagenesis ," *J Mol Biol* 320(2):415-428.

Van Solinge et al., 1993 "Expression but Incomplete Maturation of Progastrin in Colorectal Carcinomas," *Gastroenterology* 104:1099-1107.

Winkler et al., 2000 "Changing the Antigen Binding Specificity by Single Point Mutations of an Anti-p24 (HIV-1) Antibody," *J Immunol* 165(8):4505-4514.

Wu et al., 1994 "Humanization of a Murine Monoclonal Antibody by Simultaneous Optimization of Framework and CDR Residues," *J Mol Biol* 294(1):151-162.

Yakes et al., 2011 "Antibody characterization and immunoassays for palytoxin using an SPR biosensor," *Anal Bional Chem* 400(9):2865-2869.

Digital photographs of panels from poster presented at 2007 Annual Meeting of American Association for Cancer Research, corresponding to Singh et al., 2007, "Development of progastrin (PG) specific monoclonal antibodies (MAbs) and PG specific vaccine for attenuating growth factor effects of autocrine and endocrine PG-like peptides on colon cancer cells and colon carcinogenesis, respectively," *Proc. Amer. Assoc. Cancer Res.* Annual Meeting, vol. 48:845.

Written Opinion of the International Searching Authority from PCT/EP2010/006329, dated May 20, 2011.

LS 174T (ATCC® CL-188™), ATCC, https://www.atcc.org/Products/All/CL-188.aspx?geo_country=us (uploaded Sep. 14, 2018).

* cited by examiner

FIG. 1

| | | | | | |
|---|---|---|---|---|---|
| Preprogastrin: | M QRLCVYVLIF ALALAAFSEA | SWKPRSQQPD | APLGTGANRD | LELPWLEQQG | |
| | -21 -11 -1 | 1 | 11 | 21 | |
| | PASHHRRQLG | PQGPPHLVAD | PSKKQGPWLE | EEEEAYGWMD | FGRRSAEDEN |
| | 31 | 41 | 51 | 61 | 71 |
| Progastrin: | | | SWKPRSQQPD | APLGTGANRD | LELPWLEQQG |
| | | | 1 | 11 | 21 |
| | PASHHRRQLG | PQGPPHLVAD | PSKKQGPWLE | EEEEAYGWMD | FGRRSAEDEN |
| | 31 | 41 | 51 | 61 | 71 |
| G34: | QLG | PQGPPHLVAD | PSKKEGPWLE | EEEEAYGWMD | F-$NH_2$ |
| | | 41 | 51 | 61 | 71 |
| G34-Gly: | QLG | PQGPPHLVAD | PSKKEGPWLE | EEEEAYGWMD | FG |
| | | 41 | 51 | 61 | 71 |
| G17: | | | EGPWLE | EEEEAYGWMD | F-$NH_2$ |
| | | | | 61 | 71 |
| G17-Gly: | | | EGPWLE | EEEEAYGWMD | FG |
| | | | | 61 | 71 |
| CTFP: | | | | | SAEDEN |
| | | | | | 75 |

FIG. 2A

```
         10        20        30        40        50        60        70        80        90       100
GAGGTTCAGCTCCAGCAGTCTGGGACTGTGCTGGCCAAGGCTGGGGCTTCCGTGAAGATGTCCTGCAAGGCTTCTGGCTACATCTTTACCAGCTACTGGG
 E  V  Q  L  Q  Q  S  G  T  V  L  A  R  P  G  A  S  V  K  M  S  C  K  A  S  G  Y  I  F  T  S  Y  W
                                                                              mVHCDR 1.3 (G Y I F T S Y W)

        110       120       130       140       150       160       170       180       190       200
TACACTGGGTTAAACAGAGGCCTGGACAGGGTCTAGAATGGATTGGTGGTTTTTATCCTGGAAATAGTGATTCTAGGTACAACCAGAAATTCAAGGGCAA
V  H  W  V  K  Q  R  P  G  Q  G  L  E  W  I  G  G  F  Y  P  G  N  S  D  S  R  Y  N  Q  K  F  K  G  K
                                                    mVHCDR 2.3 (F Y P G N S D S)

        210       220       230       240       250       260       270       280       290       300
GGCCACACTGACTGCAGTCACATCCGCCAGTACTGCCTACATGGACCTCAGCAGCCTGACAAATGAGGACTCTGCGGTCTATTTCTGTACAAGAAGAGAT
  A  T  L  T  A  V  T  S  A  S  T  A  Y  M  D  L  S  S  L  T  N  E  D  S  A  V  Y  F  C  T  R  R  D
                                                                                 mVHCDR 3.3 (T R R D)

        310       320       330       340
AGTCCCCAGTACTGGGGCCAAGGCACCACTCTCACAGTCTCCTCA
S  P  Q  Y  W  G  Q  G  T  T  L  T  V  S  S
mVHCDR 3.3 (S P Q Y)
```

FIG. 2B

```
        10         20         30         40         50         60         70         80         90        100
GATGTTTTGATGACCCAAACTCCACTCTCCCTGCCTGTCAGTCTTGGAGATCAAGCCTCCATCTCTTGCAGATCTAGTCAGAGCATTGTACATAGTAATG
 D  V  L  M  T  Q  T  P  L  S  L  P  V  S  L  G  D  Q  A  S  I  S  C  R  S  S  Q  S  I  V  H  S  N
                                                                                ________________________
                                                                                      mVLCDR 1.3

       110        120        130        140        150        160        170        180        190        200
GAAACACCTATTTAGAATGGTACCTGCAGAAACCAGGCCAGTCTCCAAAGCTCCTGATCTACAAAGTTTCCAACCGATTTTCTGGGGTCCCAGACAGGTT
 G  N  T  Y  L  E  W  Y  L  Q  K  P  G  Q  S  P  K  L  L  I  Y  K  V  S  N  R  F  S  G  V  P  D  R  F
___________                                                      ________
mVLCDR 1.3                                                      mVLCDR 2.3

       210        220        230        240        250        260        270        280        290        300
CAGTGGCAGTGGATCAGGGACAGATTTCACACTCAAGATCAGCAGACTGGAGGCTGAGGATCTGGGAGTTTATTACTGCTTTCAAGGTTCACATGTTCCG
 S  G  S  G  S  G  T  D  F  T  L  K  I  S  R  L  E  A  E  D  L  G  V  Y  Y  C  F  Q  G  S  H  V  P
                                                                                ________________________
                                                                                      mVLCDR 3.3

       310        320        330
TTCACGTTCGGAGGGGGGACCAAGCTGGAAATAAAA
 F  T  F  G  G  G  T  K  L  E  I  K
______
mVLCDR 3.3
```

FIG. 2C

```
        10        20        30        40        50        60        70        80        90       100
CAGGTTCAGTTGCAGCAGTCTGGAGCTGAGCTGATGAAGCCAGGGGCCTCAGTGAAGATATCCTGCAAGGCTACTGGCTACACATTCAGTAGCTCCTGGA
 Q  V  Q  L  Q  Q  S  G  A  E  L  M  K  P  G  A  S  V  K  I  S  C  K  A  T  G  Y  T  F  S  S  S  W
                                                                             mVHCDR 1.4

       110       120       130       140       150       160       170       180       190       200
TAGAGTGGTTAAAACAGAGGCCTGGACATGGCCTTGAGTGGATTGGAGAGTTTTTACCTGGAAGTGGTAGTACAGACTACAATGAGAAGTTCAAGGGCAA
I  E  W  L  K  Q  R  P  G  H  G  L  E  W  I  G  E  F  L  P  G  S  G  S  T  D  Y  N  E  K  F  K  G  K
                                                      mVHCDR 2.4

       210       220       230       240       250       260       270       280       290       300
GGCCACATTCACTGCAGACACATCCTCCGACACAGCCTACATGCTACTCAGCAGCCTGACATCTGAGGACTCTGCCGTCTATTACTGTGCAACTSATGGT
  A  T  F  T  A  D  T  S  S  D  T  A  Y  M  L  L  S  S  L  T  S  E  D  S  A  V  Y  Y  C  A  T  D  G
                                                                                          mVHCDR 3.4

       310       320       330       340       350
AATTATGACTGGTTTGCTTACTGGGGCCAAGGGACTCTGGTCACTGTCTCTGCA
 N  Y  D  W  F  A  Y  W  G  Q  G  T  L  V  T  V  S  A
    mVHCDR 3.4
```

FIG. 2D

```
       10        20        30        40        50        60        70        80        90       100
GATCTTGTGATGACCCAAACTCCACTCTCCCTGCCTGTCAGTCTTGGAGATCAAGCCTCCATCTCTTGCAGATCTAGTCAGAGCCTTGTACACAGTAGTG
 D  L  V  M  T  Q  T  P  L  S  L  P  V  S  L  G  D  Q  A  S  I  S  C  R  S  S  Q  S  L  V  H  S  S
                                                                                 ___________________
                                                                                    mVL CDR 1.4

      110       120       130       140       150       160       170       180       190       200
GAGTCACCTATTTACATTGGTACCTGCAGAAGCCAGGCCAGTCTCCAAAGCTCCTGATCTACAAAGTTTCCAACCGATTTTCTGGGGTCCCAGACAGGTT
 G  V  T  Y  L  H  W  Y  L  Q  K  P  G  Q  S  P  K  L  L  I  Y  K  V  S  N  R  F  S  G  V  P  D  R  F
___________                                                      _______
mVL CDR 1.4                                                    mVL CDR 2.4

      210       220       230       240       250       260       270       280       290       300
CAGTGGCAGTGGATCAGGGACAGATTTCACACTCAAGATCAGCAGAGTGGAGGCTGAGGATCTGGGAGTTTATTTCTGCTCTCAAAGTACACATGTTCCT
 S  G  S  G  S  G  T  D  F  T  L  K  I  S  R  V  E  A  E  D  L  G  V  Y  F  C  S  Q  S  T  H  V  P
                                                                                 ___________________
                                                                                    mVL CDR 3.4

      310       320       330
CCCACGTTCGGCTCGGGGACAAAGTTGGAAATAAAA
 P  T  F  G  S  G  T  K  L  E  I  K
___
mVL CDR 3.4
```

FIG. 2E

```
        10        20        30        40        50        60        70        80        90       100
GAAGTGCAGCTGGTGGAGTCTGGGGGAGGCTTAGTGAAGCCTGGAGGGTCCCTGAAACTCTCCTGTGCAGCCTCTGGATTCACTTTCACTACCTATGCCA
 E  V  Q  L  V  E  S  G  G  G  L  V  K  P  G  G  S  L  K  L  S  C  A  A  S  G  F  T  F  T  T  Y  A
                                                                            ___________________
                                                                               mVHCDR 1.8

       110       120       130       140       150       160       170       180       190       200
TGTCTTGGGTTCGCCAGACTCCGGAGAAGAGGCTGGAGTGGGTCGCAACCATTAGTAGTGGTGGTACTTACACCTACTATCCAGACAGTGTGAAGGGTCG
M  S  W  V  R  Q  T  P  E  K  R  L  E  W  V  A  T  I  S  S  G  G  T  Y  T  Y  Y  P  D  S  V  K  G  R
                                                    _____________________
                                                        mVHCDR 2.8

       210       220       230       240       250       260       270       280       290       300
ATTCACCATCTCCAGAGACAATGCCAAGAACGCCCTATACCTGCAAATGAGCAGTCTGAGGTCTGAGGACACGGCCATGTATTACTGTGCAACACAGGGG
  F  T  I  S  R  D  N  A  K  N  A  L  Y  L  Q  M  S  S  L  R  S  E  D  T  A  M  Y  Y  C  A  T  Q  G
                                                                                          ___________
                                                                                          mVHCDR 3.8

       310       320       330       340
AATTACTCTTTGGACTTCTGGGGCCAAGGCACCTCTCTCACAGTCTCCTCA
 N  Y  S  L  D  F  W  G  Q  G  T  S  L  T  V  S  S
_______________
  mVHCDR 3.8
```

FIG. 2F 10 20 30 40 50 60 70 80 90 100
GACATTGTGATGACGCAGGCTGCATCCTCTAATCCAGTCACTCTTGGAACATCCGCTTCCATCTCCTGCAGGTCTAGTAAGAGTCTCCGACATACTAAAG
D I V M T Q A A S S N P V T L G T S A S I S C R S S K S L R H T K $mV_L$CDR 1.8 (K S L R H T K)

110 120 130 140 150 160 170 180 190 200
GCATCACTTTTTTGTATTGGTATCTGCAGAAGCCAGGCCAGTCTCCTCAGCTCCTGATTTATCAGATGTCCAACCTTGCCTCAGGAGTCCCAGACAGGTT
G I T F L Y W Y L Q K P G Q S P Q L L I Y Q M S N L A S G V P D R F $mV_L$CDR 1.8 (G I T F) $mV_L$CDR 2.8 (Q M S)

210 220 230 240 250 260 270 280 290 300
CAGTAGCAGTGGGTCAGGAACTGATTTCACACTGAGAATCAGCAGAGTGGAGGCTGAGGATTTGGGTGTTTATTACTGTGCTCAAAATCTAGAACTTCCG
S S S G S G T D F T L R I S R V E A E D L G V Y Y C A Q N L E L P $mV_L$CDR 3.8 (A Q N L E L P)

310 320 330
CTCACGTTCGGTGCTGGGACCAAGCTGGAGCTGAAA
L T F G A G T K L E L K $mV_L$CDR 3.8 (L T)

FIG. 2G

```
        10        20        30        40         50         60       70       80        90       100
GAGGTGCAGCTGGTGGAGTCTGGGGGAGGCTTGGTGCAGCCTGGAGGGTCCCTGAAACTCTCCTGTGCAGCCTCTGGATTCATTTTCAGTAGCTATGGCA
 E  V  Q  L  V  E  S  G  G  G  L  V  Q  P  G  G  S  L  K  L  S  C  A  A  S  G  F  I  F  S  S  Y  G
                                                                             --------------------------
                                                                                  mVHCDR 1.13

       110       120       130       140        150        160      170      180       190       200
TGTCTTGGGTTCGCCAGTCTCCAGACAGGAGGCTGGAGTTGGTCGCAAGTATTAATACTTTTGGTGATAGAACCTATTATCCAGACAGTGTGAAGGGCCG
M  S  W  V  R  Q  S  P  D  R  R  L  E  L  V  A  S  I  N  T  F  G  D  R  T  Y  Y  P  D  S  V  K  G  R
                                                    ------------------------
                                                         mVHCDR 2.13
       210       220       230       240        250        260      270      280       290       300
ATTCACCATCTCCAGAGACAATGCCAAGAACACCCTGTACCTGCAAATGACCAGTCTGAAGTCTGAGGACACAGCCATTTATTACTGTGCAAGAGGGACC
  F  T  I  S  R  D  N  A  K  N  T  L  Y  L  Q  M  T  S  L  K  S  E  D  T  A  I  Y  Y  C  A  R  G  T
                                                                                        -------------
                                                                                         mVHCDR 3.13

       310       320       330       340
GGAACCTACTGGGGCCAAGGCACCACTCTCACAGTCTCCTCA
 G  T  Y  W  G  Q  G  T  T  L  T  V  S  S
 ---------
 mVHCDR 3.13
```

FIG. 2H

```
          10        20        30        40        50        60        70        80        90       100
GATGTTGTGCTGACCCAGACTCCACTCACTTTGTCGGTTAACATTGGACAACCAGCCTCCATCTCCTGCAAGTCAAGTCAGAGCCTCTTAGATAGTGATG
 D  V  V  L  T  Q  T  P  L  T  L  S  V  T  I  G  Q  P  A  S  I  S  C  K  S  S  Q  S  L  L  D  S  D
                                                                              __________________
                                                                                mVLCDR 1.13

         110       120       130       140       150       160       170       180       190       200
GAAAGACATATTTGAATTGGTTGTTACAGAGGCCAGGCCAGTCTCCAAAGCGCCTAATCTATCTGGTGTCTAAACTGGACTCTGGAGTCCCTGACAGGTT
 G  K  T  Y  L  N  W  L  L  Q  R  P  G  Q  S  P  K  R  L  I  Y  L  V  S  K  L  D  S  G  V  P  D  R  F
__________                                                        ________
mVLCDR 1.13                                                       mVLCDR 2.13

         210       220       230       240       250       260       270       280       290       300
CACTGGCAGTGGATCAGGGACAGATTTCACACTGAAAATCAGCAGAGTGGAGGCTGAGGATTTGGGAGTTTATTATTGCTGGCAAGGTACACATTTTCCT
  T  G  S  G  S  G  T  D  F  T  L  K  I  S  R  V  E  A  E  D  L  G  V  Y  Y  C  W  Q  G  T  H  F  P
                                                                                ___________________
                                                                                  mVLCDR 3.13

         310       320       330
CAGACGTTCGGTGGAGGCACCAAGCTGGAAATCAAA
 Q  T  F  G  G  G  T  K  L  E  I  K
 _____
mVLCDR 3.13
```

FIG. 2I

```
         10        20        30        40         50         60        70        80        90       100
CAGGTCCAACTGCAGCAGTCTGGGGCTGAACTGGTGAAGCCTGGGGCTTCAGTGAAGTTGTCCTGCAAGGCTTCTGGCTACACCTTCACCAGCTACTATA
 Q  V  Q  L  Q  Q  S  G  A  E  L  V  K  P  G  A  S  V  K  L  S  C  K  A  S  G  Y  T  F  T  S  Y  Y
                                                                             -----------------------
                                                                                 mVHCDR 1.16

        110       120       130       140        150        160       170       180       190       200
TGTACTGGGTGAAGCAGAGGCCTGGACAAGGCCTTGAGTGGATTGGAGAGATTAATCCTAGCAATGGTGGTACTAACTTCAATGAGAAGTTCAAGAGCAA
M  Y  W  V  K  Q  R  P  G  Q  G  L  E  W  I  G  E  I  N  P  S  N  G  G  T  N  F  N  E  K  F  K  S  K
                                                   ------------------------
                                                      mVHCDR 2.16
        210       220        230      240        250        260       270       280       290       300
GGCCACACTGACTGTAGACAAATCCTCCAGCACAGCATACATGCAACTCAGCAGCCTGACATCTGAGGACTCTGCGGTCTATTACTGTACAAGAGGCGGT
 A  T  L  T  V  D  K  S  S  S  T  A  Y  M  Q  L  S  S  L  T  S  E  D  S  A  V  Y  Y  C  T  R  G  G
                                                                                         -----------
                                                                                         mVHCDR 3.16

        310       320        330      340        350
TACTACCCCTTTGACTACTGGGGCCAAGGCACCACTCTCACAGTCTCCTCA
 Y  Y  P  F  D  Y  W  G  Q  G  T  T  L  T  V  S  S
 -----------------
   mVHCDR 3.16
```

FIG. 2J

```
       10        20        30        40        50        60        70        80        90       100
GATGTTGTGATGACCCAGACTCCACTCACTTTGTCGGTTACCATTGGGCGCCCAGCCTCCATCTCTTGCAAGTCAAGTCAGAGCCTCTTAGACAGTGATG
 D  V  V  M  T  Q  T  P  L  T  L  S  V  T  I  G  R  P  A  S  I  S  C  K  S  S  Q  S  L  L  D  S  D
                                                                                ____________________
                                                                                    mVLCDR 1.16

      110       120       130       140       150       160       170       180       190       200
GAAAGACATATTTGTATTGGTTGTTACAGAGGCCAGGCCAGTCTCCAAAGCGCCTAATCTATCTGGTGTCTGAGCTGGACTCTGGAGTCCCTGACAGGAT
G  K  T  Y  L  Y  W  L  L  Q  R  P  G  Q  S  P  K  R  L  I  Y  L  V  S  E  L  D  S  G  V  P  D  R  I
__________                                                      _________
mVLCDR 1.16                                                     mVLCDR 2.16
      210       220       230       240       250       260       270       280       290       300
CACTGGCAGTGGGTCGGGGACAGATTTCACACTGAAGATCAGCAGAGTGGAGGCTGAGGATTTGGGAGTTTATTATTGCTGGCAAGGAACACATTCTCCG
  T  G  S  G  S  G  T  D  F  T  L  K  I  S  R  V  E  A  E  D  L  G  V  Y  Y  C  W  Q  G  T  H  S  P
                                                                              _____________________
                                                                                 mVLCDR 3.16

      310       320       330
TACAGGTTCGGAGGGGGGACCAAGCTGGAAATAAAA
 Y  T  F  G  G  G  T  K  L  E  I  K
______
mVLCDR 3.16
```

FIG. 2K

```
        10        20        30        40        50        60        70        80        90       100
GATGTGCAGCTTCAGGAGTCGGGACCTGGCCTGGTGAAACCTTCTCAGTCTCTGTCCCTCACATGCACTGTCACTGGCTACTCAATCACCAGTGATTATG
 D  V  Q  L  Q  E  S  G  P  G  L  V  K  P  S  Q  S  L  S  L  T  C  T  V  T  G  Y  S  I  T  S  D  Y
                                                                              mVHCDR 1.19

       110       120       130       140       150       160       170       180       190       200
CCTGGAATTGGATCCGGCAGTTTCCAGGAAACAAACTGGAGTGGATGGGCTACATAAGCTTCAGTGGTTACACTAGTTACAACCCATCTCTCAAAAGTCG
A  W  N  W  I  R  Q  F  P  G  N  K  L  E  W  M  G  Y  I  S  F  S  G  Y  T  S  Y  N  P  S  L  K  S  R
                                                  mVHCDR 2.19

       210       220       230       240       250       260       270       280       290       300
AATCTCTGTCACTCGGGACACATCCAGGAACCAATTCTTCCTCCAGTTGACTTCTGTGACTACTGAGGACACAGCCACATATTACTGTGCAAGAGAGGTC
  I  S  V  T  R  D  T  S  R  N  Q  F  F  L  Q  L  T  S  V  T  T  E  D  T  A  T  Y  Y  C  A  R  E  V
                                                                                      mVHCDR 3.19

       310       320       330       340       350       360
AACTATGGGGACTCCTACCACTTTGACTACTGGGGCCAAGGCACCATTGTCACAGTCTCCTCA
 N  Y  G  D  S  Y  H  F  D  Y  W  G  Q  G  T  I  V  T  V  S  S
     mVHCDR 3.19
```

FIG. 2L

```
        10        20        30        40        50        60        70        80        90        100
CAACTTGCGCTCACTCAGTCATCTTCAGCCTCTTTCTCCCTGGGAGCCTCAGCAAAACTAACGTGCACTTTGAGTAGTCAACACAGAACGTACACCATTG
 Q  L  A  L  T  Q  S  S  S  A  S  F  S  L  G  A  S  A  K  L  T  C  T  L  S  S  Q  H  R  T  Y  T  I
                                                                              ---------------------
                                                                                 mVLCDR 1.19

        110       120       130       140       150       160       170       180       190       200
AATGGTATCAGCAACAGTCACTCAAGCCTCCTAAGTATGTGATGGAGGTTAAGAAAGATGGAAGCCACAGCACAGGTCATGGGATTCCTGATCGCTTCTC
E  W  Y  Q  Q  Q  S  L  K  P  P  K  Y  V  M  E  V  K  K  D  G  S  H  S  T  G  H  G  I  P  D  R  F  S
                                                ---------------------
                                                   mVLCDR 2.19

        210       220       230       240       250       260       270       280       290       300
TGGATCCAGTTCTGGTGCTGATCGCTACCTCAGCATTTCCAACATCCAGCCTGAAGATGAAGCAATATACATCTGTGGTGTGGGTGATGCAATTAAGGGA
  G  S  S  S  G  A  D  R  Y  L  S  I  S  N  I  Q  P  E  D  E  A  I  Y  I  C  G  V  G  D  A  I  K  G
                                                                             ------------------------
                                                                                 mVLCDR 3.19

        310       320       330       340
CAATCTGTGTTTGTTTTCGGCGGTGGCACCAAGGTCACTGTCCTA
 Q  S  V  F  V  F  G  G  G  T  K  V  T  V  L
 ---------------
  mVLCDR 3.19
```

MONOCLONAL ANTIBODIES TO PROGASTRIN AND THEIR USES

1. CROSS REFERENCE TO RELATED APPLICATIONS

This application is a divisional of U.S. application Ser. No. 12/906,041, filed Oct. 15, 2010, now U.S. Pat. No. 9,611,320, issued on Apr. 4, 2017, which claims the benefit under 35 U.S.C. § 119(e) of provisional application No. 61/252,625, filed Oct. 16, 2009, the contents of all which are incorporated herein by reference in their entirety.

2. STATEMENT REGARDING FEDERALLY SPONSORED RESEARCH

None.

3. PARTIES TO A JOINT RESEARCH AGREEMENT

None.

4. REFERENCE TO SEQUENCE LISTING, TABLE OR COMPUTER PROGRAM

The Sequence Listing submitted concurrently herewith under 37 CFR § 1.821 in a computer readable form (CRF) via EFS-Web as file name Sequence_001US.txt is incorporated herein by reference. The electronic copy of the Sequence Listing was created on Oct. 12, 2010, with a file size of 76,910 bytes.

5. FIELD OF INVENTION

The present disclosure is directed to, among other things, monoclonal antibodies to progastrin, compositions and methods for making such antibodies, and methods of using such antibodies, for example in the diagnosis and/or treatment of colorectal cancer.

6. BACKGROUND

Colorectal Cancer (CRC) is a major public health issue, affecting more than 1,000,000 people each year and accounting for more than 500,000 deaths each year. CRC is the second leading cause of death due to cancer. In the United States alone, for 2009, approximately 147,000 new cases and over 49,900 deaths due to CRC were reported. There are three forms of CRC: sporadic CRC; hereditary non-polyposis colon cancer (HNPCC), caused by germline mutations in DNA mismatch repair genes; and familial adenomatous polyposis (FAP), due to germline mutations in the APC gene. Sporadic CRC accounts for nearly 85% of cases, while HNPCC accounts for about 5% and FAP accounts for about 1% (Heyer et al., 1999, Oncogene 18:5325-5333).

Clinical management of CRC typically involves surgical resection of tumors often accompanied by chemotherapy. Presently, about 50% of CRC patients die within five years of diagnosis. The lack of reliable screening tests and the ineffectiveness of currently available therapies are major causes of the high mortality rate. There is an urgent need for new clinical approaches for diagnosing CRC, as well as for treatments effective against colorectal cancer tumors that have minimal adverse effects on otherwise healthy tissue.

7. SUMMARY

The present application provides compositions and methods useful for diagnosing and/or treating colorectal cancer (CRC) in animals, including humans. The various inventions described in the application are based, in part, on the applicants' discovery of monoclonal antibodies that specifically bind progastrin (PG), for example, human progastrin (hPG), a polypeptide produced by CRC tumor cells, and that exhibit antiproliferative properties in in vitro models of CRC.

Progastrin is produced by colorectal tumor cells and is thought to stimulate proliferation of these cells by triggering a signal transduction pathway that blocks the cells' normal differentiation processes, including those processes that lead to cell death. Depletion of the gastrin gene transcript that encodes progastrin induces cell differentiation and programmed cell death in tumor cells in in vitro and in vivo CRC models, reducing tumor cell proliferation. While not intending to be bound by any theory of operation, through binding of PG, anti-hPG antibodies are thought to block or inhibit its ability to interact with its signaling partner(s). This, in turn, inhibits a signal transduction pathway in colorectal tumor cells that would otherwise lead to proliferation.

Accordingly, in one aspect, the present disclosure provides monoclonal antibodies that specifically bind PG, for example hPG, but not other products of the gastrin gene. Referring to FIG. 1, the gastrin gene is translated into a 101-amino acid polypeptide, called pre-progastrin, which contains a signal sequence (underlined) that is cleaved, giving rise to progastrin, an 80-amino-acid polypeptide. Progastrin, in turn, is cleaved to generate a 34-amino-acid product, corresponding to residues 38 to 71 of progastrin, which is then extended at its carboxy terminus with a glycine residue, generating glycine-extended G34 ("G34-Gly"). A by-product of this cleavage is a 5-amino-acid peptide, called the C-terminal flanking peptide, or CTFP, which includes residues 75 to 80 of progastrin. G34-Gly is then further cleaved to generate a 17 residue polypeptide corresponding in sequence to residues 55 to 71 of progastrin and referred to as G17-Gly. Removal of the C-terminal glycines of G34-Gly and G17-Gly, followed by C-terminal amidation, yields G34 and G17, respectively, both of which are C-terminal amidated. Thus, while the first 37 residues of progastrin are unique to it (i.e. not present in its processing products, such as G34, G34-Gly, G17, G17-Gly, or CFTP), residues 38 to 80 of PG are also present in post-translational products of the gastrin gene.

Applicants have discovered that, while anti-PG monoclonal antibodies can be raised using methods known to those of skill, the selection of antigen is important. Not all antigens derived from hPG stimulate production of monoclonal antibodies that specifically bind hPG under physiological conditions. As described below, various antigens used to raise polyclonal antibodies to hPG, such as full length recombinant human progastrin (see, e.g., Singh WO 08/076454) and peptides corresponding to the last ten amino acids at the C-terminal end of hPG (see, e.g., Hollande WO 07/135542), failed to generate anti-hPG monoclonal antibodies. Applicants, however, have discovered antigenic N- and C-terminal sequences within the hPG sequence that can be used to generate monoclonal antibodies that specifically bind hPG. Quite surprisingly, applicants have discovered that it is not necessary to limit the antigen sequences to stretches of the PG sequence that are unique to it to obtain monoclonal antibodies that specifically bind PG and not the other gastrin gene-derived products. Peptide antigens having sequences in common with other products of the gastrin gene, for example G17, G34, and CTFP, yielded monoclonal antibodies that not only bind hPG, but bind it specifically.

Applicants have generated monoclonal antibodies using antigens derived from different regions of the hPG molecule. Monoclonal anti-PG antibodies obtainable using a peptide antigen having a sequence corresponding to an N-terminal region of hPG, and/or that bind to an N-terminal region of hPG, are referred to herein as "N-terminal anti-hPG monoclonal antibodies." A specific exemplary antigenic region that can be used to construct an immunogen useful for obtaining N-terminal anti-PG monoclonal antibodies corresponds to residues 1 to 14 of hPG: SWKPRSQQPDAPLG (SEQ ID NO:25). Exemplary immunogens including this antigen useful for obtaining N-terminal anti-PG monoclonal antibodies are described in Table 1A and the Examples section.

Monoclonal anti-PG antibodies obtainable using a peptide antigen having a sequence corresponding to a C-terminal region of hPG, and/or that bind a C-terminal region of hPG, are referred to herein as "C-terminal anti-hPG monoclonal antibodies." A specific exemplary antigenic region that can be used to construct an immunogen useful for obtaining C-terminal anti-PG monoclonal antibodies corresponds to residues 55 to 80 of hPG: QGPWLEEEEEAYGWMDFG RRSAEDEN (SEQ ID NO:27). Exemplary immunogens including this antigen useful for obtaining C-terminal anti-PG monoclonal antibodies are described in Table 1B and the Examples section.

For some uses, it is desirable to have anti-hPG monoclonal antibodies with high affinity to hPG. For certain uses, such as therapeutic uses, an affinity of at least about 100 nM is desirable, although antibodies having greater affinities, for example affinities of at least about 90 nM, 80 nM, 70 nM, 60 nM, 50 nM, 40 nM, 30 nM, 25 nM, 20 nM, 15 nM, 10 nM, 7 nM, 6 nM, 5 nM, 4 nM, 3 nM, 2 nM, 1 nM, 0.1 nM, 0.01 nM, or even greater, may be desirable. The various specific exemplary anti-PG monoclonal antibodies disclosed herein exhibit affinities ranging from $10^{-6}$ to $10^{-12}$M (see Table 6). An anti-PG monoclonal antibody having an affinity especially suited for a particular desired application can be readily selected from amongst these, or generated or designed using the various immunogens, complementarity determining region (CDR) sequences, variable heavy ($V_H$) and variable light ($V_L$) chain sequences and methods described herein. The affinity of any particular anti-PG monoclonal antibody can be determined using techniques well known in the art or described herein, such as for example, ELISA, isothermal titration calorimetry (ITC), BIACORE®, or fluorescent polarization assay.

hPG is a relatively small polypeptide, being only 80 amino acids in length. It would have been expected that any monoclonal antibody that specifically binds hPG with a relatively high affinity (e.g., at least about 10 nM) would interfere with PG's ability to interact with its signaling partner(s), and, as a result, inhibit proliferation of CRC cells. However, Applicants have discovered that not all anti-PG monoclonal antibodies are neutralizing (i.e., not all monoclonal antibodies that bind PG interfere with or inhibit its biological signaling activity). Indeed, Applicants have discovered that some anti-PG monoclonal antibodies, despite exhibiting high specificity and high affinity for PG, do not neutralize PG. For example, anti-hPG MAb14 binds hPG with a $K_D$ of about 6 pM but does not inhibit the growth of CRC cells in vitro as detailed in the Examples section below. While non-neutralizing monoclonal antibodies that specifically bind hPG are useful for diagnostic purposes, those anti-hPG monoclonal antibodies that neutralize PG are particularly suited for therapeutic applications to treat CRC.

As used herein, a "neutralizing anti-hPG monoclonal antibody" is an anti-hPG monoclonal antibody that yields a statistically significant reduction in the number of live CRC cells in a test sample treated with the anti-hPG monoclonal antibody as compared to a control sample treated with a non-specific monoclonal antibody. A specific assay for assessing the ability of any particular anti-hPG monoclonal antibody to neutralize hPG is described in the Detailed Description section below. Those anti-hPG monoclonal antibodies that exhibit at least about a 50% reduction in the number of live cells in this assay are believed to be especially useful in treating CRC, although anti-hPG monoclonal antibodies exhibiting lower levels of neutralizing activity, for example, a statistically significant reduction of 40%, 30%, 20%, 15%, or even 10% in the number of live cells in this assay are expected to provide therapeutic benefits.

Accordingly, in some embodiments, the anti-PG monoclonal antibodies are neutralizing anti-PG monoclonal antibodies. It has been discovered that the ability of an anti-PG monoclonal antibody to neutralize PG is not epitope dependent. As exemplified in the Examples section, both N-terminal and C-terminal anti-PG antibodies have neutralizing activity. Thus, in some embodiments the neutralizing anti-PG monoclonal antibodies are N-terminal neutralizing antibodies, in other embodiments, the anti-PG monoclonal antibodies are C-terminal neutralizing antibodies.

Epitope mapping reveals that N-terminal anti-PG monoclonal antibodies do not all bind the same epitope, even when raised against the same immunogen. The same is true of C-terminal anti-hPG monoclonal antibodies. The epitopes bound by exemplary N-terminal and C-terminal anti-hPG monoclonal antibodies, as identified via alanine scanning and SPOT® technique, are provided in Examples section, in Tables 8 and 9.

In some embodiments, the anti-hPG monoclonal antibodies bind an epitope including an amino acid sequence corresponding to an N-terminal portion of hPG. In specific embodiments, N-terminal anti-hPG monoclonal antibodies bind an epitope that includes residues 10 to 14 of hPG (SEQ ID NO:28), residues 9 to 14 of hPG (SEQ ID NO:29), residues 4 to 10 of hPG (SEQ ID NO:30), residues 2 to 10 of hPG (SEQ ID NO:31), or residues 2 to 14 of hPG (SEQ ID NO:32).

In some embodiments, the anti-hPG monoclonal antibodies bind an epitope including an amino acid sequence corresponding to a portion of a C-terminal region of hPG. In specific embodiments, C-terminal anti-hPG monoclonal antibodies bind an epitope that includes residues 71 to 74 of hPG (SEQ ID NO:33), residues 69 to 73 of hPG (SEQ ID NO:34), residues 76 to 80 of hPG (SEQ ID NO:35), or residues 67 to 74 of hPG (SEQ ID NO:36).

It is expected that corresponding CDRs and/or $V_H$ and $V_L$ chains of anti-hPG monoclonal antibodies that bind approximately the same epitopes could be interchanged to yield new anti-hPG monoclonal antibodies. For example, as noted in Table 9, exemplary anti-hPG monoclonal antibodies MAb 5 and MAb 6 bind the same epitope. An anti-hPG monoclonal antibody can be designed that includes, in its $V_L$ chain, various combinations of the $V_L$ CDRs of these two antibodies, and/or in its $V_H$ chain various combinations of the $V_H$ CDRs of these two antibodies. As a specific example, to illustrate the various combinations possible, such an antibody could include in its $V_L$ chain, CDRs 1 and 2 of MAb 5 ($V_L$ CDR1.5 and $V_L$ CDR2.5, respectively) and CDR 3 of MAb 6 ($V_L$ CDR3.6), and in its $V_H$ chain, CDR 1 of MAb 6 ($V_H$ CDR1.6) and CDRs 2 and 3 of MAb 5 ($V_H$ CDR2.5 and $V_H$ CDR3.5, respectively).

Several anti-hPG monoclonal antibodies having high specificity and affinity for hPG and that exhibit good anti-tumor activity in in vitro assays have been identified, and in some instances the sequences of their CDRs, sequences of their $V_H$ and $V_L$ chains, and/or sequences of proposed $V_H$ and $V_L$ chains for humanized versions, determined. Several hybridomas have also been deposited. All of these exemplary anti-hPG monoclonal antibodies, as well as other specific embodiments of anti-hPG monoclonal antibodies useful in the various kits and methods described herein, for example monoclonal antibodies that compete for binding PG with a reference antibody, are described in more detail in the Detailed Description section.

Anti-hPG monoclonal antibodies of the disclosure include antibodies that compete with a reference anti-hPG monoclonal antibody for binding hPG. The reference anti-hPG monoclonal antibody may be any of the anti-hPG monoclonal antibodies described herein. Non-limiting examples include: antibodies comprising three $V_L$ CDRs and three $V_H$ CDRs as described herein; antibodies comprising a $V_H$ chain and a $V_L$ chain having amino acid sequences as set forth herein; antibodies comprising humanized heavy and light chain polypeptides as set forth herein; antibodies produced by any one of the hybridomas disclosed herein; antibodies that bind to an epitope within hPG as disclosed herein.

The anti-PG monoclonal antibodies described herein can be in the form of full-length antibodies, multiple chain or single chain antibodies, fragments of such antibodies that selectively bind PG (including but not limited to Fab, Fab', $(Fab')_2$, Fv, and scFv), surrobodies (including surrogate light chain construct), single domain antibodies, humanized antibodies, camelized antibodies and the like. They also can be of, or derived from, any isotype, including, for example, IgA (e.g., IgA1 or IgA2), IgD, IgE, IgG (e.g. IgG1, IgG2, IgG3 or IgG4), or IgM. In some embodiments, the anti-PG antibody is an IgG (e.g. IgG1, IgG2, IgG3 or IgG4).

Anti-PG monoclonal antibodies can be of human or non-human origin. Examples of anti-PG antibodies of non-human origin include but are not limited to, those of mammalian origin (e.g., simians, rodents, goats, and rabbits). Anti-PG monoclonal antibodies for therapeutic use in humans are preferably humanized.

In another aspect, the present disclosure provides nucleic acids capable of being used to produce anti-PG monoclonal antibodies. Nucleic acids encoding immunoglobulin light chain and heavy chain polypeptides for the anti-hPG monoclonal antibodies described herein, and vectors comprising the nucleic acids are provided. Additionally, prokaryotic and eukaryotic host cells transformed with such vectors are provided herein, as well as eukaryotic, e.g., mammalian, host cells engineered to express the light and heavy chain polypeptides of the anti-hPG monoclonal antibodies are provided. Also provided are host cells capable of expressing both light and heavy chains and secreting the monoclonal antibodies described herein into the medium in which the host cells are cultured. In some embodiments, the host cell is a hybridoma. Methods of producing anti-hPG monoclonal antibodies by culturing host cells are also provided.

Neutralizing anti-PG monoclonal antibodies, such as anti-hPG monoclonal antibodies, bind PG and block PG-dependent signaling, resulting in the inhibition of PG-induced responses in CRC tumor cells. Accordingly, also provided are methods of inhibiting PG-induced responses of CRC cells, which includes repression of cell differentiation, repression of cell death, and/or stimulation of cell proliferation. Generally, the method comprises contacting a CRC cell with, or exposing a cell population to, a neutralizing anti-PG monoclonal antibody in an amount effective to inhibit one or more PG-induced responses of CRC cells. The method can be carried out in vitro or in vivo, by administering a neutralizing anti-hPG monoclonal antibody to the environment containing CRC cells, which could be cell culture or in a tumor.

The neutralizing anti-PG monoclonal antibodies described herein inhibit PG-dependent proliferation of CRC tumor cells, making them useful therapeutic agents for the treatment of colorectal cancer. Accordingly, also provided are pharmaceutical compositions comprising a neutralizing anti-PG monoclonal antibody and methods of using the neutralizing anti-PG monoclonal antibodies and/or pharmaceutical compositions thereof to treat CRC. The pharmaceutical compositions can be formulated for any convenient route of administration, including, e.g., parenteral, subcutaneous or intravenous injection, and will typically include a neutralizing anti-hPG monoclonal antibody, and one or more acceptable carriers, excipients, and/or diluent suitable for the desired mode of administration, and can include other optional components as will be described further in the Detailed Description section. For therapeutic uses, the compositions can be packaged in unit dosage form for ease of use.

The treatment methods generally comprise administering to a subject in need of treatment, for example a subject diagnosed with CRC, an amount of a neutralizing anti-PG monoclonal antibody and/or pharmaceutical composition thereof effective to provide a therapeutic benefit. Therapeutic benefit, described below in more detail, includes any amelioration of CRC, for example, slowing or halting the progression of CRC, reducing the severity of CRC, inhibiting the growth of CRC tumors or the proliferation of CRC cells, reducing the size of CRC tumors, and/or reducing PG serum levels in CRC patients. The subject can be a human or non-human, including a domesticated animal (e.g., cat, dog, cow, pig, horse) or a non-domesticated animal. Preferably, the anti-PG monoclonal antibody is specific to the PG of the species being treated. For example, an anti-hPG antibody is administered to a human patient, an anti-dog PG antibody is administered to a canine patient, and the like. Subjects in whom anti-hPG monoclonal antibody therapy is useful can be: patients in any stage of disease progression (e.g., CRC Stage 0, I, II, III, or IV), patients who have received CRC therapy (e.g., chemotherapy, radiation therapy, surgical resection) or patients who are receiving other therapy for CRC.

Treatment with anti-PG monoclonal antibodies as described herein can be combined with, or adjunctive to, other therapy. Non-limiting examples of other therapy for CRC include chemotherapeutic treatment, radiation therapy, surgical resection, and antibody therapy, as described herein. In a specific example, anti-hPG monoclonal antibodies are administered in combination with chemotherapeutic agents. In another specific example, anti-hPG monoclonal antibodies are administered adjunctive to surgical resection. The anti-PG monoclonal antibodies can also be used in combination with one another.

Individuals with CRC tumors frequently have elevated levels of circulating PG (e.g., in serum or plasma). Accordingly, anti-hPG monoclonal antibodies can be used to detect PG levels for purposes of diagnosing CRC. Additionally, in patients already diagnosed with CRC, anti-hPG monoclonal antibodies can be used to select subjects suitable for receiving anti-PG therapy, or monitoring treatment efficacy. As disclosed herein, a method of diagnosing colorectal cancer in a subject comprises determining whether the amount of progastrin in a sample from the subject, for example a blood sample or a serum sample, measured using an anti-hPG monoclonal antibody according to the present disclosure, is above a threshold level. In a specific embodiment, the threshold level is 50 pM. In some embodiments, two anti-PG antibodies are used, one that recognizes a C-terminal region of PG and another that recognizes an N-terminal region of PG. In this embodiment, one or both of the N-terminal or C-terminal antibodies is an anti-PG monoclonal antibody as described herein. Preferably, N-terminal and C-terminal anti-PG monoclonal antibodies are used. The antibodies may be, but need not be, neutralizing.

For purposes of monitoring treatment efficacy, anti-PG monoclonal antibodies can be used to determine whether the level of progastrin is decreasing over time in samples from a subject who has been or is being treated for CRC by comparing the amount of PG in samples taken at different times. The specific embodiments of anti-PG antibodies described in the preceding paragraph can also be used in this assay.

Also provided are kits suitable for carrying out the various diagnostic, monitoring, and other methods described herein. Such kits will typically comprise an anti-PG monoclonal antibody as described herein and, optionally, additional anti-PG antibodies and/or reagents suitable for performing the specific assay. In some embodiments, one or more anti-PG antibodies included in the kit is labeled with a detectable label, such as a fluorophore. In a specific embodiment, the kit includes an anti-PG antibody that specifically binds an N-terminal region of PG, an anti-PG antibody that specifically binds a C-terminal region of PG and optionally, reagents suitable for performing a diagnostic assay, where the N-terminal specific antibody is an N-terminal anti-PG monoclonal antibody as described herein and/or the C-terminal specific antibody is a C-terminal anti-PG monoclonal antibody as described herein.

The features and advantages of the various inventions described herein will become further apparent from the following detailed description of exemplary embodiments thereof.

8. BRIEF DESCRIPTION OF THE FIGURES

FIG. 1 provides amino acid sequences of pre-progastrin (wherein the signal peptide is underlined) (SEQ ID NO:100), progastrin (SEQ ID NO:20) and products of progastrin processing including G34 (SEQ ID NO:101), G34-Gly (SEQ ID NO:102), G17 (SEQ ID NO:103), G17-Gly (SEQ ID NO:104), and C-terminal flanking peptide, CTFP (SEQ ID NO:105).

FIGS. 2A-2L provide polypeptide, and corresponding polynucleotide, sequences of $V_H$ and $V_L$ chains for exemplary murine anti-hPG monoclonal antibodies: anti-hPG MAb 3 (SEQ ID NOs:16, 12, 17 and 13, respectively, in order of appearance) (FIG. 2A, FIG. 2B), anti-hPG MAb 4 (SEQ ID NOs:18, 14, 19 and 15, respectively, in order of appearance) (FIG. 2C, FIG. 2D), anti-hPG MAb 8 (SEQ ID NOs:67, 59, 71 and 63, respectively, in order of appearance) (FIG. 2E, FIG. 2F), anti-hPG Mab 13 (SEQ ID NOs:68, 60, 72 and 64, respectively, in order of appearance) (FIG. 2G, FIG. 2H), anti-hPG MAb 16 (SEQ ID NOs:69, 61, 73 and 65, respectively, in order of appearance) (FIG. 2I, FIG. 2J), and anti-hPG MAb 19 (SEQ ID NOs:70, 62, 74 and 66, respectively, in order of appearance) (FIG. 2K, FIG. 2L), in which the three CDRs of each chain are underlined.

Figure 3B:
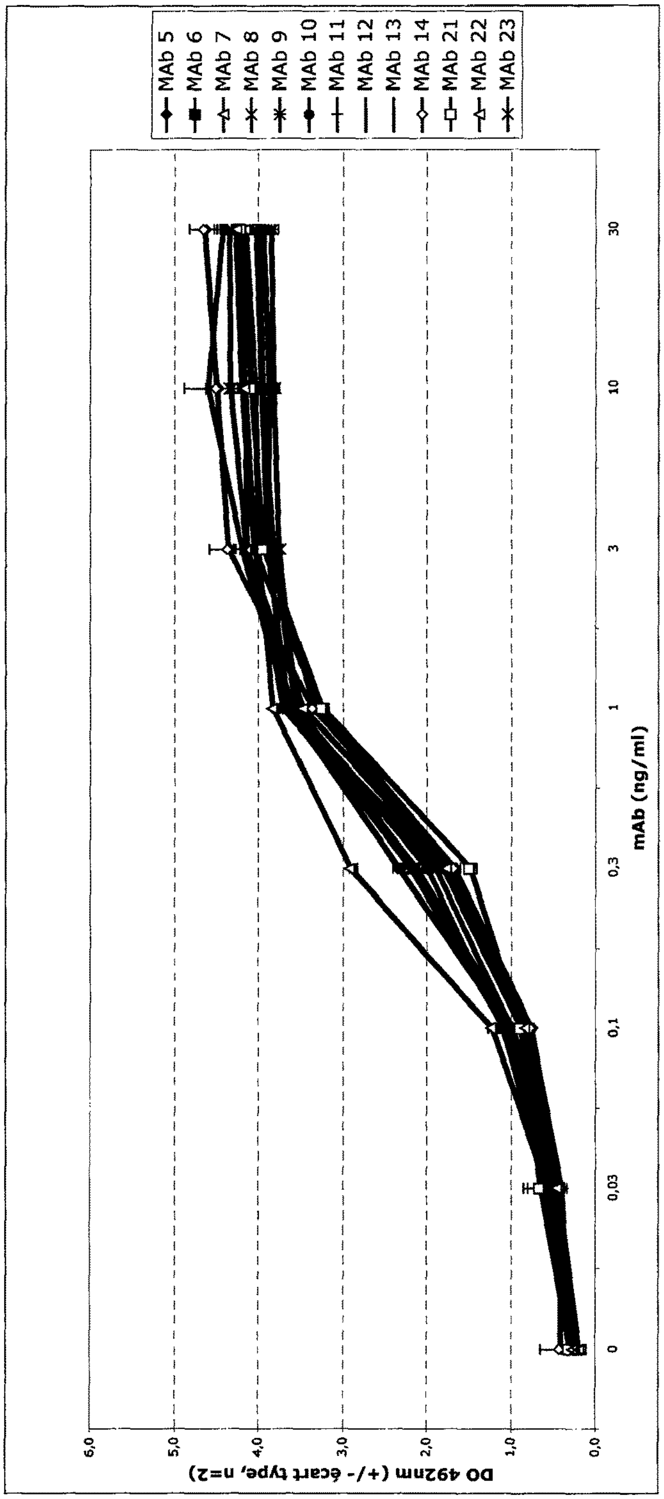
Figure 3C:
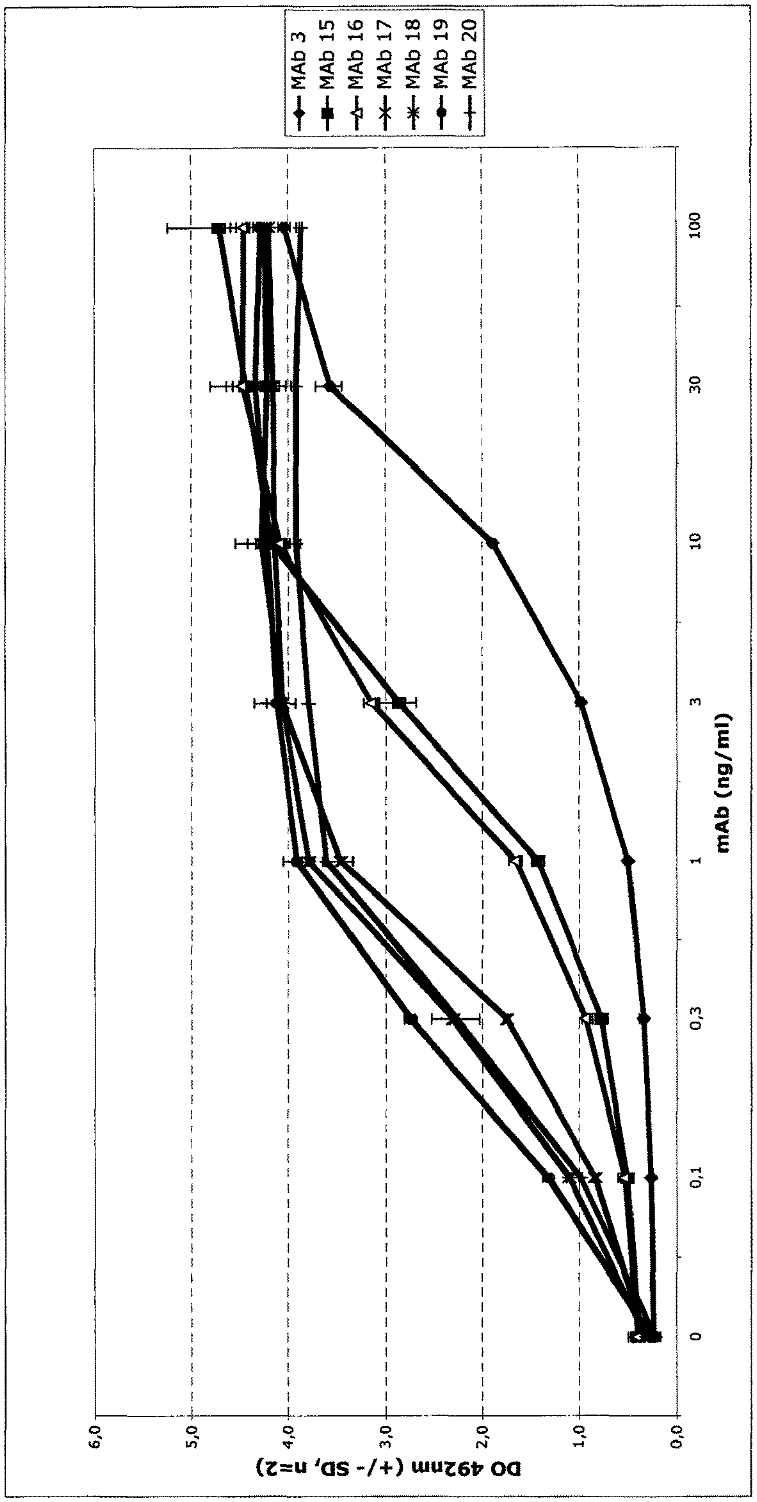

FIGS. 3A-3C provide graphs illustrating relative binding affinities (measured as absorbance at 492 nm) at increasing antibody concentrations (μg/mL) of exemplary murine anti-hPG monoclonal antibodies, MAbs 1-4 (FIG. 3A); MAbs 5-14 and 20-23 (FIG. 3B); and MAbs 3 and 15-19 (FIG. 3C).

Figure 4:
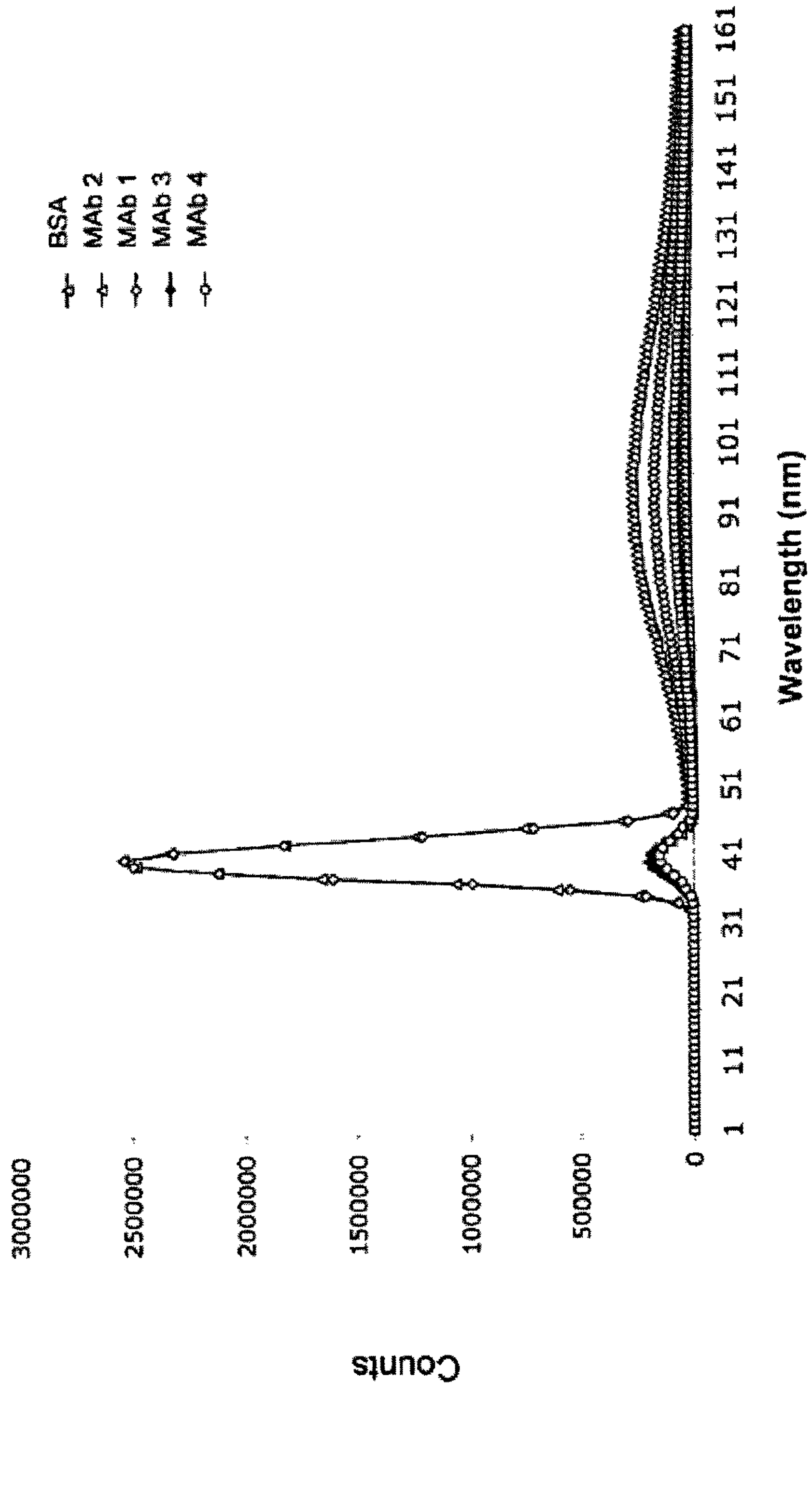

FIG. 4 provides a graph illustrating the ratio of absorbance (optical density) at 280 nm and 330 nm for four different exemplary murine anti-hPG monoclonal antibodies as compared to a control sample of bovine serum albumin (arbitrary units).

Figure 5A:
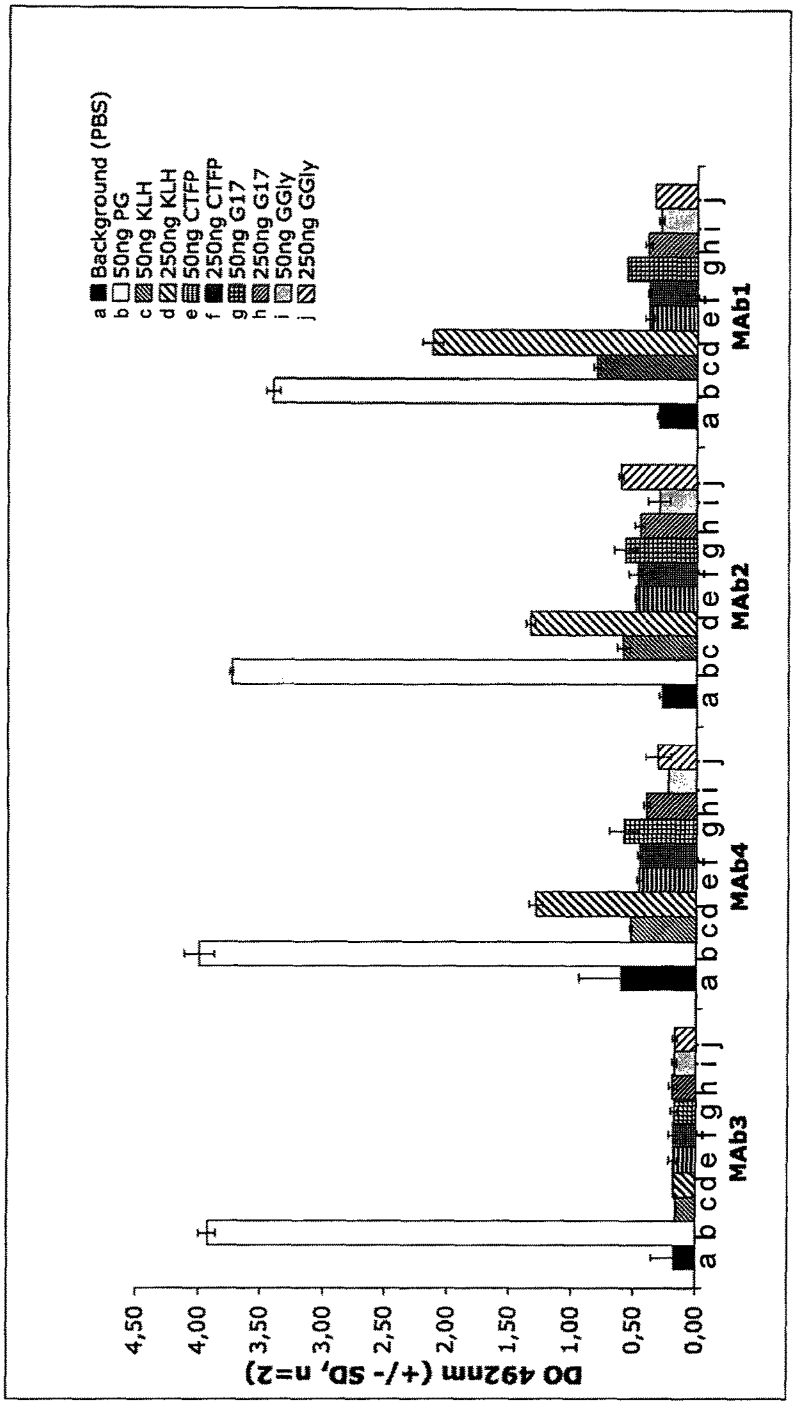
Figure 5B:
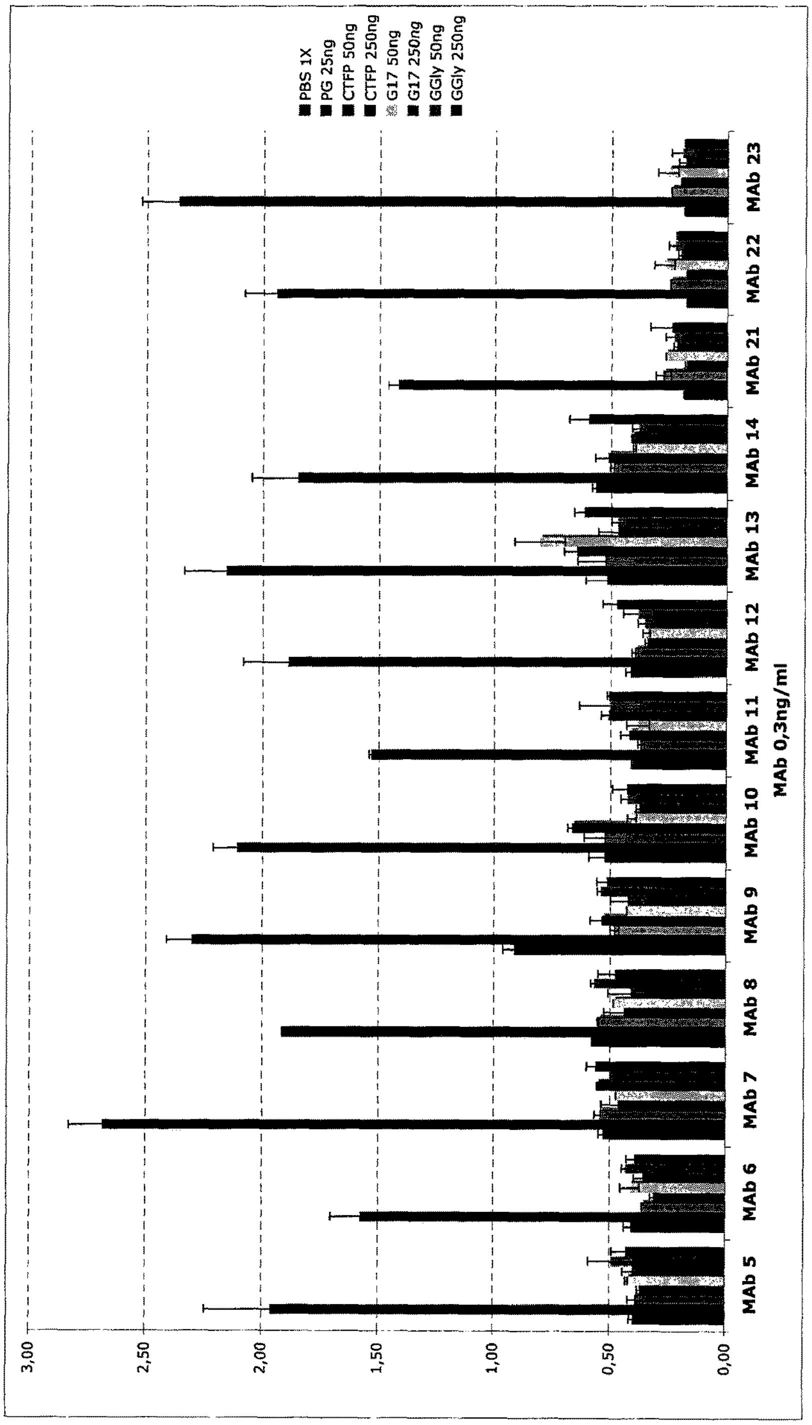
Figure 5C:
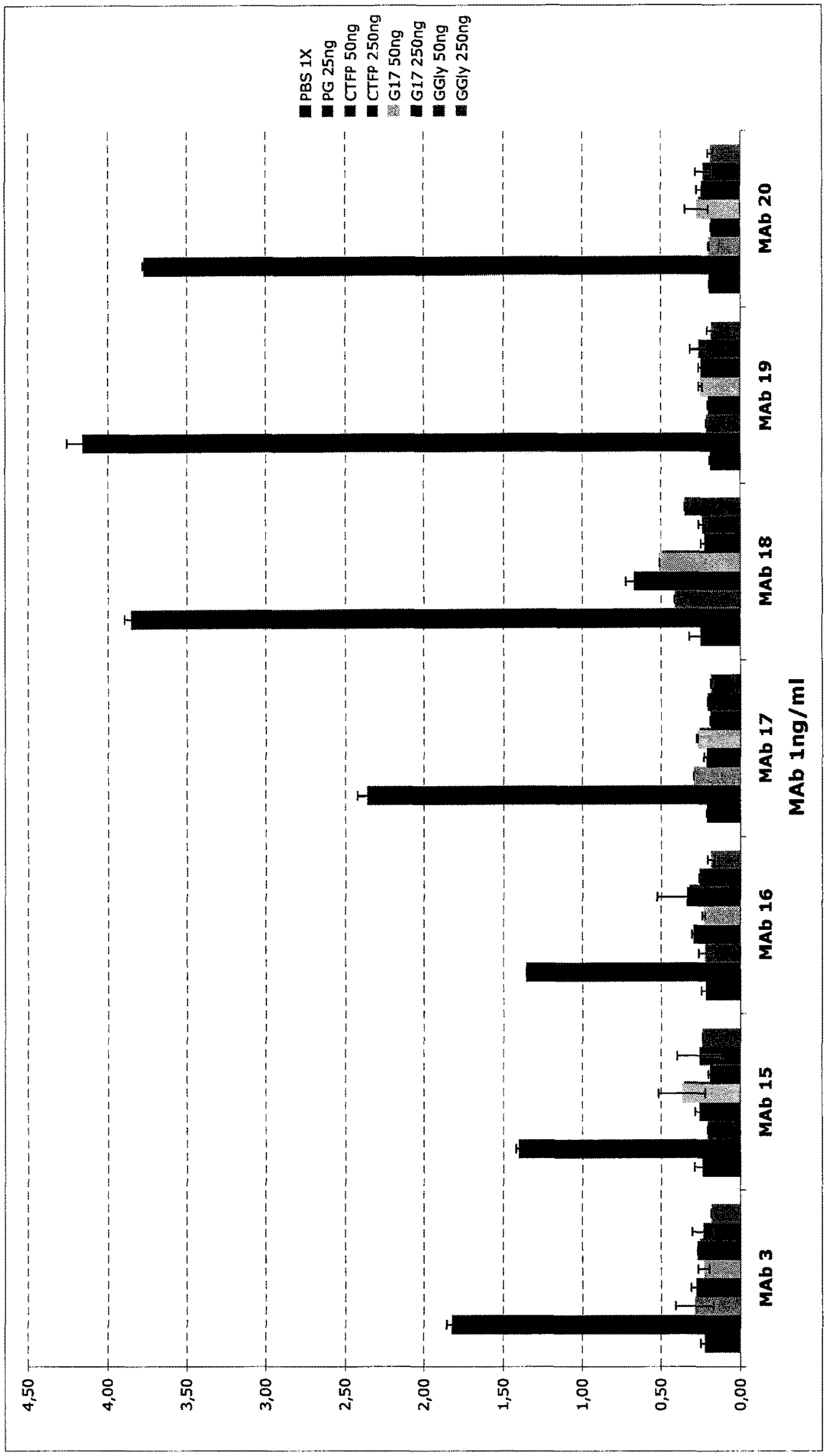

FIGS. 5A-5C provide graphs illustrating the binding of 23 different exemplary murine anti-hPG monoclonal antibodies to 25 or 50 ng hPG as compared to: buffer alone (negative control), 250 ng KLH (negative control), and peptides derived from the gastrin gene (50 and 250 ng of CTFP, G17, or G17-Gly (referred to in the figure as "G-Gly"), as indicated. FIG. 5A shows the binding of anti-hPG MAbs 1-4, FIG. 5B shows the binding of anti-hPG MAbs 5-14 and 21-23, and FIG. 5C shows the binding of anti-hPG MAbs 3 and 15-20.

Figure 6:
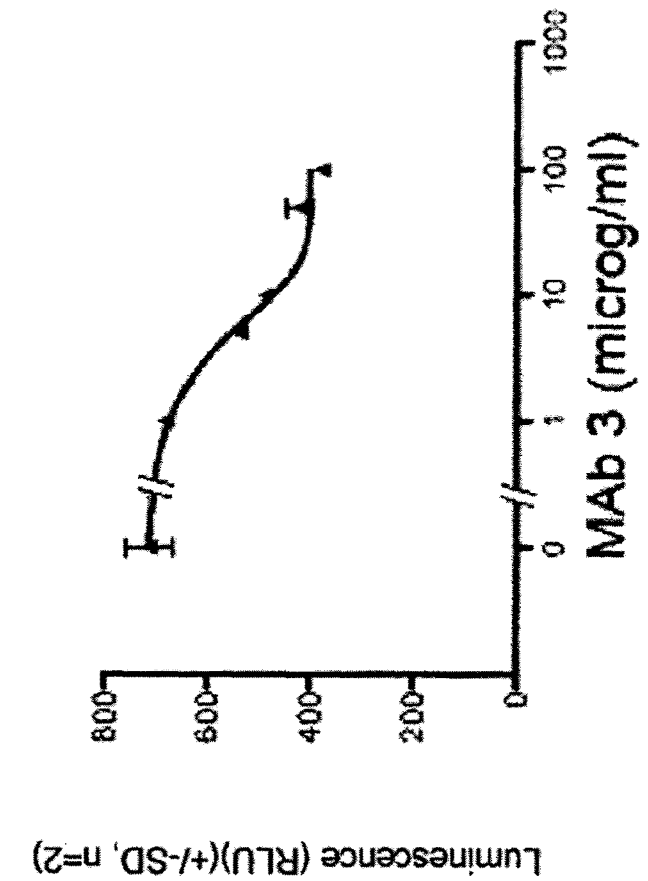

FIG. 6 provides a graph illustrating the binding of a polyclonal anti-hPG antibody that binds an N-terminal region of hPG at increasing concentrations of anti-hPG MAb3.

Figure 7A:
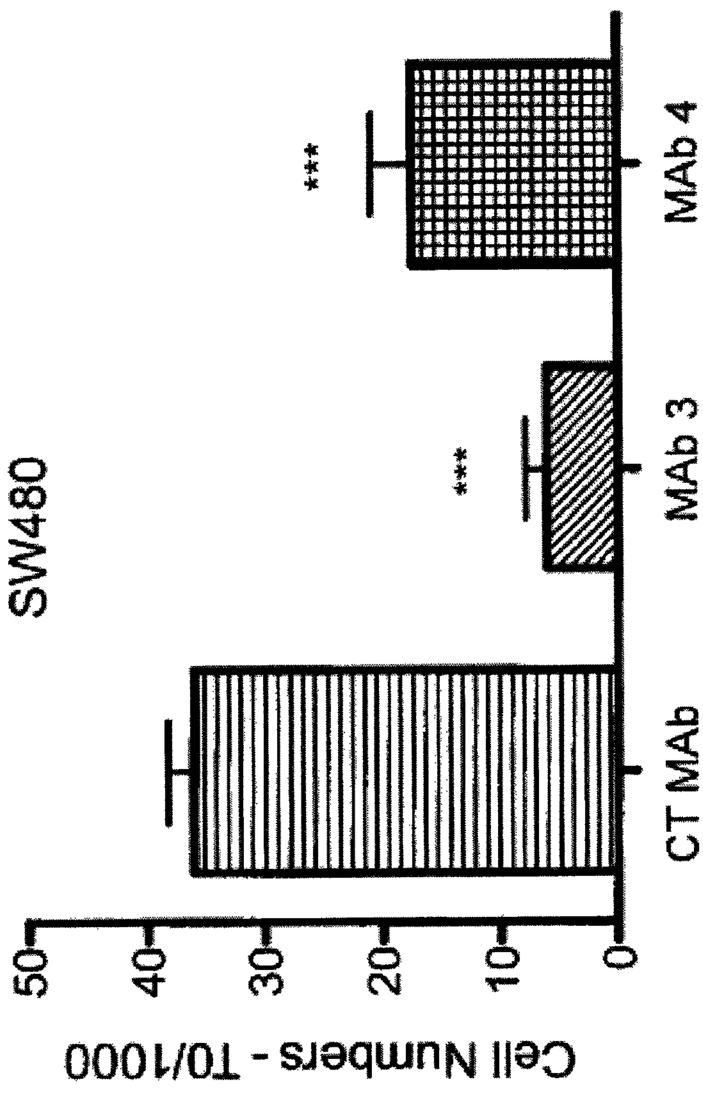
Figure 7B:
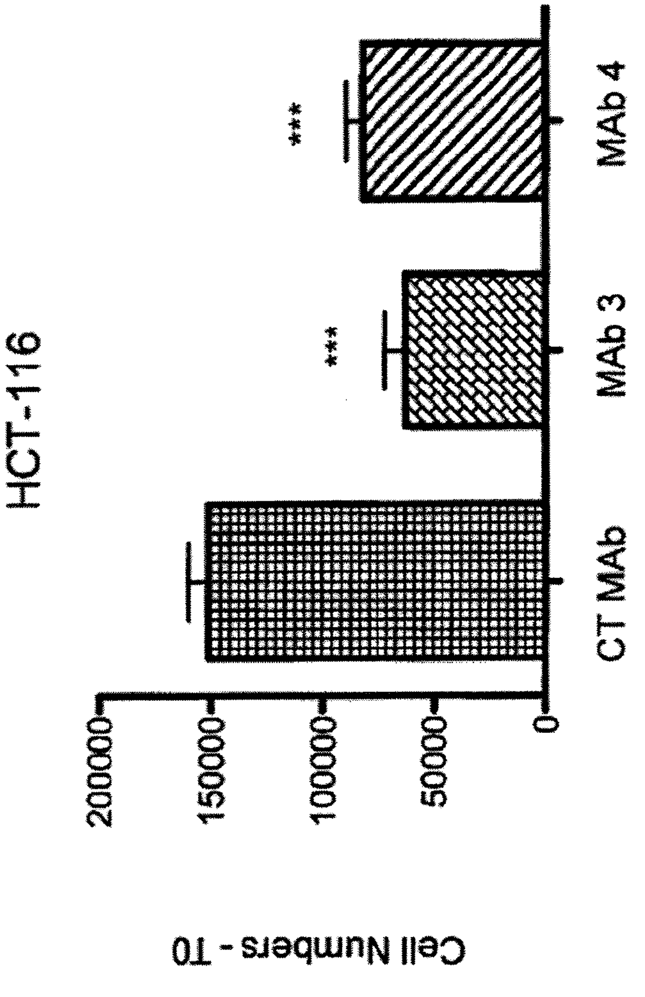
Figure 7C:
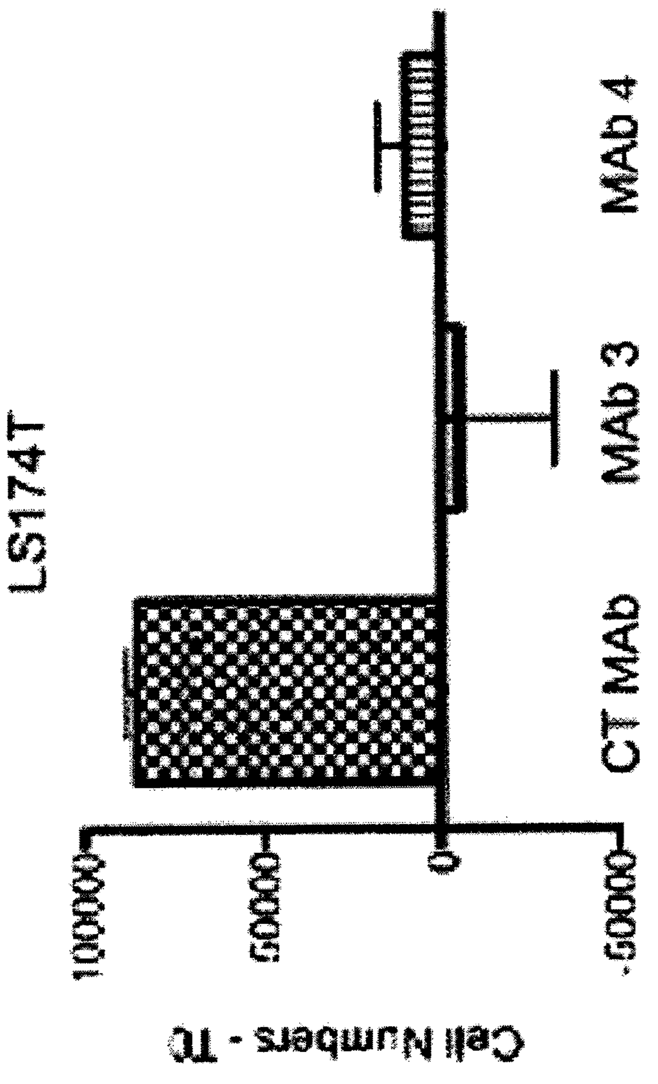
Figure 7D:
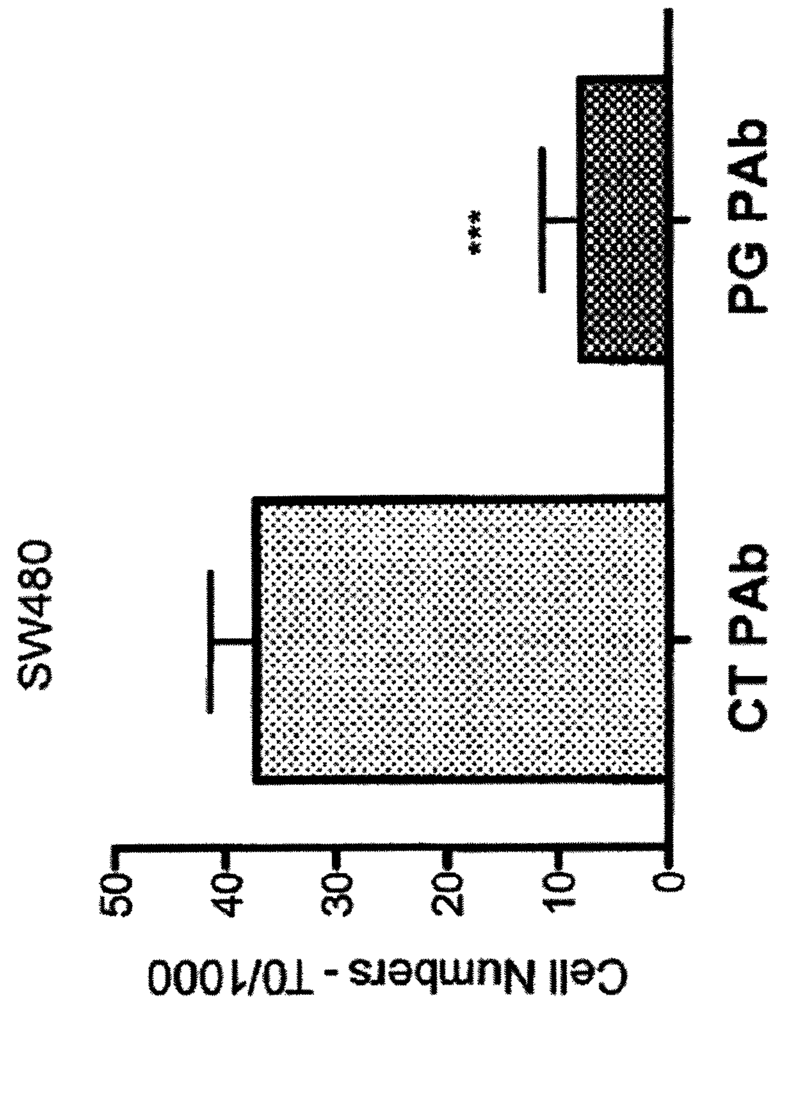
Figure 7E:
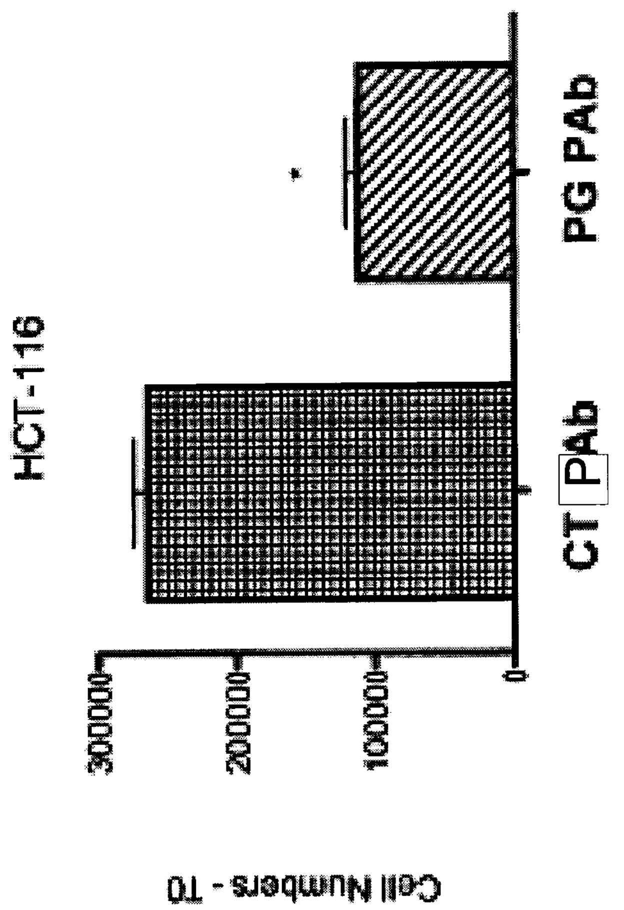
Figure 7F:
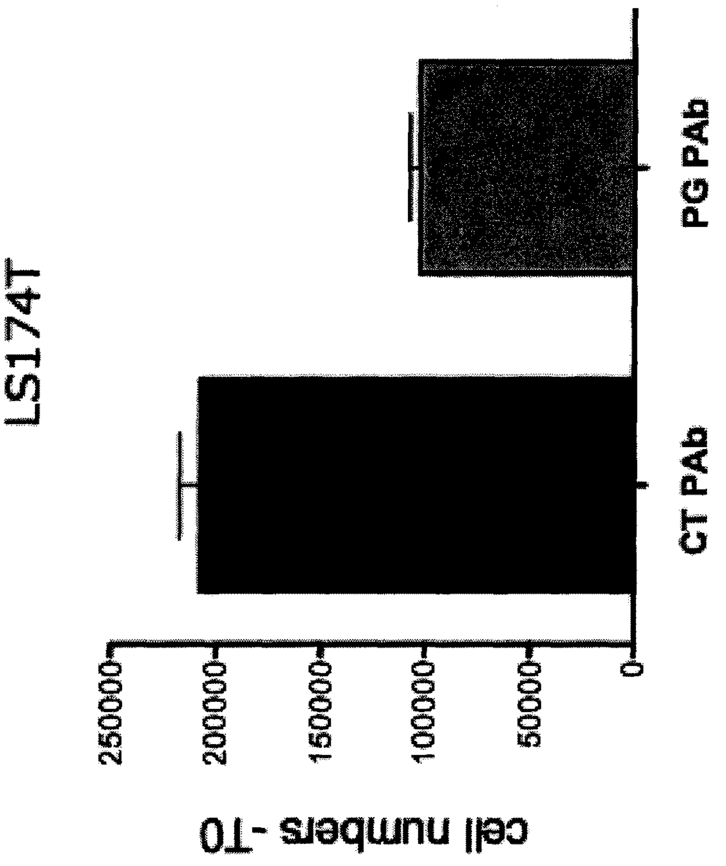
Figure 7G:
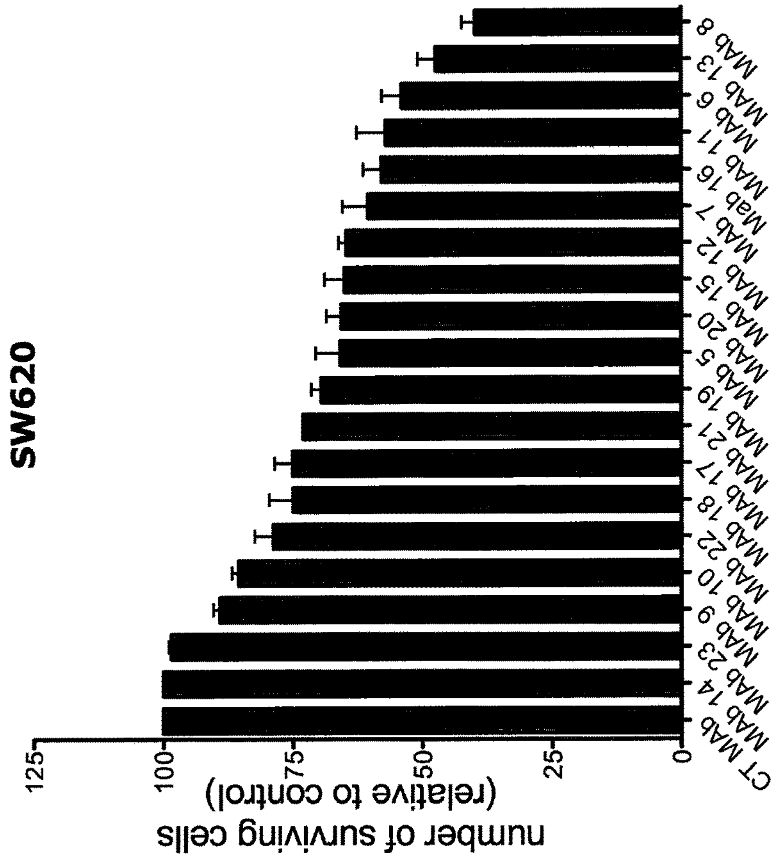
Figure 7H:
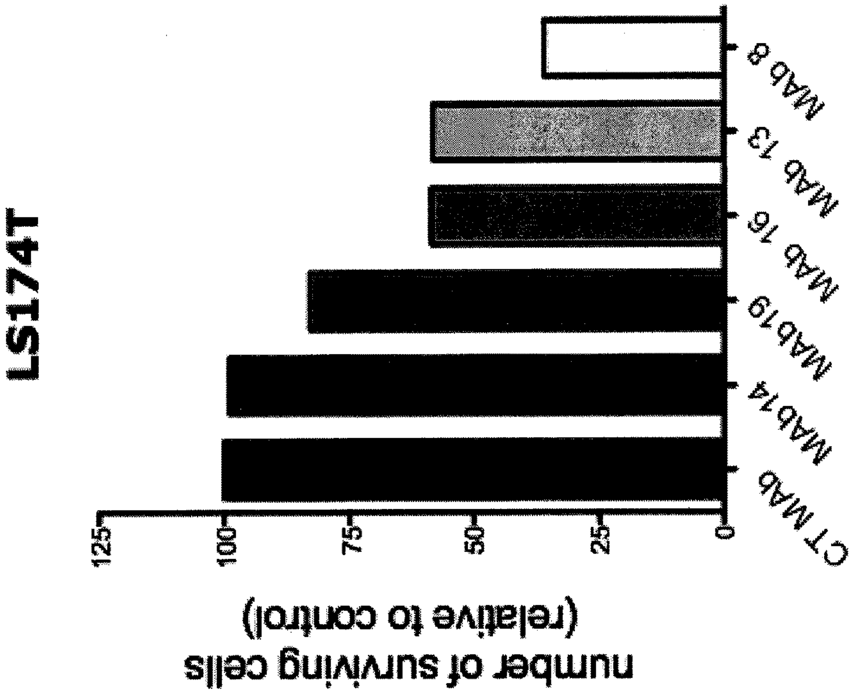
Figure 7I:
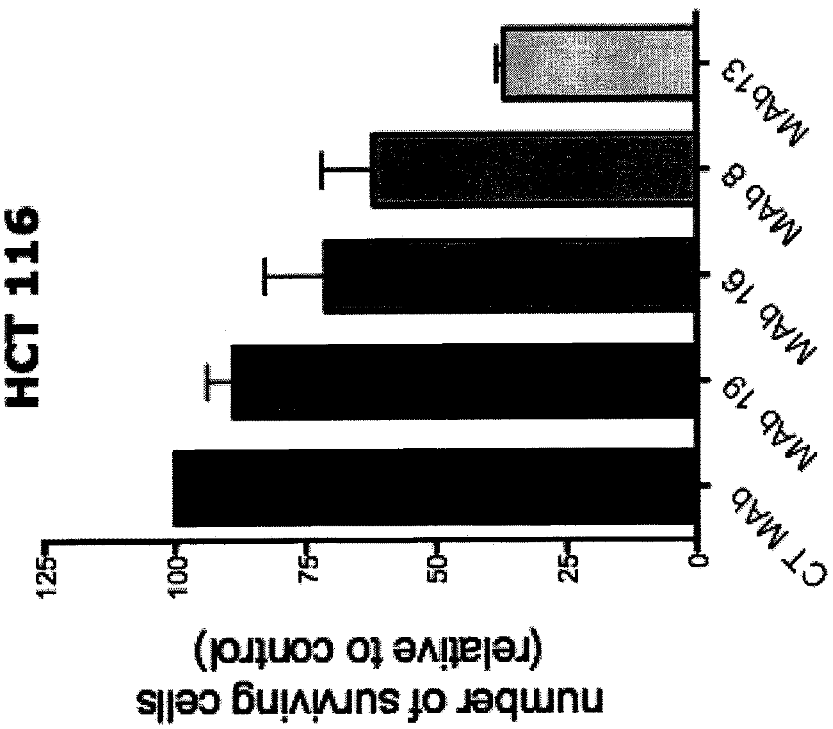

FIGS. 7A-7I provide graphs illustrating proliferation of representative CRC cell lines treated with anti-hPG monoclonal antibodies as follows: SW480, HCT-116, LS174T, as indicated, treated with exemplary anti-hPG monoclonal antibodies MAb 3 and MAb 4 (FIG. 7A, FIG. 7B, and FIG. 7C, respectively, showing the change in number of live cells at the end of treatment relative to the beginning of treatment (T0) with the indicated antibody), or an anti-hPG polyclonal antibody (FIG. 7D, FIG. 7E, and FIG. 7F, respectively, showing the change in number of live cells at the end of treatment relative to the beginning of treatment (T0) with antibody); proliferation of CRC cell line SW620 treated with anti-hPG MAb 5 to MAb 23 (FIG. 7G, showing live anti-hPG-treated cells as a percentage of the number of control antibody-treated cells at the end of treatment relative to the beginning of treatment (T0)); proliferation of LS174T cells treated with anti-hPG MAb 8, 13, 14, 16, and 19 (FIG. 7H, showing live anti-hPG-treated cells as a percentage of the number of control antibody-treated cells at the end of treatment relative to the beginning of treatment (T0)); and proliferation of HCT-116 cells treated with anti-hPG monoclonal antibodies MAb 8, 13, 14, 16, 19 (FIG. 7I, showing live anti-hPG-treated cells as a percentage of the number of control antibody-treated cells at the end of treatment relative to the beginning of treatment (T0)).

Figure 8:
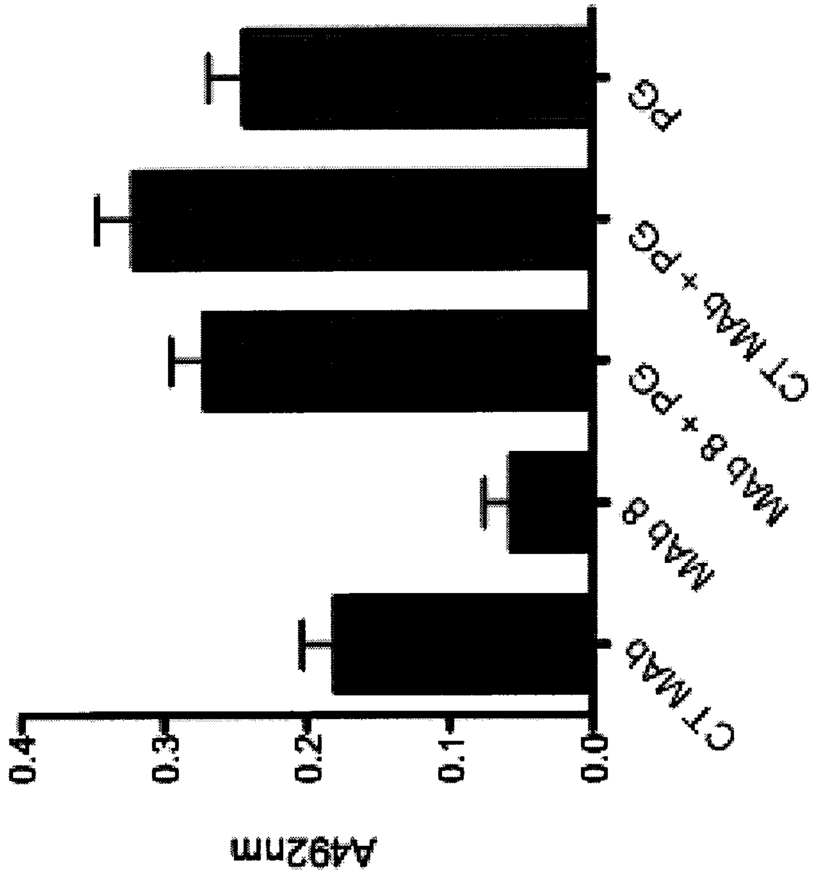

FIG. 8 provides a graph illustrating the number of live LS174T cells at 48 hours after 4 treatments with a control monoclonal antibody, anti-hPG MAb 8 (5 μg/mL), anti-hPG MAb 8 pre-incubated with hPG, the control antibody pre-incubated with hPG, or hPG alone.

Figure 9A:
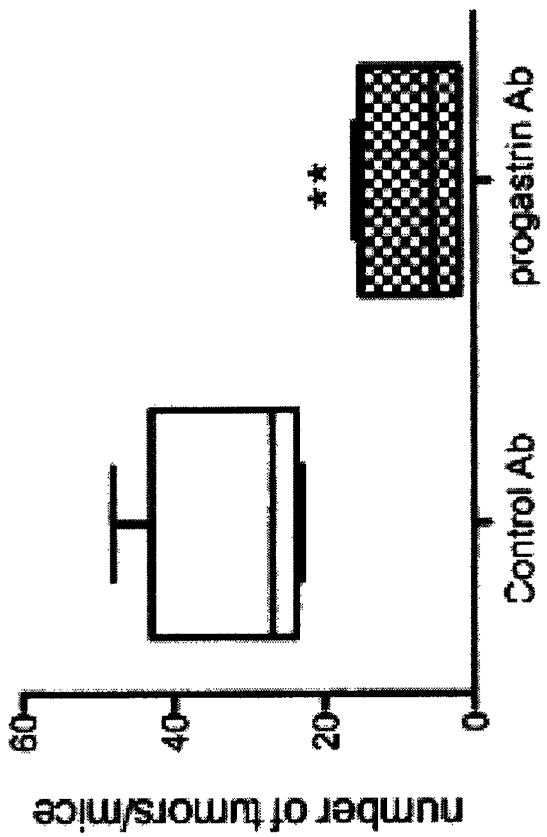
Figure 9B:
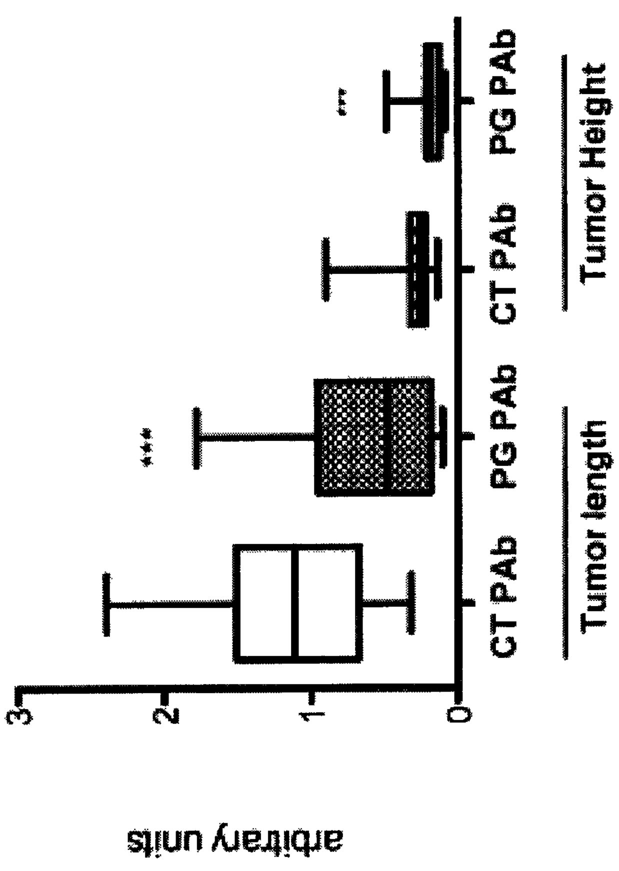

FIGS. 9A-9B provide graphs illustrating the number of tumors per mouse (FIG. 9A) and average tumor length and height (FIG. 9B) in mice treated with anti-hPG antibodies as compared to a control polyclonal antibody.

9. DETAILED DESCRIPTION OF EXEMPLARY EMBODIMENTS

9.1. Detailed Description

Progastrin (PG) was first identified as the precursor to gastrin, a gut peptide hormone that stimulates gastric acid secretion. Gastrin exists in a number of different molecular forms (G17, G34, glycine-extended G17, glycine-extended G34) derived from progastrin. See FIG. 1. The gastrin gene encodes a 101-amino acid product, preprogastrin. A first cleavage removes a 21-amino-acid residue signal peptide (underlined in FIG. 1) and results in PG, an 80 amino acid peptide. The understood, known polypeptide sequence of human PG (hPG) is provided in SEQ ID NO:20. As illustrated in FIG. 1, the amino acid residues of hPG are numbered from 1 to 80, with the amino-most residue being position 1. Sequences within the first 40 amino acids of progastrin are referred to as "N-terminal," while sequences falling within residue 41 to 80 are referred to as "C-terminal."

Recent studies have shown that progastrin levels are elevated in patients with CRC. Under normal physiological conditions, progastrin accounts for less than 10% of total secreted peptide in humans. In colorectal cancer, progastrin levels are significantly elevated in both plasma and tumor tissue, possibly as a result of increased expression of the gastrin gene coupled with incomplete processing of the gene product. One study showed significantly higher serum progastrin levels in CRC patients as compared to control patients but no such difference for the more processed forms of gastrin (Siddheshwar et al., 2001, *Gut* 48:47-52). In CRC tumor samples tested, 80-100% of samples showed increased PG levels. See, e.g., Ciccotosto et al., 1995, *Gastroenterology* 109:1142-1153; Baldwin et al., 1998, *Gut* 42:581-584; Van Solinge, 1993, *Gastroenterology* 104: 1099-1107. The role of PG in CRC has been further substantiated by experiments showing that mice expressing recombinant human PG treated with the carcinogen azoxymethane had significantly greater numbers of aberrant crypt foci, adenomas, and adenocarcinomas in the colon as compared to wild type mice or mice expressing amidated gastrins (Singh et al. 2000, *Gastroenterology* 119:162-171).

Recently, Hollande et al., demonstrated that progastrin stimulates the beta-catenin/Tcf4 pathway by repressing ICAT, a negative regulator of beta-catenin/Tcf4 signaling, and that blocking progastrin leads to de novo expression of ICAT. See WO 2007/135542. While not intending to be bound by any theory of operation, it is believed that blocking progastrin signaling leads to repression of beta-catenin/Tcf4-induced proliferation as a result of increased ICAT expression. In the absence of continued PG-dependent signaling, cell proliferation is inhibited, and cell differentiation and/or cell death (including apoptosis) is triggered.

Despite the urgent need for new clinical approaches to the treatment and diagnosis of CRC, the evidence that PG stimulates proliferation of CRC tumor cells, and despite the increased focus on monoclonal antibody therapies in the treatment of cancer, to date, there are no reports demonstrating any monoclonal antibody capable of blocking PG-dependent tumor cell proliferation, or even binding PG. Such antibodies, presented herein for the first time, proved difficult to develop. As a first challenge, applicants found that recombinant human progastrin, which can be used to generate polyclonal anti-hPG antibodies, failed to induce a monoclonal immunogenic response in test mice. Therefore, it was necessary to design immunogens using only peptide fragments of PG to generate antibodies specific to progastrin and not other gastrin gene products. Even once hybridoma clones yielded antibodies that bound the antigenic peptide, it was found that binding to the peptide was not predictive of the ability to bind PG, specifically or at all. As shown in more detail in the Examples below, many hybridomas yielded antibodies that bound the PG antigen peptide used in the immunogen but failed to bind PG. The present disclosure provides anti-hPG monoclonal antibodies that bind not only the peptide antigen against which they were raised but also that bind hPG specifically. Quite surprisingly, monoclonal antibodies highly specific for hPG relative to its processing products (e.g., G34, G34-Gly, G17, G17-Gly, CTFP) were obtained with antigens that in some cases are not unique to hPG, but that included regions of amino acid sequence common to one or more of the progatrin processing products. Moreover, it was also surprisingly discovered that despite the relatively small size of hPG (80 amino acids) not all anti-hPG monoclonal antibodies, even those exhibiting a high degree of affinity and specificity for hPG, neutralize its biological activity.

Anti-hPG Monoclonal Antibodies

Applicants have discovered peptide antigens useful for raising anti-hPG monoclonal antibodies. Peptides useful for raising anti-hPG antibodies of the present disclosure comprise progastrin-specific sequences not found in the more processed forms of the polypeptide, such as glycine-extended or amidated gastrins or CTFP, but can also comprise sequences that are found in processed forms of hPG. In some embodiments, anti-hPG monoclonal antibodies are raised against a peptide antigen having an amino acid sequence corresponding to an N-terminal region of hPG and are designated N-terminal anti-hPG monoclonal antibodies. A specific exemplary antigenic region that can be used to construct an immunogen useful for obtaining N-terminal anti-PG monoclonal antibodies corresponds to residues 1 to 14 of hPG (SWKPRSQQPDAPLG (SEQ ID NO: 25)) coupled to a linker sequence. In other embodiments, the anti-hPG monoclonal antibodies are raised against a peptide antigen having an amino acid sequence corresponding to a C-terminal region of hPG and are designated C-terminal anti-hPG monoclonal antibodies. A specific exemplary antigenic region that can be used to construct an immunogen useful for obtaining C-terminal anti-PG monoclonal antibodies corresponds to residues 55 to 80 of hPG (SEQ ID NO:27) coupled to a linker sequence. See Table 1.

Anti-PG monoclonal antibodies of the present disclosure bind PG and are useful for detecting and isolating PG from complex mixtures. Additionally, the anti-PG monoclonal antibodies of the disclosure are uniquely suited to therapeutic and/or diagnostic applications for colorectal cancer. In various embodiments, anti-hPG monoclonal antibodies (1) specifically bind PG versus other gastrin gene products, (2) have high affinity to hPG, (3) inhibit colorectal cancer cell proliferation in vitro and in vivo, (4) reduce tumor size and number in vivo, (5) detect PG in complex mixtures containing other gastrin-gene derived peptides.

The gastrin gene is expressed and extensively processed, to yield several protein products that have roles in normal homeostasis. Progastrin, on the other hand, is typically not detectable in the circulation of healthy subjects. The monoclonal antibodies of the present disclosure are intended to target progastrin but not other peptides derived from the gastrin gene. Accordingly, anti-hPG monoclonal antibodies specifically bind to progastrin, from humans and other animals, but not to other gastrin gene products, such as, but not limited to, glycine-extended or amidated gastrins, or C-terminal Flanking Peptide (CTFP).

Specificity of anti-hPG monoclonal antibodies can be determined using an ELISA as follows. 96-well plates are incubated overnight at 4° C. with appropriate concentration(s) of test polypeptide (e.g., 25 and 50 ng recombinant human PG, and 50 and 250 ng CTFP or other gastrin-derived gene products) in Phosphate-Buffered Saline (PBS), after which the wells are washed three times with wash solution (PBS and 0.1% TWEEN®-20), and then incubated for 2 hours at 22° C. with 100 μL blocking solution (PBS, 0.1% TWEEN®-20, 0.1% Bovine Serum Albumin or casein hydrolysate) per well. After blocking, the wells are washed three times and the antibody to be assayed (test antibody) is added. 100 μL of the test antibody (at 0.3 to 1 ng/mL) in PBS and 0.1% TWEEN®-20 are added to each well. Plates are then incubated for 2 hours at 22° C., after which the test antibody solution is discarded and replaced, after a wash step (3×100 wash solution, as noted above), with blocking solution containing a secondary antibody, a goat anti-mouse IgG (Fc) antibody coupled to horseradish peroxidase. After a 1-hour incubation with secondary antibody, 100 μL of substrate solution (e.g. Fast OPD, or O-Phenylenediamine dihydrochloride, available from Sigma-Aldrich Co., prepared according to manufacturer's directions) is added to each well and incubated in the dark for 20 minutes at 22° C. The reaction is stopped by adding 50 μL of 4N sulfuric acid and the amount of substrate catalyzed determined by measuring the optical density (O.D.) at 492 nm. Substrate conversion is proportional to the amount of primary (test) antibody bound to the antigen. Experiments are run in duplicate and OD measurements plotted as a function of antigen concentration. Test antibodies are scored as specific for PG if the measured O.D. is between 0.2 and 1.5 for hPG and there is no statistically significant signal above background with CTFP or any of the other gastrin-gene derived peptides, where the background is the average signal from control wells containing only PBS.

Several anti-hPG monoclonal antibodies of the present disclosure were found to be highly specific. In some embodiments, anti-hPG monoclonal antibodies exhibit 100-fold greater specificity for progastrin as compared to the other gastrin gene products. In such embodiments, 100-fold more antigen (e.g., glycine-extended or amidated gastrin) is required to yield the same binding as is observed when the antigen is progastrin.

Other methods for determining binding include, but are not limited to, an immunofluorescent method, an enzyme-linked immunosorbent assay (ELISA), a radioactive material labeled immunoassay (RIA), a sandwich ELISA (Monoclonal Antibody Experiment Manual (published by Kodansha Scientific, 1987), Second Series Biochemical Experiment Course, Vol. 5, Immunobiochemistry Research Method, published by Tokyo Kagaku Dojin (1986)).

Anti-hPG monoclonal antibodies with high affinity for PG are desirable for both therapeutic and diagnostic uses. For certain uses, such as therapeutic uses, an affinity of at least about 100 nM is desirable, although antibodies having greater affinities, for example affinities of at least about 90 nM, 80 nM, 70 nM, 60 nM, 50 nM, 40 nM, 30 nM, 25 nM, 20 nM, 15 nM, 10 nM, 7 nM, 6 nM, 5 nM, 4 nM, 3 nM, 2 nM, 1 nM, 0.1 nM, 0.01 nM, 10 pM, 1 pM, or even greater, may be desirable. In some embodiments, the monoclonal antibodies specifically bind hPG with an affinity in the range of about 1 pM to about 100 nM, or an affinity ranging between any of the foregoing values.

Affinity of anti-hPG monoclonal antibodies for hPG can be determined using techniques well known in the art or described herein, such as for example, but not by way of limitation, ELISA, isothermal titration calorimetry (ITC), BIACORE®, Proteon, or fluorescent polarization assay.

Using antigens from N- or C-terminal regions of hPG, antibodies that recognize different epitopes of hPG can be generated. The epitope recognized by a monoclonal antibody will depend on the particular antigen used to raise the antibody and can be mapped using techniques known to the skilled artisan, such as alanine scanning and SPOT® analysis (see Examples section below). For example, epitope mapping reveals that anti-hPG MAb 2 and MAb 4 bind the same epitope; anti-hPG MAb 1 and MAb 3 bind approximately the same epitope; MAb 17, MAb 18, MAb 19, and MAb 20 bind approximately the same epitope; MAb 15 and MAb 16 bind approximately the same epitope; anti-hPG MAb 5, MAb 6, MAb 7, MAb 9, and MAb 12 bind the same epitope and bind approximately the same epitope as anti-hPG MAb 10; and anti-hPG MAb 11 and MAb 14 bind approximately the same epitope.

Whether or not an anti-hPG monoclonal antibody recognizes a particular epitope can be determined using a competition assay as described herein, in which the epitope bound by the reference antibody is known. In some embodiments, the anti-hPG monoclonal antibody competes with a reference antibody which binds an epitope having an amino acid sequence corresponding to an N-terminal region of hPG. In specific embodiments, anti-hPG monoclonal antibodies compete with a reference antibody that binds an epitope that includes residues 10 to 14 of hPG (SEQ ID NO:28), residues 9 to 14 of hPG (SEQ ID NO:29), residues 4 to 10 of hPG (SEQ ID NO:30), residues 2 to 10 of hPG (SEQ ID NO:31), or residues 2 to 14 of hPG (SEQ ID NO:32). In some embodiments, the anti-hPG monoclonal antibody competes with a reference antibody which binds an epitope having an amino acid sequence corresponding to a C-terminal region of hPG. In specific embodiments, anti-hPG monoclonal antibodies compete with a reference antibody that binds an epitope that includes residues 71 to 74 of hPG (SEQ ID NO:33), residues 69 to 73 of hPG (SEQ ID NO:34), residues 76 to 80 of hPG (SEQ ID NO:35), or residues 67 to 74 of hPG (SEQ ID NO:36).

The anti-PG monoclonal antibodies can be neutralizing. While not intending to be bound by any theory of operation, through binding of PG, neutralizing anti-hPG monoclonal antibodies are thought to block or inhibit its ability to interact with its signaling partner(s). This, in turn, inhibits a signal transduction pathway in colorectal tumor cells that would otherwise lead to proliferation, reduced cell differentiation and cell death. In some embodiments, neutralizing anti-PG monoclonal antibodies bind an N-terminal region of hPG. In specific embodiments, neutralizing anti-PG monoclonal antibodies compete for binding PG with anti-hPG MAb1, MAb2, MAb3, MAb4, MAb15, MAb16, MAb17, MAb18, MAb19, or MAb20. In other embodiments, neutralizing anti-PG monoclonal antibodies bind a C-terminal region of hPG. In specific embodiments, neutralizing anti-PG monoclonal antibodies compete for binding PG with anti-hPG MAb5, MAb6, MAb7, MAb8, MAb9, MAb10, MAb11, MAb12, MAb13, MAb21, MAb22, or MAb23.

A specific test for whether an anti-PG monoclonal antibody is neutralizing can be performed as follows. CRC LS174T cells are seeded in a 6-well plate, as described in Example 7 below, at approximately 50,000 cells per well. Cells are then treated at 12 hour intervals for 48 hours with the test anti-PG monoclonal antibody or a control monoclonal antibody as noted in Example 7, at antibody concentrations of about 5 μg/mL. A test antibody is defined as neutralizing in the assay, if the number of CRC cancer cells treated with the test antibody shows a statistically significant reduction of at least 10% in the number of surviving cells compared to the number of cells treated with a control, non-specific antibody, using a two-tailed Mann-Whitney test (with differences considered as significant when $p<0.05$). Total cell numbers are corrected for the number of cells at the start of the treatment period, referred to as T0.

As used herein, an antibody (Ab) refers to an immunoglobulin molecule that specifically binds to, or is immunologically reactive with, a particular antigen, and includes polyclonal, monoclonal, genetically engineered and otherwise modified forms of antibodies, including but not limited to chimeric antibodies, humanized antibodies, and antigen binding fragments of antibodies, including e.g., Fab', F(ab')$_2$, Fab, Fv, rIgG, and scFv fragments. In various embodiments, anti-hPG monoclonal antibodies comprise all or a portion of a constant region of an antibody. In some embodiments, the constant region is an isotype selected from: IgA (e.g., IgA1 or IgA2), IgD, IgE, IgG (e.g., IgG1, IgG2, IgG3 or IgG4), and IgM.

The term "monoclonal antibody" as used herein is not limited to antibodies produced through hybridoma technology. A monoclonal antibody is derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof. In many uses of the present disclosure, including in vivo use of the anti-hPG monoclonal antibodies in humans and in vitro detection assays, chimeric, primatized, humanized, or human antibodies can suitably be used.

The term "scFv" refers to a single chain Fv antibody in which the variable domains of the heavy chain and the light chain from a traditional antibody have been joined to form one chain.

References to "$V_H$" refer to the variable region of an immunoglobulin heavy chain of an antibody, including the heavy chain of an Fv, scFv, or Fab. References to "$V_L$" refer to the variable region of an immunoglobulin light chain, including the light chain of an Fv, scFv, dsFv or Fab. Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 daltons, composed of two identical light (L) chains and two identical heavy (H) chains. Each heavy chain has at one end a variable domain ($V_H$) followed by a number of constant domains. Each light chain has a variable domain at one end ($V_L$) and a constant domain at its other end.

Anti-hPG monoclonal antibodies of the disclosure comprise complementarity determining regions (CDRs). CDRs are also known as hypervariable regions both in the light chain and the heavy chain variable domains. The more highly conserved portions of variable domains are called the framework (FR). As is known in the art, the amino acid position/boundary delineating a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The disclosure provides antibodies comprising modifications in these hybrid hypervariable positions. The variable domains of native heavy and light chains each comprise four FR regions, largely by adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the target binding site of antibodies (See Kabat et al., Sequences of Proteins of Immunological Interest (National Institute of Health, Bethesda, Md. 1987).

Several anti-hPG monoclonal antibodies having high specificity and affinity for hPG and good anti-tumor activity have been identified, and their CDRs and variable heavy and light chains have been sequenced. Murine heavy and light chain variable domains are referred to herein as $mV_H$ and $mV_L$ followed by the number of the corresponding monoclonal antibody, for example $mV_H$.3 and $mV_L$.3 for anti-hPG MAb3. Anti-hPG monoclonal antibodies have three variable light chain CDRs and three variable heavy chain CDRs, referred to as $V_H$ CDR1, 2, or 3, and $V_L$ CDR1, 2, or 3, respectively, followed by the number of the exemplary anti-hPG monoclonal antibody. For example, $V_L$ CDR1 of MAb 3 is denoted $V_L$ CDR1.3 and $V_H$ CDR1 of MAb 3 is denoted $V_H$ CDR1.3. Similarly, human heavy and light chain variable domains are referred to herein as $hV_H$ and $hV_L$ followed by the number of the corresponding monoclonal antibody.

In some embodiments, anti-hPG monoclonal antibodies raised against an N-terminal portion of hPG have three variable light chain CDRs and three variable heavy chain CDRs, wherein the $V_L$ CDR1 is selected from QSIVHSNGNTY ("$V_L$ CDR 1.3"; SEQ ID NO:4), QSLVHSSGVTY ("$V_L$ CDR 1.4"; SEQ ID NO:10), QSLLDSDGKTY ("$V_L$ CDR 1.16"; SEQ ID NO:50), and SQHRTYT ("$V_L$ CDR 1.19"; SEQ ID NO:51); the $V_L$ CDR2 is selected from KVS ("$V_L$ CDR 2.3" and ("$V_L$ CDR 2.4"; SEQ ID NO:5), LVS ("$V_L$ CDR 2.16"; SEQ ID NO:53), and VKKDGSH ("$V_L$ CDR 2.19"; SEQ ID NO:54); the $V_L$ CDR3 is selected from FQGSHVPFT ("$V_L$ CDR 3.3"; SEQ ID NO:6), SQSTHVPPT ("$V_L$ CDR 3.4"; SEQ ID NO:11), WQGTHSPYT ("$V_L$ CDR 3.16"; SEQ ID NO:57), and GVGDAIKGQSVFV ("$V_L$ CDR 3.19"; SEQ ID NO:58); the $V_H$ CDR1 is selected from GYIFTSYW ("$V_H$ CDR 1.3"; SEQ ID NO:1), GYTFSSSW ("$V_H$ CDR 1.4"; SEQ ID NO:7), GYTFTSYY ("$V_H$ CDR 1.16"; SEQ ID NO:39), and GYSITSDYA ("$V_H$ CDR 1.19"; SEQ ID NO:40); the $V_H$ CDR2 is selected from FYPGNSDS ("$V_H$ CDR 2.3"; SEQ ID NO:2), FLPGSGST ("$V_H$ CDR 2.4"; SEQ ID NO:8), INPSNGGT ("$V_H$ CDR 2.16"; SEQ ID NO:43), and ISFSGYT ("$V_H$ CDR 2.19"; SEQ ID NO:44); and the $V_H$ CDR3 is selected from TRRDSPQY ("$V_H$ CDR 3.3"; SEQ ID NO:3), ATDGNYDWFAY ("$V_H$ CDR 3.4" SEQ ID NO:9), TRGGYYPFDY ("$V_H$ CDR 3.16"; SEQ ID NO:47), and AREVNYGDSYHFDY ("$V_H$ CDR 3.19"; SEQ ID NO:48). See Table 1A.

In some embodiments, anti-hPG monoclonal antibodies raised against a C-terminal portion of hPG have three variable light chain CDRs and three variable heavy chain CDRs, wherein the $V_L$ CDR1 is selected from KSLRHTKGITF ("$V_L$ CDR 1.8"; SEQ ID NO:49) and QSLLDSDGKTY ("$V_L$ CDR 1.13"; SEQ ID NO:50); the $V_L$ CDR2 is selected from QMS ("$V_L$ CDR 2.8"; SEQ ID NO:52) and LVS ("$V_L$ CDR 2.13"; SEQ ID NO:53); the $V_L$ CDR3 is selected from AQNLELPLT ("$V_L$ CDR 3.8"; SEQ ID NO:55) and WQGTHFPQT ("$V_L$ CDR 3.13"; SEQ ID NO:56); the $V_H$ CDR1 is selected from GFTFTTYA ("$V_H$ CDR 1.8"; SEQ ID NO:37) and GFIFSSYG ("$V_H$ CDR 1.13"; SEQ ID NO:38); the $V_H$ CDR2 is selected from ISSGGTYT ("$V_H$ CDR 2.8"; SEQ ID NO:41) and INTFGDRT ("$V_H$ CDR 2.13"; SEQ ID NO:42); and the $V_H$ CDR3 is selected from ATQGNYSLDF ("$V_H$ CDR 3.8"; SEQ ID NO:45) and ARGTGTY ("$V_H$ CDR 3.13"; SEQ ID NO:46). See Table 1B.

TABLE 1A

N-Terminal Anti-hPG Monoclonal Antibodies

| Immunogen | Hybridoma (Deposit #) | MAb | Murine CDR Sequences | | | Murine $V_H$ and $V_L$ Sequences | Humanized $V_H$ and $V_L$ Sequences (projected) |
|---|---|---|---|---|---|---|---|
| N1 | 43B9G11 | MAb1 | | | | | |
| N1 | WE5H2G7 | MAb2 | | | | | |
| N2 | 6B5B11C10 | MAb3 | $V_H$ CDR 1.3 | GYIFTSYW | (SEQ ID NO: 1) | m$V_H$ 3 (SEQ ID NO. 12) | h$V_H$ 3 (SEQ ID NO: 21) |
| | | | $V_H$ CDR 2.3 | FYPGNSDS | (SEQ ID NO: 2) | | |
| | | | $V_H$ CDR 3.3 | TRRDSPQY | (SEQ ID NO: 3) | | |
| | | | $V_L$ CDR 1.3 | QSIVHSNGNTY | (SEQ ID NO: 4) | m$V_L$ 3 (SEQ ID NO: 13) | h$V_L$ 3 (SEQ ID NO: 22) |
| | | | $V_L$ CDR 2.3 | KVS | (SEQ ID NO: 5) | | |
| | | | $V_L$ CDR 3.3 | FQGSHVPFT | (SEQ ID NO: 6) | | |
| N2 | 20D2C3G2 | MAb4 | $V_H$ CDR 1.4 | GYTFSSSW | (SEQ ID NO: 7) | m$V_H$ 4 (SEQ ID NO: 14) | h$V_H$ 4 (SEQ ID NO: 23) |
| | | | $V_H$ CDR 2.4 | FLPGSGST | (SEQ ID NO: 8) | | |
| | | | $V_H$ CDR 3.4 | ATDGNYDWFAY | (SEQ ID NO: 9) | | |
| | | | $V_L$ CDR 1.4 | QSLVHSSGVTY | (SEQ ID NO: 10) | m$V_L$ 4 (SEQ ID NO: 15) | h$V_L$ 4 (SEQ ID NO: 24) |
| | | | $V_L$ CDR 2.4 | KVS | (SEQ ID NO: 5) | | |
| | | | $V_L$ CDR 3.4 | SQSTHVPPT | (SEQ ID NO: 11) | | |
| N2 | 1E9A4A4 (I-4376) | MAb15 | | | | | |
| N2 | 1E9D9B6 | MAb16 | $V_H$ CDR 1.16 | GYTFTSYY | (SEQ ID NO: 39) | m$V_H$ 16 (SEQ ID NO: 61) | h$V_H$ 16a (SEQ ID NO: 84) |
| | | | $V_H$ CDR 2.16 | INPSNGGT | (SEQ ID NO: 43) | | h$V_H$ 16b (SEQ ID NO: 86) |
| | | | $V_H$ CDR 3.16 | TRGGYYPFDY | (SEQ ID NO: 47) | | h$V_H$ 16c (SEQ ID NO: 88) |
| | | | $V_L$ CDR 1.16 | QSLLDSDGKTY | (SEQ ID NO: 50) | m$V_L$ 16 (SEQ ID NO: 65) | h$V_L$ 16a (SEQ ID NO: 85) |
| | | | $V_L$ CDR 2.16 | LVS | (SEQ ID NO: 53) | | h$V_L$ 16b (SEQ ID NO: 87) |
| | | | $V_L$ CDR 3.16 | WQGTHSPYT | (SEQ ID NO: 57) | | h$V_L$ 16c (SEQ ID NO: 89) |
| N2 | 1C8D10F5 | MAb17 | | | | | |
| N2 | 1A7C3F11 | MAb18 | | | | | |
| N2 | 1B3B4F11 | MAb19 | $V_H$ CDR 1.19 | GYSITSDYA | (SEQ ID NO: 40) | m$V_H$ 19 (SEQ ID NO: 62) | h$V_H$ 19a (SEQ ID NO: 90) |
| | | | $V_H$ CDR 2.19 | ISFSGYT | (SEQ ID NO: 44) | | h$V_H$ 19b (SEQ ID NO: 92) |
| | | | $V_H$ CDR 3.19 | AREVNYGDSYHFDY | (SEQ ID NO: 48) | | h$V_H$ 19c (SEQ ID NO: 94) |

TABLE 1A-continued

| N-Terminal Anti-hPG Monoclonal Antibodies | | | | | | | |
|---|---|---|---|---|---|---|---|
| Immunogen | Hybridoma (Deposit #) | MAb | Murine CDR Sequences | | | Murine $V_H$ and $V_L$ Sequences | Humanized $V_H$ and $V_L$ Sequences (projected) |
| | | | $V_L$ CDR 1.19 | SQHRTYT | (SEQ ID NO: 51) | m$V_L$ 19 (SEQ ID NO: 66) | h$V_L$ 19a (SEQ ID NO: 91) |
| | | | $V_L$ CDR 2.19 | VKKDGSH | (SEQ ID NO: 54) | | h$V_L$ 19b (SEQ ID NO: 93) |
| | | | $V_L$ CDR 3.19 | GVGDAIKGQSVFV | (SEQ ID NO: 58) | | h$V_L$ 19c (SEQ ID NO: 95) |
| N2 | 1C11F5E8 | MAb20 | | | | | |

Immunogen N1 = SWKPRSQQPDAPLG Ahx Cys BSA, also represented as (SEQ ID NO: 25) Ahx Cys BSA Immunogen N2 = SWKPRSQQPDAPLG Ahx Cys KLH, also represented as (SEQ ID NO: 25) Ahx Cys KLH In Table 1A, all amino acid sequences are represented using conventional N→C orientation. For each immunogen, the progastrin peptide was synthesized with a linker of one aminohexanoic acid (Ahx) residues followed by a cysteine, which was then conjugated to a either a bovine serum albumin ("BSA") or keyhole limpet hemocyanin ("KLH") carrier.

TABLE 1B

C-Terminal Anti-hPG Monoclonal Antibodies

| Immunogen | Hybridoma (Deposit #) | MAb | Murine CDR Sequences | | | Murine $V_H$ and $V_L$ Sequences | Humanized $V_H$ and $V_L$ Sequences (projected) |
|---|---|---|---|---|---|---|---|
| C1 | 1B4A11D11 (1-4371) | MAb5 | | | | | |
| C1 | 1B6A11F2 (1-4372) | MAb6 | | | | | |
| C1 | 1B11E4B11 (1-4373) | MAb7 | | | | | |
| C1 | 1C10D3B9 | MAb8 | $V_H$ CDR 1.8 | GFTFTTYA | (SEQ ID NO: 37) | m$V_H$.8 (SEQ ID NO: 59) | h$V_H$ 8a (SEQ ID NO: 75) |
| | | | $V_H$ CDR 2.8 | ISSGGTYT | (SEQ ID NO: 41) | | h$V_H$ 8b (SEQ ID NO: 77) |
| | | | $V_H$ CDR 3.8 | ATQGNYSLDF | (SEQ ID NO: 45) | | h$V_H$ 8c (SEQ ID NO: 79) |
| | | | $V_L$ CDR 1.8 | KSLRHTKGITF | (SEQ ID NO: 49) | m$V_L$.8 (SEQ ID NO: 63) | h$V_L$ 8a (SEQ ID NO: 76) |
| | | | $V_L$ CDR 2.8 | QMS | (SEQ ID NO: 52) | | h$V_L$ 8b (SEQ ID NO: 78) |
| | | | $V_L$ CDR 3.8 | AQNLELPLT | (SEQ ID NO: 55) | | h$V_L$ 8c (SEQ ID NO: 76) |
| C1 | 1D8F5B3 | MAb9 | | | | | |
| C1 | 1E1C7B4 | MAb10 | | | | | |
| C1 | 2B4C8C8 (1-4374) | MAb11 | | | | | |
| C1 | 2B11E6G4 (1-4375) | MAb12 | | | | | |
| C1 | 2C6C3C7 | MAb13 | $V_H$ CDR 1.13 | GFIFSSYG | (SEQ ID NO: 38) | m$V_H$.13 (SEQ ID NO: 60) | h$V_H$.13a (SEQ ID NO: 80) |
| | | | $V_H$ CDR 2.13 | INTFGDRT | (SEQ ID NO: 42) | | h$V_H$.13b (SEQ ID NO: 82) |
| | | | $V_H$ CDR 3.13 | ARGTGTY | (SEQ ID NO: 46) | | |
| | | | $V_L$ CDR 1.13 | QSLLDSDGKTY | (SEQ ID NO: 50) | m$V_L$.13 (SEQ ID NO: 64) | h$V_L$ 13a (SEQ ID NO: 81) |
| | | | $V_L$ CDR 2.13 | LVS | (SEQ ID NO: 53) | | h$V_L$ 13b (SEQ ID NO: 83) |
| | | | $V_L$ CDR 3.13 | WQGTHFPQT | (SEQ ID NO: 56) | | |
| C1 | 2H9F4B7 | MAb14 | | | | | |
| C2 | 1F11F5E10 | MAb21 | | | | | |

TABLE 1B-continued

| C-Terminal Anti-hPG Monoclonal Antibodies | | | | | |
|---|---|---|---|---|---|
| Immunogen | Hybridoma (Deposit #) | MAb | Murine CDR Sequences | Murine $V_H$ and $V_L$ Sequences | Humanized $V_H$ and $V_L$ Sequences (projected) |
| C2 | 1F11F5G9 | MAb22 | | | |
| C2 | 1A11F2C9 | MAb23 | | | |

Immunogen C1 = KLH Cys Ahx Ahx Ahx Ahx QGPWLEEEEEAYGWMDFGRRSAEDEN, also represented as KLH Cys(SEQ ID NO: 27)

Immunogen C2 = DT Cys Ahx Ahx QGPWLEEEEEAYGWMDFGRRSAEDEN, also represented as DT Cys Ahx Ahx (SEQ ID NO: 27)

In Table 1B, all amino acid sequences are represented using conventional N→C orientation. For each immunogen, the progastrin peptide was synthesized with a linker of two aminohexanoic acid (Ahx) residues followed by a cysteine, which was then conjugated to a either a keyhole limpet hemocyanin ("KLH") or a diphtheria toxin ("DT") carrier.

In some embodiments, the CDRs of the $V_H$ chain of the anti-hPG monoclonal antibody are $V_H$CDR1.3, $V_H$CDR2.3 and $V_H$CDR3.3. In a specific embodiment, the $V_H$ chain of the anti-hPG monoclonal antibody has an amino acid sequence corresponding to m$V_H$.3 (SEQ ID NO:12). See FIG. 2A.

In some embodiments, the CDRs of the $V_L$ chain of the anti-hPG monoclonal antibody are $V_L$CDR1.3, $V_L$CDR2.3 and $V_L$CDR3.3. In a specific embodiment, the $V_L$ chain of the anti-hPG monoclonal antibody has an amino acid sequence corresponding to m$V_L$.3 (SEQ ID NO:13). See FIG. 2B.

In some embodiments, the CDRs of the $V_H$ chain of the anti-hPG monoclonal antibody are $V_H$CDR1.4, $V_H$CDR2.4 and $V_H$CDR3.4. In a specific embodiment, the $V_H$ chain of the anti-hPG monoclonal antibody has a sequence corresponding to m$V_H$.4 (SEQ ID NO:14). See FIG. 2C.

In some embodiments, the CDRs of the anti-hPG monoclonal antibody $V_L$ chain are $V_L$CDR1.4, $V_L$CDR2.4 and $V_L$CDR3.4 In a specific embodiment, the $V_L$ chain of the anti-hPG monoclonal antibody has an amino acid sequence corresponding to m$V_L$.4 (SEQ ID NO:15). See FIG. 2D.

In some embodiments, the CDRs of the $V_H$ chain of the anti-hPG monoclonal antibody are $V_H$CDR1.8, $V_H$CDR2.8 and $V_H$CDR3.8. In a specific embodiment, the $V_H$ chain of the anti-hPG monoclonal antibody has a sequence corresponding to m$V_H$.8 (SEQ ID NO:59). See FIG. 2E.

In some embodiments, the CDRs of the anti-hPG monoclonal antibody $V_L$ chain are $V_L$ CDR1.8, $V_L$ CDR2.8 and $V_L$ CDR3.8. In a specific embodiment, the $V_L$ chain of the anti-hPG monoclonal antibody has an amino acid sequence corresponding to m$V_L$ 0.8 (SEQ ID NO:63). See FIG. 2F.

In some embodiments, the CDRs of the $V_H$ chain of the anti-hPG monoclonal antibody are $V_H$CDR1.13, $V_H$CDR2.13 and $V_H$CDR3.13. In a specific embodiment, the $V_H$ chain of the anti-hPG monoclonal antibody has a sequence corresponding to m$V_H$.13 (SEQ ID NO:60). See FIG. 2G.

In some embodiments, the CDRs of the anti-hPG monoclonal antibody $V_L$ chain are $V_L$ CDR1.13, $V_L$ CDR2.13 and $V_L$ CDR3.13. In a specific embodiment, the $V_L$ chain of the anti-hPG monoclonal antibody has an amino acid sequence corresponding to m$V_L$.13 (SEQ ID NO:64). See FIG. 2H.

In some embodiments, the CDRs of the $V_H$ chain of the anti-hPG monoclonal antibody are $V_H$CDR1.16, $V_H$CDR2.16 and $V_H$CDR3.16. In a specific embodiment, the $V_H$ chain of the anti-hPG monoclonal antibody has a sequence corresponding to m$V_H$.16 (SEQ ID NO:61). See FIG. 2I.

In some embodiments, the CDRs of the anti-hPG monoclonal antibody $V_L$ chain are $V_L$ CDR1.16, $V_L$ CDR2.16 and $V_L$ CDR3.16. In a specific embodiment, the $V_L$ chain of the anti-hPG monoclonal antibody has an amino acid sequence corresponding to m$V_L$.16 (SEQ ID NO:65). See FIG. 2J.

In some embodiments, the CDRs of the $V_H$ chain of the anti-hPG monoclonal antibody are $V_H$CDR1.19, $V_H$CDR2.19 and $V_H$CDR3.19. In a specific embodiment, the $V_H$ chain of the anti-hPG monoclonal antibody has a sequence corresponding to m$V_H$.19 (SEQ ID NO:62). See FIG. 2K.

In some embodiments, the CDRs of the anti-hPG monoclonal antibody $V_L$ chain are $V_L$ CDR1.19, $V_L$ CDR2.19 and $V_L$ CDR3.19. In a specific embodiment, the $V_L$ chain of the anti-hPG monoclonal antibody has an amino acid sequence corresponding to m$V_L$.19 (SEQ ID NO:66). See FIG. 2L.

In some embodiments, the CDRs of the $V_H$ chain of the anti-hPG monoclonal antibody are $V_H$CDR1.3, $V_H$CDR2.3 and $V_H$CDR3.3 and the CDRs of the $V_L$ chain are $V_L$CDR1.3, $V_L$CDR2.3 and $V_L$CDR3.3. In a specific embodiment, the $V_H$ chain of the anti-PG monoclonal antibody has an amino acid sequence corresponding to m$V_H$.3 (SEQ ID NO: 12) and the $V_L$ chain has a sequence corresponding to m$V_L$.3 (SEQ ID NO:13).

In some embodiments, the CDRs of the $V_H$ chain of the anti-hPG monoclonal antibody are $V_H$CDR1.4, $V_H$CDR2.4 and $V_H$CDR3.4 and the CDRs of the $V_L$ chain are $V_L$CDR1.4, $V_L$CDR2.4 and $V_L$CDR3.4. In a specific embodiment, the $V_H$ chain of the anti-hPG monoclonal antibody has an amino acid sequence corresponding to m$V_H$.4 (SEQ ID NO:14) and a $V_L$ chain has an amino acid sequence corresponding to m$V_L$.4 (SEQ ID NO:15).

In some embodiments, the CDRs of the $V_H$ chain of the anti-hPG monoclonal antibody are $V_H$CDR1.8, $V_H$CDR2.8 and $V_H$CDR3.8 and the CDRs of the $V_L$ chain are $V_L$CDR1.8, $V_L$CDR2.8 and $V_L$CDR3.8. In a specific embodiment, the anti-hPG monoclonal antibody is anti-hPG MAb 8 described herein and comprises an amino acid sequence corresponding to m$V_H$.8 (SEQ ID NO:59) and an amino acid sequence corresponding to m$V_L$.8 (SEQ ID NO:63).

In some embodiments, the CDRs of the $V_H$ chain of the anti-hPG monoclonal antibody are $V_H$CDR1.3, $V_H$CDR2.13 and $V_H$CDR3.13 and the CDRs of the $V_L$ chain are $V_L$CDR1.13, $V_L$CDR2.13 and $V_L$CDR3.13. In a specific embodiment, the anti-hPG monoclonal antibody is anti-hPG MAb 13 described herein and comprises an amino acid sequence corresponding to m$V_H$.13 (SEQ ID NO:60) and an amino acid sequence corresponding to m$V_L$.13 (SEQ ID NO:64).

In some embodiments, the CDRs of the $V_H$ chain of the anti-hPG monoclonal antibody are $V_H$CDR1.16, $V_H$CDR2.16 and $V_H$CDR3.16 and the CDRs of the $V_L$ chain are $V_L$CDR1.16, $V_L$CDR2.16 and $V_L$CDR3.16. In a specific embodiment, the anti-hPG monoclonal antibody is anti-hPG MAb 16 described herein and comprises an amino acid sequence corresponding to m$V_H$.16 (SEQ ID NO:61) and an amino acid sequence corresponding to m$V_L$.16 (SEQ ID NO:65).

In some embodiments, the CDRs of the $V_H$ chain of the anti-hPG monoclonal antibody are $V_H$CDR1.19, $V_H$CDR2.19 and $V_H$CDR3.19 and the CDRs of the $V_L$ chain are $V_L$CDR1.19, $V_L$CDR2.19 and $V_L$CDR3.19. In a specific embodiment, the anti-hPG monoclonal antibody is anti-hPG MAb 19 described herein and comprises an amino acid sequence corresponding to m$V_H$.19 (SEQ ID NO:62) and an amino acid sequence corresponding to m$V_L$.19 (SEQ ID NO:66).

Anti-hPG monoclonal antibodies of the disclosure include both intact molecules, and antibody fragments (such as, for example, Fab and $F(ab')_2$ fragments) which are capable of specifically binding to hPG. Fab and $F(ab')_2$ fragments lack the Fc fragment of intact antibody, clear more rapidly from the circulation of the animal or plant, and may have less non-specific tissue binding than an intact antibody (Wahl et al., 1983, J. Nucl. Med. 24:316). Antibody fragments are therefore useful in therapeutic applications among other applications.

The term “antibody fragment” refers to a portion of a full-length antibody, generally the target binding or variable region. Examples of antibody fragments include Fab, Fab', F(ab')2 and Fv fragments. An “Fv” fragment is the minimum antibody fragment which contains a complete target recognition and binding site. This region consists of a dimer of one heavy and one light chain variable domain in a tight, non-covalent association ($V_H$-$V_L$ dimer). It is in this configuration that the three CDRs of each variable domain interact to define a target binding site on the surface of the $V_H$-$V_L$ dimer. Often, the six CDRs confer target binding specificity to the antibody. However, in some instances even a single variable domain (or half of an Fv comprising only three CDRs specific for a target) can have the ability to recognize and bind target, although at a lower affinity than the entire binding site. "Single-chain Fv" or "scFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for target binding. "Single domain antibodies" are composed of a single $V_H$ or $V_L$ domains which exhibit sufficient affinity to hPG. In a specific embodiment, the single domain antibody is a camelized antibody (See, e.g., Riechmann, 1999, Journal of Immunological Methods 231:25-38).

The Fab fragment contains the constant domain of the light chain and the first constant domain ($CH_1$) of the heavy chain. Fab' fragments differ from Fab fragments by the addition of a few residues at the carboxyl terminus of the heavy chain $CH_1$ domain including one or more cysteines from the antibody hinge region. F(ab') fragments are produced by cleavage of the disulfide bond at the hinge cysteines of the $F(ab')_2$ pepsin digestion product. Additional chemical couplings of antibody fragments are known to those of ordinary skill in the art.

The anti-hPG monoclonal antibodies of the disclosure can be chimeric antibodies. The term "chimeric" antibody as used herein refers to an antibody having variable sequences derived from a non-human immunoglobulins, such as rat or mouse antibody, and human immunoglobulins constant regions, typically chosen from a human immunoglobulin template. Methods for producing chimeric antibodies are known in the art. See, e.g., Morrison, 1985, Science 229 (4719):1202-7; Oi et al., 1986, BioTechniques 4:214-221; Gillies et al., 1985, J. Immunol. Methods 125:191-202; U.S. Pat. Nos. 5,807,715; 4,816,567; and 4,816397, which are incorporated herein by reference in their entireties.

The anti-hPG monoclonal antibodies of the disclosure can be humanized. "Humanized" forms of non-human (e.g., murine) antibodies are chimeric immunoglobulins, immunoglobulin chains or fragments thereof (such as Fv, Fab, Fab', $F(ab')_2$ or other target-binding subsequences of antibodies) which contain minimal sequences derived from non-human immunoglobulins. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence, and can be referred to as "CDR-grafted." The humanized antibody can also comprise at least a portion of an immunoglobulin constant region (Fc), typically that of a human immunoglobulin consensus sequence. Methods of antibody humanization, including methods of designing humanized antibodies, are known in the art. See, e.g., Lefranc et al., 2003, Dev. Comp. Immunol. 27:55-77; Lefranc et al., 2009, Nucl. Acids Res. 37: D1006-1012; Lefranc, 2008, Mol. Biotechnol. 40: 101-111; Riechmann et al., 1988, Nature 332:323-7; U.S. Pat. Nos. 5,530,101; 5,585,089; 5,693,761; 5,693,762; and U.S. Pat. No. 6,180, 370 to Queen et al.; EP239400; PCT publication WO 91/09967; U.S. Pat. No. 5,225,539; EP592106; EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973; and U.S. Pat. No. 5,565,332, all of which are hereby incorporated by reference in their entireties.

Sequences for humanized anti-hPG monoclonal antibodies were designed from murine anti-hPG monoclonal antibodies of the present disclosure as described in the Examples below. Specific embodiments of humanized antibodies include antibodies comprising: (1) any three VL CDRs and any three VH CDRs disclosed herein; (2) a heavy chain variable region comprising an amino acid sequence corresponding to SEQ ID NO:21 and a light chain variable region comprising an amino acid sequence corresponding to SEQ ID NO:22; (3) a heavy chain variable region comprising an amino acid sequence corresponding to SEQ ID NO:23 and a light chain variable region comprising an amino acid sequence corresponding to SEQ ID NO:24; (4) a heavy chain variable region comprising an amino acid sequence selected from the group consisting of SEQ ID NO:75, 77, and 79 and a light chain variable region comprising an amino acid sequence selected from the group consisting of SEQ ID NO:76 and 78; (5) a heavy chain variable region comprising an amino acid sequence selected from the group consisting of SEQ ID NO:80 and 82 and a light chain variable region comprising an amino acid sequence selected from the group consisting of SEQ ID NO:81 and 83; (6) a heavy chain variable region comprising an amino acid sequence selected from the group consisting of SEQ ID NO:84, 86, and 88 and a light chain variable region comprising an amino acid sequence selected from the group consisting of SEQ ID NO:85, 87, and 89; (7) a heavy chain variable region comprising an amino acid sequence selected from the group consisting of SEQ ID NO:90, 92, and 94 and a light chain variable region comprising an amino acid sequence selected from the group consisting of SEQ ID NO:91, 93, and 95.

The anti-hPG monoclonal antibodies of the disclosure can be primatized. The term "primatized antibody" refers to an antibody comprising monkey variable regions and human constant regions. Methods for producing primatized antibodies are known in the art. See, e.g., U.S. Pat. Nos. 5,658,570; 5,681,722; and 5,693,780, which are incorporated herein by reference in their entireties.

Included within anti-hPG monoclonal antibodies are antibodies that compete with a reference antibody, such as, for example, a polyclonal anti-hPG antibody, or any of the anti-hPG monoclonal antibodies disclosed herein. Antibodies that compete with the anti-hPG monoclonal antibodies of the disclosure are useful in for a variety of diagnostic and therapeutic applications. Specific embodiments of suitable reference anti-hPG monoclonal antibodies include the antibodies described herein, for example, but not by way of limitation: antibodies comprising any three $V_L$ CDRs and any three $V_H$ CDRs disclosed herein; antibodies in which the $V_H$ chain has an amino acid sequence corresponding to SEQ ID NO:12 (m$V_H$.3) and the $V_L$ chain has an amino acid sequence corresponding to SEQ ID NO:13 (m$V_L$.3); and antibodies in which the $V_H$ chain has an amino acid sequence corresponding to SEQ ID NO:14 (m$V_H$.4) and the $V_L$ chain has a sequence corresponding to SEQ ID NO:15 (m$V_L$.4), antibodies in which the VH chain has an amino acid sequence corresponding to SEQ ID NO:59 (m$V_H$.8) and the VL chain has an amino acid sequence corresponding to SEQ ID NO:63 (m$V_L$.8); antibodies in which the $V_H$ chain has an amino acid sequence corresponding to SEQ ID NO:60 (m$V_H$.13) and the $V_L$ chain has an amino acid sequence corresponding to SEQ ID NO:64 (m$V_L$.13); antibodies in which the $V_H$ chain has an amino acid sequence corresponding to SEQ ID NO:61 ($mV_H$.16) and the $V_L$ chain has an amino acid sequence corresponding to SEQ ID NO:65 ($mV_L$.16); antibodies in which the $V_H$ chain has an amino acid sequence corresponding to SEQ ID NO:62 ($mV_H$.19) and the $V_L$ chain has an amino acid sequence corresponding to SEQ ID NO:66 ($mV_L$.19) or any combination of $V_H$ and $V_L$ chains disclosed herein.

Suitable reference antibodies also include antibodies produced by a hybridoma selected from the group consisting of 43B9G11, WE5H2G7, 6B5B11C10, 20D2C3G2, 1B4A11D11, 1B6A11F2, 1B11E4B11, 1C10D3B9, 1D8F5B3, 1E1C7B4, 2B4C8C8, 2B11E6G4, 2C6C3C7, 2H9F4B7, 1E9A4A4, 1E9D9B6, 1C8D10F5, 1A7C3F11, 1B3B4F11, 1C11F5E8, 1F11F5E10, 1F11F5G9, and 1A11F2C9; antibodies that bind an epitope that includes residues 10 to 14 of hPG (SEQ ID NO:28), residues 9 to 14 of hPG (SEQ ID NO:29), residues 4 to 10 of hPG (SEQ ID NO:30), residues 2 to 10 of hPG (SEQ ID NO:31), or residues 2 to 14 of hPG (SEQ ID NO:32); and antibodies that bind an epitope that includes residues 71 to 74 of hPG (SEQ ID NO:33), residues 69 to 73 of hPG (SEQ ID NO:34), residues 76 to 80 of hPG (SEQ ID NO:35), or residues 67 to 74 of hPG (SEQ ID NO:36).

The ability to compete with a monoclonal antibody of the present disclosure for binding to PG, for example hPG, can be tested using a competition assay as follows. 96-well plates are coated with a capture antibody (polyclonal or monoclonal antibody recognizing an N- or C-terminal region of progastrin that differs from the epitope recognized by the reference monoclonal antibody), at a concentration to be chosen within the range of 1-10 μg/ml, overnight at 4° C. (0.1 to 1 μg/well). After blocking with 0.1% TWEEN®-20/0.1% BSA in PBS (blocking buffer) for 2 h at 22° C., recombinant human progastrin is added at a concentration of 10 pM to 1 nM (10 to 1000 pg/well) and incubated for 2 h at 22° C. Thereafter, the biotinylated reference anti-hPG monoclonal antibody or a mixture containing the reference monoclonal antibody is added along with increasing concentrations of unlabeled test antibodies and incubated for 1 hour at 22° C. After washing, detection is performed by incubating for 1 h at 22° C. with a fluorogenic substrate for horseradish peroxidase, followed by quantitation of relative light units (RLU) in a luminometer. Assays are performed in duplicate. Antibodies that compete with a reference anti-hPG monoclonal antibody of the present disclosure inhibit the binding of the reference antibody to hPG. An antibody that binds to the same epitope as the control antibodies will be able to effectively compete for binding and thus will significantly reduce (for example, by at least 50%) the reference antibody binding, as evidenced by a reduction in the bound label. The reactivity of the (labeled) reference antibodies in the absence of a completely irrelevant antibody would be the control high value. The control low value would be obtained by incubating the unlabeled test antibodies with cells expressing progastrin and then incubate the cell/antibody mixture with labeled control antibodies of exactly the same type, when competition would occur and reduce binding of the labeled antibodies. In a test assay, a significant reduction in labeled antibody reactivity in the presence of a test antibody is indicative of a test antibody that recognizes substantially the same epitope.

The binding inhibition can be expressed as an inhibition constant, or Ki, which is calculated according to the following formula:

$$Ki=IC50/(1+[\text{Reference } Ab \text{ concentration}]/Kd)$$

Where IC50 of the test antibody is the concentration of test antibody that yields a 50% reduction in binding of the reference antibody and Kd is the dissociation constant of the reference antibody, a measure of its affinity for progastrin. Antibodies that compete with anti-hPG monoclonal antibodies disclosed herein can have a Ki from 10 pM to 10 nM under assay conditions described herein.

In various embodiments, an unlabeled anti-hPG monoclonal antibody of the disclosure reduces the binding of labeled reference antibody by at least 40%, by at least 50%, by at least 60%, by at least 70%, by at least 80%, by at least 90%, by 100%, or by a percentage ranging between any of the foregoing values (e.g., an anti-hPG monoclonal antibody of the disclosure reduces the binding of labeled reference antibody by 50% to 70%) when the anti-hPG monoclonal antibody is used at a concentration of 0.01 μg/ml, 0.08 μg/ml, 0.4 μg/ml, 2 μg/ml, 10 μg/ml, 50 μg/ml, 100 μg/ml or at a concentration ranging between any of the foregoing values (e.g., at a concentration ranging from 2 μg/ml to 10 μg/ml).

In conducting an antibody competition study between a reference antibody and any test antibody (irrespective of species or isotype), one may first label the reference with a detectable label, such as, biotin or an enzymatic (or even radioactive) label to enable subsequent identification. In this case, labeled reference antibody (in fixed or increasing concentrations) is incubated with a known amount of progastrin. The unlabeled test antibody is then added to the pre-bound complex of progastrin and labeled antibody. The intensity of the bound label is measured. If the test antibody competes with the labeled antibody by binding to an overlapping epitope, the intensity will be decreased relative to the binding of the control labeled antibody in the absence of the test antibody.

Assays for competition are known and can be adapted to yield comparable results to the assay described above. The assay may be any one of a range of immunological assays based upon antibody competition, and the reference antibodies would be detected by means of detecting their label, e.g., by using streptavidin in the case of biotinylated antibodies or by using a chromogenic substrate in connection with an enzymatic label (such as 3,3'5,5'-tetramethylbenzidine (TMB) substrate with peroxidase enzyme) or by simply detecting a radioactive label or a fluorescence label.

Also included herein are anti-hPG monoclonal antibodies which are derivatized, covalently modified, or conjugated to other molecules, for use in diagnostic and therapeutic applications. For example, but not by way of limitation, derivatized antibodies include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to, specific chemical cleavage, acetylation, formylation, metabolic synthesis of tunicamycin, etc. Additionally, the derivative can contain one or more non-classical amino acids.

In another example, antibodies of the present disclosure can be attached to poly(ethyleneglycol) (PEG) moieties. In a specific embodiment, the antibody is an antibody fragment and the PEG moieties are attached through any available amino acid side-chain or terminal amino acid functional group located in the antibody fragment, for example any free amino, imino, thiol, hydroxyl or carboxyl group. Such amino acids can occur naturally in the antibody fragment or can be engineered into the fragment using recombinant DNA methods. See, for example U.S. Pat. No. 5,219,996. Multiple sites can be used to attach two or more PEG molecules. PEG moieties can be covalently linked through a thiol group of at least one cysteine residue located in the antibody fragment. Where a thiol group is used as the point of attachment, appropriately activated effector moieties, for example thiol selective derivatives such as maleimides and cysteine derivatives, can be used.

In a specific example, an anti-hPG monoclonal antibody conjugate is a modified Fab' fragment which is PEGylated, i.e., has PEG (poly(ethyleneglycol)) covalently attached thereto, e.g., according to the method disclosed in EP0948544. See also Poly(ethyleneglycol) Chemistry, Biotechnical and Biomedical Applications, (J. Milton Harris (ed.), Plenum Press, New York, 1992); Poly(ethyleneglycol) Chemistry and Biological Applications, (J. Milton Harris and S. Zalipsky, eds., American Chemical Society, Washington D.C., 1997); and Bioconjugation Protein Coupling Techniques for the Biomedical Sciences, (M. Aslam and A. Dent, eds., Grove Publishers, New York, 1998); and Chapman, 2002, Advanced Drug Delivery Reviews 54:531-545. PEG can be attached to a cysteine in the hinge region. In one example, a PEG-modified Fab' fragment has a maleimide group covalently linked to a single thiol group in a modified hinge region. A lysine residue can be covalently linked to the maleimide group and to each of the amine groups on the lysine residue can be attached a methoxypoly(ethyleneglycol) polymer having a molecular weight of approximately 20,000 Da. The total molecular weight of the PEG attached to the Fab' fragment can therefore be approximately 40,000 Da.

Anti-hPG monoclonal antibodies include labeled antibodies, useful in diagnostic applications. The antibodies can be used diagnostically, for example, to detect expression of a target of interest in specific cells, tissues, or serum; or to monitor the development or progression of an immunologic response as part of a clinical testing procedure to, e.g., determine the efficacy of a given treatment regimen. Detection can be facilitated by coupling the antibody to a detectable substance or "label." A label can be conjugated directly or indirectly to an anti-hPG monoclonal antibody of the disclosure. The label can itself be detectable (e.g., radioisotope labels, isotopic labels, or fluorescent labels) or, in the case of an enzymatic label, can catalyze chemical alteration of a substrate compound or composition which is detectable. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance can be coupled or conjugated either directly to the antibody (or fragment thereof) or indirectly, through an intermediate (such as, for example, a linker known in the art) using techniques known in the art. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, acetylcholinesterase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride, dimethylamine-1-napthalenesulfonyl chloride, or phycoerythrin and the like; an example of a luminescent material includes luminol; examples of bioluminescent materials include luciferase, luciferin, and aequorin; examples of suitable isotopic materials include $^{13}C$, $^{15}N$, and deuterium; and examples of suitable radioactive material include $^{125}I$, $^{131}I$, $^{111}In$ or $^{99}Tc$.

Anti-hPG monoclonal antibodies of all species of origin are included in the present invention. Non-limiting exemplary natural antibodies include antibodies derived from humans, simians, chicken, goats, rabbits, and rodents (e.g., rats, mice, and hamsters) (See, e.g., Lonberg et al., WO93/12227; U.S. Pat. No. 5,545,806; and Kucherlapati, et al., WO91/10741; U.S. Pat. No. 6,150,584, which are herein incorporated by reference in their entirety). Natural antibodies are the antibodies produced by a host animal after being immunized with an antigen, such as a polypeptide.

Nucleic Acids and Expression Systems

The present disclosure encompasses nucleic acid molecules encoding immunoglobulin light and heavy chain genes for anti-hPG monoclonal antibodies, vectors comprising such nucleic acids, and host cells capable of producing the anti-hPG monoclonal antibodies of the disclosure.

An anti-hPG monoclonal antibody of the disclosure can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Molecular Cloning; A Laboratory Manual, Second Edition (Sambrook, Fritsch and Maniatis (eds), Cold Spring Harbor, N.Y., 1989), Current Protocols in Molecular Biology (Ausubel, F. M. et al., eds., Greene Publishing Associates, 1989) and in U.S. Pat. No. 4,816,397.

To generate nucleic acids encoding such anti-hPG monoclonal antibodies, DNA fragments encoding the light and heavy chain variable regions are first obtained. These DNAs can be obtained by amplification and modification of germline DNA or cDNA encoding light and heavy chain variable sequences, for example using the polymerase chain reaction (PCR). Germline DNA sequences for human heavy and light chain variable region genes are known in the art (See, e.g., Lefranc et al., 2003, Dev. Comp. Immunol. 27:55-77; Lefranc et al., 2009, Nucl. Acids Res. 37: D1006-1012; Lefranc, 2008, Mol. Biotechnol. 40: 101-111; the "VBASE" human germline sequence database; see also Kabat, E. A. et al., 1991, Sequences of Proteins of Immunological Interest, Fifth Edition, U.S. Department of Health and Human Services, NIH Publication No. 91-3242; Tomlinson et al., 1992, J. Mol. Biol. 22T:116-198; and Cox et al., 1994, Eur. J. Immunol. 24:827-836; the contents of each of which are incorporated herein by reference).

Once DNA fragments encoding anti-hPG monoclonal antibody-related $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($CH_1$, $CH_2$, $CH_3$ and, optionally, $CH_4$). The sequences of human heavy chain constant region genes are known in the art (See, e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an $IgG_1$, $IgG_2$, $IgG_3$, $IgG_4$, IgA, IgE, IgM or IgD constant region, but in certain embodiments is an $IgG_1$ or $IgG_4$ constant region. For a Fab fragment heavy chain gene, the $V_H$-encoding DNA can be operatively linked to another DNA molecule encoding only the heavy chain $CH_1$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (See, e.g., Kabat, E. A., et al., 1991, Sequences of Proteins of Immunological Interest, Fifth Edition (U.S. Department of Health and Human Services, NIH Publication No. 91-3242)) and DNA fragments encompassing these regions can be obtained by standard PCR amplification. The light chain constant region can be a kappa or lambda constant region, but in certain embodiments is a kappa constant region. To create a scFv gene, the $V_H$- and $V_L$-encoding DNA fragments are operatively linked to another fragment encoding a flexible linker, e.g., encoding the amino acid sequence $(Gly_4\sim Ser)_3$ (SEQ ID NO: 99), such that the $V_H$ and $V_L$ sequences can be expressed as a contiguous single-chain protein, with the $V_L$ and $V_H$ regions joined by the flexible linker (See, e.g., Bird et al., 1988, Science 242:423-426; Huston et al., 1988, Proc. Natl. Acad. Sci. USA 85:5879-5883; McCafferty et al., 1990, Nature 348:552-554).

To express the anti-hPG monoclonal antibodies of the disclosure, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). Prior to insertion of the anti-hPG monoclonal antibody-related light or heavy chain sequences, the expression vector can already carry antibody constant region sequences. For example, one approach to converting the anti-hPG monoclonal antibody-related $V_H$ and $V_L$ sequences to full-length antibody genes is to insert them into expression vectors already encoding heavy chain constant and light chain constant regions, respectively, such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel, Gene Expression Technology: Methods in Enzymology 185 (Academic Press, San Diego, Calif., 1990). It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al., and U.S. Pat. No. 4,968,615 by Schaffner et al.

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (See, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in $DHFR^-$ host cells with methotrexate selection/amplification) and the neo gene (for G418 selection). For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE- dextran transfection and the like.

It is possible to express the antibodies of the disclosure in either prokaryotic or eukaryotic host cells. In certain embodiments, expression of antibodies is performed in eukaryotic cells, e.g., mammalian host cells, of optimal secretion of a properly folded and immunologically active antibody. Exemplary mammalian host cells for expressing the recombinant antibodies of the disclosure include Chinese Hamster Ovary (CHO cells) (including $DHFR^-$ CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Host cells can also be used to produce portions of intact antibodies, such as Fab fragments or scFv molecules. It is understood that variations on the above procedure are within the scope of the present disclosure. For example, it can be desirable to transfect a host cell with DNA encoding either the light chain or the heavy chain (but not both) of an anti-hPG monoclonal antibody of this disclosure.

Recombinant DNA technology can also be used to remove some or all of the DNA encoding either or both of the light and heavy chains that is not necessary for binding to hPG. The molecules expressed from such truncated DNA molecules are also encompassed by the antibodies of the disclosure.

For recombinant expression of an anti-hPG monoclonal antibody of the disclosure, the host cell can be co-transfected with two expression vectors of the disclosure, the first vector encoding a heavy chain derived polypeptide and the second vector encoding a light chain derived polypeptide. The two vectors can contain identical selectable markers, or they can each contain a separate selectable marker. Alternatively, a single vector can be used which encodes both heavy and light chain polypeptides.

Once a nucleic acid encoding one or more portions of an anti-hPG monoclonal antibody, further alterations or mutations can be introduced into the coding sequence, for example to generate nucleic acids encoding antibodies with different CDR sequences, antibodies with reduced affinity to the Fc receptor, or antibodies of different subclasses.

The anti-hPG monoclonal antibodies of the disclosure can also be produced by chemical synthesis (e.g., by the methods described in Solid Phase Peptide Synthesis, $2^{nd}$ ed., 1984 The Pierce Chemical Co., Rockford, Ill.). Variant antibodies can also be generated using a cell-free platform (See, e.g., Chu et al., Biochemia No. 2, 2001 (Roche Molecular Biologicals).

Once an anti-hPG monoclonal antibody of the disclosure has been produced by recombinant expression, it can be purified by any method known in the art for purification of an immunoglobulin molecule, for example, by chromatography (e.g., ion exchange, affinity, and sizing column chromatography), centrifugation, differential solubility, or by any other standard technique for the purification of proteins. Further, the anti-hPG monoclonal antibodies of the present disclosure or fragments thereof can be fused to heterologous polypeptide sequences described herein or otherwise known in the art to facilitate purification.

Once isolated, the anti-hPG monoclonal antibody can, if desired, be further purified, e.g., by high performance liquid chromatography (See, e.g., Fisher, Laboratory Techniques In Biochemistry And Molecular Biology (Work and Burdon, eds., Elsevier, 1980), or by gel filtration chromatography on a SUPERDEX® 75 column (Pharmacia Biotech AB, Uppsala, Sweden).

The present disclosure provides host cells capable of producing anti-hPG monoclonal antibodies. Host cells can be cells engineered using recombinant DNA techniques to express genes encoding heavy and light chain genes or hybridomas derived from a suitable organism and selected for the ability to produce the desired antibodies.

Host cells capable of producing anti-PG monoclonal antibodies can be hybridomas. Methods for generating hybridomas are known in the art (see, e.g., Kohler and Milstein, 1975, Nature 256:495) and an example is provided below. Generally, a host animal, such as a mouse is immunized with an immunogen, such as a peptide of interest, to elicit the development of lymphocytes, for example spleen cells, that produce antibodies capable of specifically binding the immunogen. Alternatively, isolated lymphocytes, including spleen cells, lymph node cells, or peripheral blood lymphocytes, can be immunized in vitro. Lymphocytes are then fused with an immortalized cell line, such as a myeloma cell line, using a suitable fusing agent (e.g., polyethylene glycol), to form a hybridoma cell line. Suitable immortalized cell lines can be of mammalian origin, such as murine, bovine, or human. Hybridoma cells are then cultured in any suitable medium that contains one or more substances that inhibit growth or survival of the unfused, immortalized cells. For example, when parental cells lacking the enzyme hypoxanthine guanine phosphoribosyl transferase (HGPRT or HPRT) are used, fusions can be grown in medium containing hypoxanthine, aminopterin, and thymidine ("HAT" medium) which inhibits the growth of parental, unfused cells.

In some embodiments, the N-terminal anti-hPG monoclonal antibodies have variable light chain ($V_L$) CDRs that correspond to the $V_L$ of the monoclonal antibody obtainable from hybridomas 43B9G11 (producing anti-hPG MAb 1), WE5H2G7 (producing anti-hPG MAb 2), 6B5B11C10 (producing anti-hPG MAb 3), 20D2C3G2 (producing anti-hPG MAb 4), 1E9A4A4 (producing anti-hPG MAb 15), 1E9D9B6 (producing anti-hPG MAb 16), 1C8D10F5 (producing anti-hPG MAb 17), 1A7C3F11 (producing anti-hPG MAb 18), 1B3B4F11 (producing anti-hPG MAb 19), and 1C11F5E8 (producing anti-hPG MAb 20).

In some embodiments, the N-terminal anti-hPG monoclonal antibodies have $V_H$ CDRs that correspond to the $V_H$ CDRs of the monoclonal antibodies obtainable from the above hybridomas.

In some embodiments, the C-terminal anti-hPG monoclonal antibodies have $V_L$ CDRs that correspond to the $V_L$ of the monoclonal antibody obtainable from hybridomas 1B4A11D11 (producing anti-hPG MAb 5), 1B6A11F2 (producing anti-hPG MAb 6), 1B11E4B11 (producing anti-hPG MAb 7), 1C10D3B9 (producing anti-hPG MAb 8), 1D8F5B3 (producing anti-hPG MAb 9), 1E1C7B4 (producing anti-hPG MAb 10), 2B4C8C8 (producing anti-hPG MAb 11), 2B11E6G4 (producing anti-hPG MAb 12), 2C6C3C7 (producing anti-hPG MAb 13), 2H9F4B7 (producing anti-hPG MAb 14), 1F11F5E10 (producing anti-hPG MAb 21), 1F11F5G9 (producing anti-hPG MAb 22), and 1A11F2C9 (producing anti-hPG MAb 23).

In some embodiments, the C-terminal anti-hPG monoclonal antibodies have $V_H$ CDRs that correspond to the $V_H$ CDRs of the monoclonal antibodies obtainable from the above hybridomas.

In an embodiment, a host cell capable of producing an anti-hPG antibody comprising a heavy chain variable region comprising SEQ ID NO:12 and a light chain variable region comprising SEQ ID NO:13 is provided. In an embodiment, a host cell capable of producing an anti-hPG antibody comprising a heavy chain variable region comprising SEQ ID NO:14 and a light chain variable region comprising SEQ ID NO:15 is provided. In an embodiment, a host cell capable of producing an anti-hPG antibody comprising a heavy chain variable region comprising SEQ ID NO:59 and a light chain variable region comprising SEQ ID NO:63 is provided. In an embodiment, a host cell capable of producing an anti-hPG antibody comprising a heavy chain variable region comprising SEQ ID NO:60 and a light chain variable region comprising SEQ ID NO:64 is provided. In an embodiment, a host cell capable of producing an anti-hPG antibody comprising a heavy chain variable region comprising SEQ ID NO:61 and a light chain variable region comprising SEQ ID NO:65 is provided. In an embodiment, a host cell capable of producing an anti-hPG antibody comprising a heavy chain variable region comprising SEQ ID NO:62 and a light chain variable region comprising SEQ ID NO:66 is provided.

In some embodiments, a host cell of the disclosure comprises a nucleic acid selected from: a nucleotide sequence encoding the heavy chain variable region polypeptide of SEQ ID NOs:12, 14, 59, 60, 61, and 62; and a nucleic acid selected from: a nucleotide sequence encoding the light chain variable region polypeptide of SEQ ID NOs:13, 15, 63, 64, 65, and 66. In some embodiments, the heavy chain variable region is encoded by a nucleic acid sequence selected from: SEQ ID NOs:16, 18, 67, 68, 69 and 70. In some embodiments, the light chain variable region is encoded by a nucleic acid sequence selected from: SEQ ID NOs:17, 19, 71, 72, 73, and 74.

In some embodiments, polynucleotide sequences are provided encoding a heavy chain variable region of a humanized anti-hPG monoclonal antibody. Specific embodiments include polynucleotides encoding a polypeptide having an amino acid sequence selected from the group consisting of SEQ ID NO:21, 23, 75, 77, 79, 80, 82, 84, 86, 88, 90, 92, and 94. In some embodiments, polynucleotide sequences are provided encoding a light chain variable region of a humanized anti-hPG monoclonal antibody. Specific embodiments include polynucleotides encoding a polypeptide having an amino acid sequence selected from the group consisting of SEQ ID NO:22, 24, 76, 78, 81, 83, 85, 87, 89, 91, 93, and 95.

Biological Activities of Anti-hPG Monoclonal Antibodies

PG has been implicated in CRC tumor cell survival and/or proliferation. As described above in the Detailed Description, neutralizing anti-PG monoclonal antibodies are thought to block or inhibit PG's ability to interact with its signaling partner(s). As a consequence of these activities, neutralizing anti-hPG monoclonal antibodies of the disclosure can be used in a variety of in vitro, in vivo, and ex vivo contexts to bind PG and block PG-dependent signaling.

Accordingly, the disclosure provides methods of inhibiting PG-dependent responses in CRC cells. Generally, the methods comprise contacting a CRC cell with, or exposing a cell population to, a neutralizing anti-PG monoclonal antibody in an amount effective to inhibit one or more PG-induced responses of CRC cells, e.g. proliferation and/or survival of CRC cells. Proliferation, or inhibition thereof, in vitro and in vivo can be determined according to assays for measuring increases in cell number, tumor number, or tumor size over time. Assays for inhibition of proliferation of cells and tumors are well known in the art.

Blocking PG-dependent signaling can inhibit survival of CRC cells by increasing cell death. Inhibition of CRC cell survival in vitro or in vivo can be determined by measuring reduction of live cancer cell numbers over time (e.g., 24 or 48 hours). Assays for cell death are well known in the art. Additionally, an example of a cell survival assay is provided herein.

Studies further suggest that inhibiting PG-dependent signaling in CRC tumor cells can inhibit survival of CRC cells by trigger programmed cell death, or apoptosis. Induction of apoptosis can be determined by any means known in the art, including but not limited to, measuring changes in expression of genes having pro- or anti-apoptotic activity. For example, an increase in expression over time (e.g., 48 hours) of a pro-apoptotic gene, such as, for example, Bax, is indicative of an increase in apoptosis. Similarly, a decrease in expression over time (e.g., 72 or 96 hours) of an anti-apoptotic gene, such as, for example, but not by way of limitation, Bcl-2, is indicative of an increase in apoptosis. Techniques for measuring changes in gene expression, such as real-time quantitative PCR, are well known in the art. See, e.g., Hollande et al., WO 2007/135542.

Inhibition of progastrin-dependent signaling also stimulates cell differentiation. Accordingly, methods of inhibiting proliferation and/or survival of CRC cells comprise administering an amount of a neutralizing anti-PG monoclonal antibody effective to induce differentiation of CRC cells in vitro or in vivo. Differentiation of CRC cells can be determined by measuring increases over time (e.g., 24 or 48 hours) in expression of genetic markers for cellular differentiation, such as, for example, but not by way of limitation, Muc-2 or other markers for differentiated intestinal cells (e.g., goblet cells). Changes in gene expression can be measured by any means known in the art. See, e.g., Hollande et al., WO 2007/135542. Other genes whose expression or repression is dependent on PG, such as ICAT, can also be assayed using standard methods. See id.

Pharmaceutical Compositions

Anti-PG monoclonal antibodies can be formulated in compositions. Optionally, the compositions can comprise one or more additional therapeutic agents, such as the second therapeutic agents described below, are provided herein. The compositions will usually be supplied as part of a sterile, pharmaceutical composition that will normally include a pharmaceutically acceptable carrier. This composition can be in any suitable form (depending upon the desired method of administering it to a patient).

The anti-hPG monoclonal antibodies of the disclosure can be administered to a patient by a variety of routes such as orally, transdermally, subcutaneously, intranasally, intravenously, intramuscularly, intraocularly, topically, intrathecally and intracerebroventricularly. The most suitable route for administration in any given case will depend on the particular antibody, the subject, and the nature and severity of the disease and the physical condition of the subject. The antibody can be formulated as an aqueous solution and administered by subcutaneous injection.

Pharmaceutical compositions can be conveniently presented in unit dose forms containing a predetermined amount of an anti-hPG monoclonal antibody of the disclosure per dose. Such a unit can contain for example but without limitation 5 mg to 5 g, for example 10 mg to 1 g, or 20 to 50 mg. Pharmaceutically acceptable carriers for use in the disclosure can take a wide variety of forms depending, e.g., on the condition to be treated or route of administration.

Pharmaceutical compositions of the disclosure can be prepared for storage as lyophilized formulations or aqueous solutions by mixing the antibody having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives must be nontoxic to the recipients at the dosages and concentrations employed.

Buffering agents help to maintain the pH in the range which approximates physiological conditions. They can be present at concentration ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188, etc.), Pluronic polyols, polyoxyethylene sorbitan monoethers (TWEEN®-20, TWEEN®-80, etc.). Non-ionic surfactants can be present in a range of about 0.05 mg/ml to about 1.0 mg/ml, for example about 0.07 mg/ml to about 0.2 mg/ml.

Additional miscellaneous excipients include bulking agents (e.g., starch), chelating agents (e.g., EDTA), antioxidants (e.g., ascorbic acid, methionine, vitamin E), and cosolvents.

Anti-PG monoclonal antibodies can be administered singly, as mixtures of one or more anti-PG monoclonal antibodies, in mixture or combination with other agents useful for treating CRC, or adjunctive to other therapy for CRC. Examples of suitable combination and adjunctive therapies are provided below.

Encompassed by the present disclosure are pharmaceutical kits containing neutralizing anti-hPG monoclonal antibodies (including antibody conjugates) of the disclosure. The pharmaceutical kit is a package comprising a neutralizing anti-hPG monoclonal antibody (e.g., either in lyophilized form or as an aqueous solution) and one or more of the following:

- A second therapeutic agent, for example as described below;
- A device for administering the anti-hPG monoclonal antibody, for example a pen, needle and/or syringe; and
- Pharmaceutical grade water or buffer to resuspend the antibody if the antibody is in lyophilized form.

Each unit dose of the anti-hPG monoclonal antibody can be packaged separately, and a kit can contain one or more unit doses (e.g., two unit doses, three unit doses, four unit doses, five unit doses, eight unit doses, ten unit doses, or more). In a specific embodiment, the one or more unit doses are each housed in a syringe or pen.

Effective Dosages

Neutralizing anti-PG monoclonal antibodies, or compositions thereof, will generally be used in an amount effective to achieve the intended result, for example an amount effective to treat CRC in a subject in need thereof. Pharmaceutical compositions comprising neutralizing anti-PG monoclonal antibodies can be administered to patients (e.g., human subjects) at therapeutically effective dosages. As used herein, a "therapeutically effective" dosage is an amount that confers a therapeutic benefit. In the context of CRC therapy, a therapeutic benefit means any amelioration of CRC, including any one of, or combination of, halting or slowing the progression of CRC (e.g., from one stage of colorectal cancer to the next), halting or delaying aggravation or deterioration of the symptoms or signs of CRC, reducing the severity of CRC, inducing remission of CRC, inhibiting CRC tumor cell proliferation, CRC tumor size, or CRC tumor number, or reducing PG serum levels.

The amount of neutralizing anti-PG monoclonal antibody administered will depend on a variety of factors, including the nature and stage of the CRC being treated, the form, route and site of administration, the therapeutic regimen (e.g., whether a second therapeutic agent is used), the age and condition of the particular subject being treated, the sensitivity of the patient being treated to anti-PG monoclonal antibodies. The appropriate dosage can be readily determined by a person skilled in the art. Ultimately, a physician will determine appropriate dosages to be used. This dosage can be repeated as often as appropriate. If side effects develop the amount and/or frequency of the dosage can be altered or reduced, in accordance with normal clinical practice. The proper dosage and treatment regimen can be established by monitoring the progress of therapy using conventional techniques known to the people skilled of the art.

Effective dosages can be estimated initially from in vitro assays. For example, an initial dose for use in animals may be formulated to achieve a circulating blood or serum concentration of anti-PG monoclonal antibody that is at or above the binding affinity of the antibody for progastrin as measured in vitro. Calculating dosages to achieve such circulating blood or serum concentrations taking into account the bioavailability of the particular antibody is well within the capabilities of skilled artisans. For guidance, the reader is referred to Fingl & Woodbury, "General Principles" in *Goodman and Gilman's The Pharmaceutical Basis of Therapeutics*, Chapter 1, latest edition, Pagamonon Press, and the references cited therein.

Initial dosages can be estimated from in vivo data, such as animal models. Animal models useful for testing the efficacy of compounds to treat CRC are well known in the art. Additionally, animal models of CRC are described in the Examples below. Ordinarily skilled artisans can routinely adapt such information to determine dosages suitable for human administration.

The effective dose of a neutralizing anti-hPG monoclonal antibody of the disclosure can range from about 0.001 to about 75 mg/kg per single (e.g., bolus) administration, multiple administrations or continuous administration, or to achieve a serum concentration of 0.01-5000 μg/ml serum concentration per single (e.g., bolus) administration, multiple administrations or continuous administration, or any effective range or value therein depending on the condition being treated, the route of administration and the age, weight and condition of the subject. In a certain embodiment, each dose can range from about 0.5 μg to about 50 μg per kilogram of body weight, for example from about 3 μg to about 30 μg per kilogram body weight.

Amount, frequency, and duration of administration will depend on a variety of factors, such as the patient's age, weight, and disease condition. A therapeutic regimen for administration can continue for 2 weeks to indefinitely, for 2 weeks to 6 months, from 3 months to 5 years, from 6 months to 1 or 2 years, from 8 months to 18 months, or the like. Optionally, the therapeutic regimen provides for repeated administration, e.g., once daily, twice daily, every two days, three days, five days, one week, two weeks, or one month. The repeated administration can be at the same dose or at a different dose. The administration can be repeated once, twice, three times, four times, five times, six times, seven times, eight times, nine times, ten times, or more. A therapeutically effective amount of anti-hPG monoclonal antibody can be administered as a single dose or over the course of a therapeutic regimen, e.g., over the course of a week, two weeks, three weeks, one month, three months, six months, one year, or longer.

Therapeutic Methods

The ability of neutralizing anti-hPG monoclonal antibodies of the present disclosure to block PG-dependent responses, including cell proliferation, makes them useful for treating colorectal cancer. Accordingly, in another aspect, the present disclosure provides methods of treating CRC in a patient in need thereof. Generally, the methods comprise administering to the patient a therapeutically effective amount of a neutralizing anti-hPG monoclonal antibody of the disclosure.

A "subject" or "patient" to whom the anti-hPG monoclonal antibody of the disclosure is administered is preferably a mammal such as a non-primate (e.g., cow, pig, horse, cat, dog, rat, etc.) or a primate (e.g., monkey or human). The subject or patient can be a human, such as an adult patient or a pediatric patient.

Patients suitable for anti-hPG monoclonal antibody therapy are patients diagnosed with CRC. The CRC can be of any type and at any clinical stage or manifestation. Suitable subjects include patients with CRC tumors (operable or inoperable), patients whose tumors have been surgically removed or resected, patients with a CRC tumor comprising cells carrying a mutation in an oncogene, such as, for example, RAS or APC, patients who have received or receive other therapy for CRC in combination with or adjunctive to anti-hPG monoclonal antibody therapy. Other therapy for CRC includes, but is not limited to, chemotherapeutic treatment, radiation therapy, surgical resection, and treatment with one or more other therapeutic antibodies, as detailed below.

Anti-hPG monoclonal antibody therapy can be combined with, or adjunctive to, one or more other treatments. Other treatments include, without limitation, chemotherapeutic treatment, radiation therapy, surgical resection, and antibody therapy, as described herein.

Anti-hPG monoclonal antibody therapy can be adjunctive to other treatment, including surgical resection.

Combination therapy as provided herein involves the administration of at least two agents to a patient, the first of which is a neutralizing anti-hPG monoclonal antibody of the disclosure, and the second of which is a second therapeutic agent. The neutralizing anti-hPG monoclonal antibody and the second therapeutic agent can be administered simultaneously, successively, or separately.

As used herein, the neutralizing anti-hPG monoclonal antibody and the second therapeutic agent are said to be administered successively if they are administered to the patient on the same day, for example during the same patient visit. Successive administration can occur 1, 2, 3, 4, 5, 6, 7 or 8 hours apart. In contrast, the anti-hPG monoclonal antibody of the disclosure and the second therapeutic agent are said to be administered separately if they are administered to the patient on the different days, for example, the anti-hPG monoclonal antibody of the disclosure and the second therapeutic agent can be administered at a 1-day, 2-day or 3-day, one-week, 2-week or monthly intervals. In the methods of the present disclosure, administration of the anti-hPG monoclonal antibody of the disclosure can precede or follow administration of the second therapeutic agent.

As a non-limiting example, the neutralizing anti-hPG monoclonal antibody and second therapeutic agent can be administered concurrently for a period of time, followed by a second period of time in which the administration of the anti-hPG monoclonal antibody of the disclosure and the second therapeutic agent is alternated.

Combination therapies of the present disclosure can result in a greater than additive, or a synergistic, effect, providing therapeutic benefits where neither the neutralizing anti-hPG monoclonal antibody nor second therapeutic agent is administered in an amount that is, alone, therapeutically effective. Thus, such agents can be administered in lower amounts, reducing the possibility and/or severity of adverse effects.

A second therapeutic agent can be a chemotherapeutic agent. Chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), anti-mitotic agents, cis-dichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, CYTOXAN®, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, emetine, epoetin-α, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, oxaliplatin, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, TAXOL®, tegafur, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate The neutralizing anti-hPG monoclonal antibodies disclosed herein can be administered to a patient in need of treatment for colorectal cancer receiving a combination of chemotherapeutic agents. Exemplary combinations of chemotherapeutic agents include 5-fluorouracil (5FU) in combination with leucovorin (folinic acid or LV); capecitabine, in combination with uracil (UFT) and leucovorin; tegafur in combination with uracil (UFT) and leucovorin; oxaliplatin in combination with 5FU, or in combination with capecitabine; irinotecan in combination with capecitabine, mitomycin C in combination with 5FU, irinotecan or capecitabine. Use of other combinations of chemotherapeutic agents disclosed herein is also possible.

As is known in the relevant art, chemotherapy regimes for colorectal cancer using combinations of different chemotherapeutic agents have been standardized in clinical trials. Such regimes are often known by acronyms and include 5FU Mayo, 5FU Roswell Park, LVFU2, FOLFOX, FOLFOX4, FOLFOX6, bFOL, FUFOX, FOLFIRI, IFL, XELOX, CAPDX, XELIRI, CAPIRI, FOLFOXIRI. See, e.g., Chau, I., et al., 2009, Br. J. Cancer 100:1704-19 and Field, K., et al., 2007, World J. Gastroenterol. 13:3806-15, both of which are incorporated by reference.

Neutralizing anti-hPG monoclonal antibodies can also be combined with other therapeutic antibodies. Accordingly, anti-hPG monoclonal antibody therapy can be combined with, or administered adjunctive to a different monoclonal antibody such as, for example, but not by way of limitation, an anti-EGFR (EGF receptor) monoclonal antibody or an anti-VEGF monoclonal antibody. Specific examples of anti-EGFR antibodies include cetuximab and panitumumab. A specific example of an anti-VEGF antibody is bevacizumab.

Detection of Progastrin Using Anti-hPG Antibodies

Anti-PG monoclonal antibodies, whether neutralizing or non-neutralizing, are also useful for applications that depend on PG detection such as diagnosing CRC or monitoring the effects of treatment on a subject's CRC. Accordingly, in an aspect, the present disclosure provides a method of diagnosing colorectal cancer in a patient, comprising determining the amount of progastrin in a sample from the patient using an anti-hPG monoclonal antibody according to the present disclosure. Generally, methods of diagnosing colorectal cancer in a patient comprise measuring progastrin in a sample obtained from a patient using the anti-hPG monoclonal antibodies of the disclosure, wherein a measurement of 20 pM to 400 pM of progastrin in the sample is indicative of colorectal cancer. Progastrin can be measured in samples of, e.g., blood, serum, plasma, tissue, and/or cells. hPG detection can be carried out using assays known in the art and/or described herein, such as, ELISA, sandwich ELISA, immunoblotting (Western blotting), immunoprecipitation, BIACORE® technology and the like.

As noted herein, progastrin is but one of a number of different polypeptides resulting from post-translational processing of the gastrin gene product. Diagnostic, monitoring and other methods described herein specifically detect hPG as opposed to other gastrin gene products, including degradation products. Accordingly, in specific embodiments, hPG is detected using an ELISA as disclosed herein, wherein two antibodies to hPG are used, targeting the N- and C-terminus of hPG respectively. In some embodiments, one of the two antibodies used for detection is an anti-hPG monoclonal antibody as described herein. hPG levels ranging from 20 pM to 400 pM are indicative of colorectal cancer.

In general, the procedure for determining hPG levels using anti-hPG monoclonal antibodies is as follows. A surface, such as the wells in a 96-well plate, is prepared to which a known quantity of a first, "capture," antibody to hPG is bound. The capture antibody can be, for example, an anti-hPG antibody which binds with to a C- or N-terminal region of hPG. After blocking, a test sample is applied to the surface followed by an incubation period. The surface is then washed to remove unbound antigen and a solution containing a second, "detection," antibody to hPG is applied. The detection antibody can be any of the anti-hPG monoclonal antibodies described herein, provided the detection antibody binds a different epitope from the capture antibody. For example, if the capture antibody binds a C-terminal peptide region of hPG, then a suitable detection antibody would be one that binds an N-terminal peptide region of hPG. Progastrin levels can then be detected either directly (if, for example, the detection antibody is conjugated to a detectable label) or indirectly (through a labeled secondary antibody that binds the detection anti-hPG antibody).

In a specific embodiment, hPG levels are measured as follows from a test sample. 96-well microtiter plates are coated with between 0.5 and 10 μg/mL of a rabbit C-terminal anti-hPG polyclonal antibody and incubated overnight. Plates are then washed three times in PBS-TWEEN® (0.05%) and blocked with 2% (w/v) nonfat dried milk in PBS-TWEEN® (0.05%). Separately, test samples, control samples (blank or PG-negative plasma or serum samples), and between about 5 pM ($0.5\times10^{-11}$ M) and about 0.1 nM ($1\times10^{-10}$ M) of an hPG reference standard (lyophilized hPG diluted in PG-negative plasma or serum) are prepared in an appropriate diluent (e.g., PBS-TWEEN® 0.05%). Samples are incubated on the coated plates for between 2 and 4 hours at 37° C., or alternatively between 12 and 16 hours at 21° C. After incubation, plates are washed three times with PBS-TWEEN® (0.05%) and incubated with between 0.001 and 0.1 μg/mL of an N-terminal anti-hPG monoclonal antibody as described herein, coupled to horseradish peroxidase (HRP) (Nakane et al., 1974, J. Histochem. Cytochem. 22(12): 1084-1091) for 30 minutes at 21° C. Plates are then washed three times in PBS-TWEEN® (0.05%) and HRP substrate is added for 15 minutes at 21° C. The reaction is stopped by added 100 μL of 0.5M sulfuric acid and an optical density measurement taken at 405 nm. Test sample hPG levels are determined by comparison to a standard curve constructed from the measurements derived from the hPG reference standard.

Typically, patients are diagnosed based on invasive procedures such as histological assessment of biopsied tissue as well as other invasive procedures such as colonoscopy. CRC is divided into 5 stages ranging from Stage 0 (cancer limited to innermost lining of colon or rectum), Stage 1 (cancer in inner wall of colon or rectum), Stage 2 (cancer extended through wall of colon but not found in adjacent lymph nodes), Stage 3 (cancer found in lymph nodes and tissue surrounding colon or rectum), and Stage 4 (cancer has spread to other parts of the body). From a histological perspective, colorectal tumors present with a broad spectrum of neoplasms, ranging from benign growths to invasive cancer, and are predominantly epithelial-derived tumors (i.e., adenomas or adenocarcinomas). Lesions can be classified into three groups: nonneoplastic polyps, neoplastic polyps (adenomatous polyps, adenomas), and cancers. Adenomatous polyps are benign tumors that may undergo malignant transformation, and have been classified into three histologic types, with increasing malignant potential: tubular, tubulovillous, and villous. Adenocarcinomas have also been categorized according to their histology into mucinous (colloid) adenocarcinoma; signet ring adenocarcinoma; scirrhous tumors; and neuroendocrine.

In contrast to current means for diagnosing CRC, the present disclosure provides methods for diagnosing subjects with CRC in the absence of any histological analysis or disease staging, based on measurement of hPG levels that can be determined from a blood sample. Furthermore, methods of the present disclosure are useful in selecting CRC patients suited to anti-hPG monoclonal therapy regardless of how a patient has been diagnosed.

Serum PG levels are also useful in assessing efficacy of CRC treatment. Accordingly, the present disclosure provides a method for monitoring the effectiveness of colorectal cancer therapy comprising determining PG levels in a patient being treated for CRC. Methods for monitoring the effectiveness of colorectal cancer therapy comprise repeatedly determining hPG levels using an anti-PG monoclonal antibody of the present disclosure in a colorectal cancer patient undergoing treatment for colorectal cancer, wherein a decrease in the patient's circulating hPG levels over an interval of treatment is indicative of treatment efficacy. For example, a first measurement of a patient's circulating hPG levels can be taken followed by a second measurement while or after the patient receives treatment for colorectal cancer. The two measurements are then compared, and a decrease in hPG levels is indicative of therapeutic benefit.

In an aspect, the disclosure provides diagnostic kits containing the anti-hPG monoclonal antibodies (including antibody conjugates). The diagnostic kit is a package comprising at least one anti-hPG monoclonal antibody of the disclosure (e.g., either in lyophilized form or as an aqueous solution) and one or more reagents useful for performing a diagnostic assay (e.g., diluents, a labeled antibody that binds to an anti-hPG monoclonal antibody, an appropriate substrate for the labeled antibody, hPG in a form appropriate for use as a positive control and reference standard, a negative control). In specific embodiments, a kit comprises two anti-hPG antibodies, wherein at least one of the antibodies is an anti-hPG monoclonal antibody. Optionally, the second antibody is a polyclonal anti-hPG antibody. In some embodiments, the kit of the present disclosure comprises an N-terminal anti-hPG monoclonal antibody as described herein.

Anti-hPG antibodies can be labeled, as described above. Alternatively, the kit can include a labeled antibody which binds an anti-hPG monoclonal antibody and is conjugated to an enzyme. Where the anti-hPG monoclonal antibody or other antibody is conjugated to an enzyme for detection, the kit can include substrates and cofactors required by the enzyme (e.g., a substrate precursor which provides the detectable chromophore or fluorophore). In addition, other additives can be included, such as stabilizers, buffers (e.g., a block buffer or lysis buffer), and the like. Anti-hPG monoclonal antibodies included in a diagnostic kit can be immobilized on a solid surface, or, alternatively, a solid surface (e.g., a slide) on which the antibody can be immobilized is included in the kit. The relative amounts of the various reagents can be varied widely to provide for concentrations in solution of the reagents which substantially optimize the sensitivity of the assay. Antibodies and other reagents can be provided (individually or combined) as dry powders, usually lyophilized, including excipients which on dissolution will provide a reagent solution having the appropriate concentration.

Kits may include instructional materials containing instructions (e.g., protocols) for the practice of diagnostic methods. While the instructional materials typically comprise written or printed materials, they are not limited to such. A medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. Such media may include addresses to internet sites that provide such instructional materials.

10. EXAMPLES

The following examples are illustrative and not intended to be limiting.

Example 1: Generation of Monoclonal Antibodies Against Progastrin

Immunogens for Human Progastrin

Several immunogens were generated to develop hybridomas producing monoclonal antibodies against human progastrin. Antigens previously used to generate polyclonal antibodies, such as full length human progastrin and immunogens based on residues 70 to 80 of hPG, failed to lead to a monoclonal immune response or give rise to PG-specific monoclonal antibodies. As described in more detail below, antigens 14 amino acids and longer, which included sequences unique to hPG at either the N-terminal and C-terminal end of the protein, were capable of inducing an adequate immune response in animals and were used to generate hybridomas producing over 20 different monoclonal antibodies to hPG. Surprisingly, several immunogens that included residues 55 to 80 of hPG, some of which are also found in other gastrin gene-derived peptides, was used successfully to generate monoclonal antibodies that were specific to hPG. The table below summarizes the immunogens tested.

TABLE 2

| Experiment | Immunogen | No. of positive clones |
|---|---|---|
| 1 | Human progastrin (SEQ ID NO: 20) | 0* |
| 1 | (SEQ ED NO: 26)-Ahx-Cys-BSA | 2 |
| 2 | (SEQ ED NO: 26)-Ahx-Cys-KLH | 2 |
| 3 | (SEQ ED NO: 26)-Ahx-Cys-KLH | 8 |
| 1 | BSA-Cys-Ahx-Ahx-(SEQ ID NO: 97) | 0 |
| 2 | KLH-Cys-Ahx-Ahx-(SEQ ID NO: 97) | 0 |
| 3 | KLH-Cys-Ahx-Ahx-(SEQ ID NO: 96) | 10 |
|  | DT-Cys-Ahx-Ahx-(SEQ ID NO: 96) | 3 |

*The immunized mice did not display any immune response.

The immunogens listed in Table 2 were made according to techniques known in the art, using chemical synthesis of the peptide sequence and the linker, followed by crosslinking to the Bovine Serum Albumin (BSA), Keyhole Limpet Hemocyanin (KLH), or Diptheria Toxin (DT) carrier using an appropriate crosslinking agent (e.g., MBS (m-Maleimidobenzoyl-N-hydrosuccinimide ester), glutaraldehyde or Sulfo-SMCC (Sulfosuccinimidyl 4-[N-maleimidomethyl] cycolhexane-1-carboxylate). (Coligan J E et al., Current protocols in Immunology, Vol. 2, New York: John Wiley and Sons; 1996, p 9.0.1-9.0.15; Harlow D L. Antibodies: A Laboratory Manual. New York: Cold Spring Harbor Laboratory; 1998, p 72-87). Linkers used were one or two aminohexanoic acid (Ahx) residues coupled to a cysteine residue.

In each of three experiments, Balb/c mice were injected 4 to 5 times for N-terminal immunogens, and 2 to 4 times for C-terminal immunogens. Each injection administered 10 μg of the immunogen with Ribi, Alun or Freund's adjuvant.

Cell Fusions and Hybridoma Screening

Serum from each mouse was tested by ELISA against the immunogen and splenocytes harvested from the mice with the strongest immune response. Splenocytes were fused with Sp2 myeloma cells using polyethylene glycol, and seeded into 96-well plates at a density of 15,000 to 35,000 cells per well. Fused cells were selected for, using medium containing hypoxanthine, aminopterin, and thymidine (HAT medium).

Supernatants of hybridomas were screened by ELISA for the ability to bind the immunogen and full length progastrin. Three rounds of screening were performed to ensure that only hybridomas stably producing antibodies recognizing full length hPG and the immunogen were selected.

Screening of hybridomas and monoclonal antibodies to determine binding to different PG peptides was performed using an ELISA technique as described below. This protocol was used to screen for PG binding of fused splenocytes, first and second round sub-clones, as well as for verifying the specificity of the antibodies to PG, as compared to other gastrin gene-derived peptides.

Briefly, 96-well plates were incubated overnight at 4° C. with appropriate concentration(s) of a test peptide in Phosphate-Buffered Saline (PBS), after which the wells were washed three times with wash solution (PBS and 0.1% TWEEN®-20), and incubated for 2 hours at 22° C. with 100 μL blocking solution (PBS, 0.1% TWEEN®-20, 0.1% Bovine Serum Albumin or casein hydrolysate) per well. After blocking, the wells were washed three times and the primary antibody—the antibody to be assayed—added. For initial screening of fused splenocytes, 50 μL of culture supernatant from each culture to be assayed was added to each well in the plate. In assays performed on monoclonal antibodies, 100 μL of the test antibody in PBS and 0.1% TWEEN®-20 was added to each well. Plates were then incubated for 2 hours at 22° C., after which the primary antibody solution was discarded and replaced, after a wash step (3×100 μL wash solution, as noted above), with blocking solution containing the secondary antibody, which binds the primary antibody and is coupled to an enzyme. The secondary antibody was a goat anti-mouse IgG (Fc) antibody coupled to horseradish peroxidase. After a 1-hour incubation with secondary antibody, 100 μL of substrate solution (e.g. Fast OPD, or O-Phenylenediamine dihydrochloride, available from Sigma-Aldrich Co., prepared according to manufacturer's directions) was added to each well and incubated in the dark for 20 minutes at 22° C. The reaction was then stopped by adding 50 μL of 4N sulfuric acid and the amount of substrate catalyzed determined by measuring the optical density (O.D.) at 492 nm. Substrate conversion is proportional to the amount of primary (test) antibody bound to the antigen. Experiments were run in duplicate and OD measurements plotted as a function of antigen or antibody concentration depending on the goal of the experiment. Samples were scored as positive for anti-PG antibodies if the measured O.D. was between 0.2 and 1.5. The same O.D. bracket was used to identify antibodies that bound the immunogenic peptide used to inoculate test animals.

Exemplary materials and reagents used in the assay are as follows:

| Item | Source | Reference |
|---|---|---|
| Greiner Microlon 96-well plates | Dutscher | # 655092 |
| 10X DPBS | Dutscher | # P04-53500 |
| Tween-20 | Sigma | # 63158 |

-continued

| Item | Source | Reference |
|---|---|---|
| BSA (for blocking) | Euromedex | # 04-100-810-C |
| Hydrolyzed casein (when used instead of BSA) | Sigma | 22090 |
| Hybridoma supernatants or N-terminal or C-terminal monoclonal antibodies | BioRéalités | As described herein |
| Goat anti-mouse IgG (Fc), peroxidase-coupled | Thermo | # 31439 |
| Fast OPD | Sigma | # P9187 |
| 95-97% Sulfuric Acid | Sigma | # 30743 |

Exemplary peptides used in screening of hybridomas and monoclonal antibodies were as follows:

| Screening peptides | Source | Reference |
|---|---|---|
| BSA | Euromedex | # 04-100-810-0 |
| Recombinant human progastrin | BioRéalités | McQueen et al., 2002, J. Protein Chem., 21(7): 465-471. |
| Human gastrin I (G-17) | Sigma | # 53673 |
| Glycine-extended gastrin 17 (G-Gly) | Auspep | # B10082 |
| KLH | Pierce (Perbio) | # 77653 |
| C-terminal flanking peptide (CTFP) | Auspep | # R41345 |

Recombinant human progastrin was produced as described in McQueen et al, 2002, J. Protein Chem. 21: 465-471) with minor modifications. Briefly, BL21 DE3 Star bacterial cells (InVitrogen) were transformed with a vector containing the full-length human progastrin sequence in a PGEX-GST-TEV backbone (GE Healthcare). Bacteria were grown in LB medium containing 0.5 mM IPTG for 3 hours at 37° C. Bacterial pellets were broken using a French Press, and soluble as well as non-soluble fractions were separated by centrifugation. Thereafter, GST-tagged hPG was isolated using a glutathione affinity column and PG was cleaved from GST with the Tobacco Etch Virus NIa (TEV) protease. Finally, PG was dialyzed against the final buffer (10 mM Hepes, 0.5% BSA, pH 7.4).

Hybridomas were first cloned, then subcloned and amplified. Positive hybridomas were selected based on the following criteria: (1) PG and immunogen specificity, (2) relative affinity of antibodies, (3) hybridoma cell growth, (4) antibody secretion, and (5) monoclonality of hybridomas. Assays and selection criteria were as follows.

For specificity, supernatants of test hybridomas were assayed by ELISA as described above (50 μL of a 1 in 2 dilution of supernatant into assay medium PBS). Hybridomas were scored as positive if the O.D. measurement was between 0.2 and 1.5 in an assay with hPG or the immunogen used to inoculate test mice. As a further criterion for specificity, clones were selected based on a lack of binding to other gastrin gene-derived peptides. Lack of binding was measured as no statistically significantly difference between the signal from test wells and the average signal from control wells containing only PBS.

For affinity characterization, serial dilutions of antibodies were assayed by ELISA for binding to hPG, as described above. Standard dilutions used in assays of N-terminal antibodies were 0, 0.1, 0.3, 1, 3, 10, 30, 100 ng/ml. Standard dilutions used in assays of C-terminal antibodies were 0, 0.03, 0.1, 0.3, 1, 3, 10, 30 ng/ml.

Hybridoma cell growth through multiple rounds of serial culture was assessed by microscopic observation two days after seeding. Cells are expected to proliferate and fill the well by 48 hours after seeding. Serial dilution (typically, a first dilution at 1:5, followed by at least 2 further dilutions at 1:10) was performed, followed by microscopic observation at 48 hours to confirm adequate growth. Cells from hybridomas that fulfill this criterion were diluted and seeded again, to be observed under the microscope 48 h later. Such rounds of "dilution-seeding-observation" were repeated 3 times before a hybridoma was scored as fulfilling the "growth" criteria.

Antibody secretion was tested by performing ELISAs using hPG as described above on serial dilutions (1/2, 1/20, 1/200, 1/500, 1/1000, 1/2000) of cell-free supernatants.

Monoclonality was determined by seeding a clone or hybridoma in a 96-well plate at a density of 0.6 cells/well and incubating for two weeks. At two weeks, supernatants were assayed for hPG binding by ELISA and the clonal nature of the population determined based on having a consistent OD value across at least 90% of live-cell containing wells.

Monoclonal Antibodies Against Full Length Progastrin

Each of three mice was inoculated with recombinant human progastrin (described above). The immunogen failed to elicit any detectable immune response in the mice: no binding to PG could be detected using an ELISA as described above. No fusions were performed.

N-Terminal Monoclonal Antibodies Against Progastrin

As noted above, N-terminal monoclonal antibodies were generated against an antigen containing residues 1 to 14 of hPG linked to either bovine serum albumin (BSA) or keyhole limpet hemocyanin (KLH) by way of an Ahx-Cys linker on the C-terminal end of the 14 residue antigen (SWKPRSQQPDAPLG-Ahx-Cys (SEQ ID NO:26)).

In a first experiment, three mice were inoculated with a BSA-linked N-terminal peptide. From three fusions, performed with splenocytes from two of the three mice, one fusion yielded no clones that showed binding to PG or the immunogen. Of the two other fusions seeded in 96-well plates, one generated 4 PG-binding and PG-specific hybridomas, from which a single stable, IgG producing subclone was recovered. The second fusion also resulted in a single stable IgG1-producing, PG-binding and PG-specific hybridoma subclone. Overall, from three mice, 17 first round hybridomas, or 0.74% of the hybridomas screened) were positive for PG- and immunogen-binding, from which 9 positive cell lines were subcloned, of which two were positive, IgG-producing cell lines. Thus, the first experiment generated two clones after a couple of rounds of subcloning that retained a strong positive signal against the immunogen and hPG (positive for "PG-binding") and did not bind other gastrin gene-derived peptides (positive for "PG-specific"): hybridomas 43B9G11 and WE5H2G7, producing anti-hPG MAb1 and anti-hPG MAb 2□ respectively.

In a second experiment, mice were inoculated with a KLH-linked N-terminal peptide. Two fusions were performed with Sp2 myeloma cells. Of these, only one fusion generated PG- and immunogen-positive clones, that were also PG-specific. From this, 1920 hybridomas were seeded. Many hybridomas tested positive with the immunizing peptides but not progastrin, or were not PG-specific. Specifically, 297 hybridomas showed a strong positive signal for the immunizing peptide (around 15.5% of 1920), of which 124 were also positive for progastrin binding (6.5%). There were 36 hybridomas, or 1.8%, that were positive for progastrin but not the immunogen used. Only 12 hybridomas of the 1920 seeded yielded antibodies that specifically bind progastrin but not other gastrin gene products (0.6% of total hybridomas, 3.6% of clones that were positive for peptide and/or progastrin on first screening). Of the 12 selected clones, only 2 were stable enough to be established as permanent clones and frozen for long-term storage. Thus, in this second experiment, of the almost 2000 hybridomas were seeded, only 2 clones, 6B5B11C10 (producing anti-hPG MAb 3) and 20D2C3G2 (producing anti-hPG MAb4), producing anti-hPG MAb3 and MAb4 respectively, were recovered that express monoclonal antibodies capable of binding hPG and the immunizing peptide, and having specificity to progastrin over other gastrin gene products and high affinity to hPG. Both exemplary antibodies are of the IgG1 isotype.

In a third experiment, mice were inoculated with the same immunogen as in the second experiment. Fusions to Sp2 myeloma cells were performed with splenocytes from the two mice with the strongest immune response. Hybridomas were seeded from the fusions (3840 hybridomas from one fusion each, per mouse) and supernatants tested for PG- and immunogen-binding, as well as PG-specificity. From each fusion, 6 hybridomas showed PG-specificity, from which 3 subclones were selected that met the further selection for growth, monoclonality, antibody secretion, relative affinity. Thus, in all, 2.9% of the hybridomas tested after seeding (220/7680) were PG and immunogen-positive, of which 0.15% were positive clones (12/7680), the final subclones recovered constituting 0.15% of the original hybridomas seeded (6/7680). This experiment generated hybridomas 1E9A4A4 (producing anti-hPG MAb 15), 1E9D9B6 (producing anti-hPG MAb 16), 1C8D10F5 (producing anti-hPG MAb 17), 1A7C3F11 (producing anti-hPG MAb 18), 1B3B4F11 (producing anti-hPG MAb 19), and 1C11F5E8 (producing anti-hPG MAb 20).

The table below shows the number of clones seeded for each experiment, the immunogen used, and the number and percentage of hybridomas producing monoclonal antibodies that recognized both the immunogen and full length progastrin.

TABLE 3

| Expt | Immunogen | Clones seeded | $PG^+$ hybridoma supernatants | PG specific clones | PG specific, IgG producing subclones |
|---|---|---|---|---|---|
| 1 | (SEQ ID NO: 26)-Ahx-Cys-BSA | 2304 | 17 (0.74%) | 9 (0.39%) | 2 (0.087%) |
| 2 | (SEQ ID NO: 26)-Ahx-Cys-KLH | 1920 | 124 (6.5%) | 12 (0.6%) | 2 (0.1%) |
| 3 | (SEQ ID NO: 26)-Ahx-Cys-KLH | 7680 | 220 (2.9%) | 12 (0.15%) | 6 (0.1%) |

C-Terminal Monoclonal Antibodies Against Progastrin

C-terminal monoclonal antibodies were generated against an antigen containing residues 55 to 80 of hPG linked to either KLH or DT by way of an Cys-Ahx-Ahx linker on the N-terminal end of the 26 residue antigen (Cys-Ahx-Ahx-QGPWLEEEEEAYGWMDFGRRSAEDEN (SEQ ID NO:96)). Attempts to generate hybridomas with a smaller antigen containing only residues 70 to 80 of hPG, Cys-Ahx-Ahx-FGRRSAEDEN (SEQ ID NO:97), conjugated either to BSA or KLH, failed to generate any clones.

Three experiments were performed. In the first two experiments, in which the shorter peptide was used, zero subclones were recovered. Specifically, in a first experiment 4 mice were injected with a C-terminal peptide corresponding to SEQ ID NO:97, linked to BSA. None of the fusions generated any IgG-producing hybridomas. In a second experiment, 6 mice were injected, 3 each, with a peptide corresponding to SEQ ID NO:97, linked to KLH at its N-terminal end, or a peptide corresponding to SEQ ID NO:97, linked to KLH at its C-terminal end. For the first immunogen, fusions were performed and hybridomas recovered, but no subclones positive for PG-binding and PG-specificity were isolated. For the second immunogen, none of the mice developed an immune response and no fusions were performed.

In a third experiment, a 26 amino acid peptide including C-terminal sequences not unique to hPG was used. The immunogen, which included a peptide corresponding to SEQ ID NO:96 linked to either KLH or DT, was injected into mice. Fusions to Sp2 myeloma cells were performed with splenocytes from the two mice that had the strongest response. 3840 hybridomas were seeded from one fusion per mouse. Overall, from 7680 hybridomas screened, of which 382 (5%) were PG-positive and PG-specific, 13 (0.17%) stable, positive subclones were recovered: 1B4A11D11 (producing anti-hPG MAb 5), 1B6A11F2 (producing anti-hPG MAb 6), 1B11E4B11 (producing anti-hPG MAb 7), 1C10D3B9 (producing anti-hPG MAb 8), D8F5B3 (producing anti-hPG MAb 9), 1E1C7B4 (producing anti-hPG MAb 10), 2B4C8C8 (producing anti-hPG MAb 11), 2B11E6G4 (producing anti-hPG MAb 12), 2C6C3C7 (producing anti-hPG MAb 13), 2H9F4B7 (producing anti-hPG MAb 14), 1F11F5E10 (producing anti-hPG MAb 21), 1F11F5G9 (producing anti-hPG MAb 22), and 1A11F2C9 (producing anti-hPG MAb 23).

The table below shows the number of clones seeded for each experiment, the immunogen used, the number of hybridomas screened, the number and percentage of hybridomas producing PG- and immunogen-binding monoclonal antibodies, that are PG-specific and meeting the selection criteria (growth, monoclonality, relative affinity, etc.) after three rounds of subcloning.

TABLE 4

| Expt | Immunogen | Clones seeded | $PG^+$ hybridoma supernatants | PG Specific clones | PG specific, IgG-producing subclones |
|---|---|---|---|---|---|
| 1 | BSA-linker-(SEQ ID NO: 97) | 3072 | 10 (0.32%) | 9 (0.29%) | 0 |
| 2 | KLH-linker-(SEQ ID NO: 97) | 1920 | 27 (0.47%) | 4 (0.07%) | 0 |
| | (SEQ ID NO: 97)-linker-KLH | | 0 | 0 | 0 |
| 3 | KLH-linker-(SEQ ID NO: 96) | 3840 | 192 (5%) | 17 (0.44%) | 10 (0.26%) |
| | DT-linker-(SEQ ID NO: 96) | 3840 | 190 (4.95%) | 13 (0.34%) | 3 (0.08%) |

The monoclonal antibodies, and the stable hybridomas from which they are produced are detailed in the table below:

TABLE 5

| Monoclonal antibody | Hybridoma | Mouse Ig |
|---|---|---|
| MAb 1 | 43B9G11 | IgG1 |
| MAb 2 | WE5H2G7 | IgG1 |
| MAb 3 | 6B5B11C10 | IgG1 |
| MAb 4 | 20D2C3G2 | IgG1 |
| MAb 5 | 1B4A11D11 | IgG1 |
| MAb 6 | 1B6A11F2 | IgG1 |
| MAb 7 | 1B11E4B11 | IgG1 |
| MAb 8 | 1C10D3B9 | IgG1 |
| MAb 9 | 1D8F5B3 | IgG1 |
| MAb 10 | 1E1C7B4 | IgG1 |
| MAb 11 | 2B4C8C8 | IgG1 |
| MAb 12 | 2B11E6G4 | IgG1 |
| MAb 13 | 2C6C3C7 | IgG1 |
| MAb 14 | 2H9F4B7 | IgG1 |
| MAb 15 | 1E9A4A4 | IgG1 |
| MAb 16 | 1E9D9B6 | IgG1 |
| MAb 17 | 1C8D10F5 | N.D. |
| MAb 18 | 1A7C3F11 | IgG2 |
| MAb 19 | 1B3B4F11 | IgG2 |
| MAb 20 | 1C11F5E8 | IgG2 |
| MAb 21 | 1F11F5E10 | IgG2 |
| MAb 22 | 1F11F5G9 | IgG2 |
| MAb 23 | 1A11F2C9 | IgG2 |

Hybridoma cell lines 1B4A11D11 (MAb 5, registration no. CNCM I-4371), 1B6A11F2 (MAb 6, registration no. CNCM I-4372), 1B11E4B11 (MAb 7, registration no. CNCM I-4373), 2B4C8C8 (MAb 11, registration no. CNCM I-4374), 2B11E6G4 (MAb 12, registration no. CNCM I-4375), and 1E9A4A4 (MAb 15, registration no. and CNCM I-4376) were deposited in accordance with the Treaty of Budapest and received on Oct. 6, 2010 by the Collection Nationale de Cultures de Microorganisms (CNCM), Institut Pasteur, Paris, France.

Cloning and Sequencing of Anti-hPG Monoclonal Antibodies

Monoclonal antibodies produced by hybridomas can be cloned and sequenced using techniques known to those skilled in the art. Monoclonal antibodies from hybridomas listed in Table 5 above were sequenced as described below.

Sequences encoding monoclonal antibodies produced by hybridomas 6B5B11C10 and 20D2C3G2 were cloned and sequenced using standard techniques. Briefly, total RNA was isolated from frozen cell pellets using RNABee reagent, AMSBio catalogue no. CS-104B, used according to manufacturer's instructions. cDNA for V-regions was prepared from mRNA using reverse-transcriptase polymerase chain reaction (RT-PCR), followed by 5' rapid amplification of cDNA ends (RACE). cDNA synthesis was carried out using constant-region-specific primers, after which the first strand product was purified and terminal deoxynucleotide transferase was used to add homopolymeric tails to the 3' ends of the cDNA. The "tailed" cDNA sequences were then amplified by PCR using primer pairs, one primer each for the homopolymeric tail and either the $V_H$ or $V_L$ region, respectively. Heavy and light chain variable region PCR products were then cloned into a "TA" cloning vector (p-GEM®-T easy, Promega cat. no A 1360) and sequenced using standard procedures. See FIGS. 2A-2B (MAb 3), FIGS. 2C-2D (MAb 4).

Sequences encoding monoclonal antibodies produced by hybridomas 1C10D3B9, 2C6C3C7, 1B3B4F1, and 1E9D9B61 were determined as follows. Total RNA was isolated from frozen cell pellets using RNAqueous®-4PCR kit (Ambion cat. No. AM1914) used according to manufacturer's instructions. Heavy chain V-region mRNA was amplified using a set of six degenerate primer pools (HA to HF) and light chain V-region mRNA was amplified using a set of eight degenerate primer pools, seven for the κ cluster (KA to KG) and one for the λ cluster (LA). cDNA for variable regions was prepared from mRNA using RT-PCR. cDNA synthesis was carried out using constant-region-specific primers, followed by PCR using pools of degenerate primers for 5' murine signal sequences and primers to 3' constant regions for each of IgGVH, IgκVL and IgλVL. (Jones et al., 1991, *Rapid PCR cloning of full-length mouse immunoglobulin variable regions*, Bio/Technology 9:88-89). Heavy and light chain variable region PCR products were then cloned into a "TA" cloning vector (p-GEM®$^T$ easy, Promega cat. no A 1360) and sequenced using standard procedures. See FIGS. 2E-2F (MAb 8), FIGS. 2G-2H (MAb 13), FIGS. 2I-2J (Mab 16), and FIGS. 2K-2L (Mab 19).

Example 2: Binding Affinity of Anti-hPG Antibodies

A. Relative Affinity

Relative affinity of exemplary monoclonal antibodies was measured using the ELISA method described above, in which wells were coated with a peptide solution containing 50 ng progastrin and then incubated in the presence of increasing concentrations of each monoclonal antibody as follows:

| Monoclonal antibody | Concentration range tested |
|---|---|
| N-terminal anti-hPG monoclonal antibodies MAbs 1-4 | 0.001-1 μg/mL |
| N-terminal anti-hPG monoclonal antibodies MAbs 3, 15-20 | 0.1-100 ng/mL |
| C-terminal anti-hPG monoclonal antibodies MAbs 5-14, 21-23 | 0.03-30 ng/mL |

FIG. 3A shows the relative affinity of four anti-hPG monoclonal antibodies, MAbs 1-4 tested at concentrations of 1 ng/mL to 1 μg/mL. FIG. 3B shows the relative affinity of N-terminal anti-hPG monoclonal antibodies MAbs 3 and 15-20 tested at antibody concentrations of 0.1-100 ng/mL. FIG. 3C shows the relative affinity of C-terminal anti-hPG monoclonal antibodies MAbs 5-14 and 21-23 tested at antibody concentrations of 0.03-30 ng/mL.

B. Affinity Constant Measurements

To provide a more absolute quantification of affinity for the monoclonal antibodies, affinity constants were measured using the Proteon Technique (BioRad), according to Nahshol et al., 2008, Analytical Biochemistry 383:52-60, hereby incorporated by reference in its entirety. Briefly, an anti-mouse IgG antibody (50 μg/ml) was first coated on a sensor chip, making sure that the signal detected by the chip after injection of the antibody falls between 10,000 and 11,500 RU (response units). The murine monoclonal antibody to be tested was then injected (typical concentrations: 30 μg/ml). Sufficient binding of the antibody to be tested was determined based on a further signal of at least 500 RU on the sensor chip. A time-course of interaction between monoclonal anti-progastrin antibodies and progastrin was then measured by injecting varying concentrations of progastrin, for example 200, 100, 50, 25, and 12.5 nM, and the level of association detected. Typically, several channels are available to test multiple antibodies in parallel in a single experiment, making it possible to assay binding of test antibodies at varying concentrations of PG in parallel. Typically, one channel is reserved for a murine monoclonal antibody that is not specific to PG, as a control for non-specific binding, and another channel is injected with dilution buffer alone as a baseline for the background signal. Generally, no binding is detectable in the channels injected with non-specific murine antibody. Antibodies displaying a high level of association in this setting, which may result in saturation of the trapped monoclonal antibody by progastrin, can be tested against lower progastrin concentrations (50, 25, 12.5, 6.25 and 3.125 nM), allowing for a more refined measurement.

Affinity constants (KD) were calculated as the ratio between the dissociation constant (kd) and the association constant (ka). Experimental values were validated by analyzing the statistically relevant similarity between experimental curves based on binding measurements and theoretical profiles. The mathematical model used in the Proteon experiments to select whether experimental curves fit with the theoretical model was the Langmuir model, based on a 1:1 interaction between progastrin molecules and anti-progastrin monoclonal antibodies.

TABLE 6

| Monoclonal Antibody | Affinity constant measured KD (M) |
|---|---|
| Anti-hPG MAb 1 | 2.5 μM ($2.5 \times 10^{-6}$ M) |
| Anti-hPG MAb 2 | 185 nM ($1.85 \times 10^{-7}$ M) |
| Anti-hPG MAb 3 | 6.4 nM ($6.4 \times 10^{-9}$ M) |
| Anti-hPG MAb 4 | 3.5 nM ($3.5 \times 10^{-9}$ M) |
| Anti-hPG MAb 5 | 13 pM ($1.30 \times 10^{-11}$ M) |
| Anti-hPG MAb 6 | 0.6 nM ($6.38 \times 10^{-10}$ M) |
| Anti-hPG MAb 7 | 58 pM ($5.84 \times 10^{-11}$ M) |
| Anti-hPG MAb 8 | 0.1 nM ($1.08 \times 10^{-10}$ M) |
| Anti-hPG MAb 10 | 3.6 nM ($3.62 \times 10^{-9}$ M) |
| Anti-hPG MAb 11 | 0.3 nM ($3.12 \times 10^{-10}$ M) |
| Anti-hPG MAb 12 | 0.4 nM ($4.43 \times 10^{-10}$ M) |
| Anti-hPG MAb 13 | 0.6 nM ($6.12 \times 10^{-10}$ M) |
| Anti-hPG MAb 14 | 6.8 pM ($6.86 \times 10^{-12}$ M) |
| Anti-hPG MAb 15 | 0.2 nM ($2.11 \times 10^{-10}$ M) |
| Anti-hPG MAb 16 | 0.2 nM ($2.78 \times 10^{-10}$ M) |
| Anti-hPG MAb 17 | 8.3 nM ($8.29 \times 10^{-9}$ M) |
| Anti-hPG MAb 18 | 1.2 nM ($1.24 \times 10^{-9}$ M) |
| Anti-hPG MAb 19 | 0.7 nM ($7.79 \times 10^{-10}$ M) |
| Anti-hPG MAb 20 | 0.2 nM ($2.47 \times 10^{-10}$ M) |
| Anti-hPG MAb 21 | 3.9 nM ($3.90 \times 10^{-9}$ M) |
| Anti-hPG MAb 22 | 5 nM ($4.94 \times 10^{-9}$ M) |
| Anti-hPG MAb 23 | 0.4 μM ($3.99 \times 10^{-7}$ M) |

Example 3: Aggregation of Anti-hPG Antibodies

Aggregation of antibodies can reduce therapeutic efficacy by reducing the amount of antibody available to bind the target protein. Antibodies with very low levels of aggregation are preferable for therapeutic applications. Each batch of antibody will vary compared to other batches of the same monoclonal antibody. It is generally desirable to use batches with low aggregation. To quantify antibody aggregation, antibody solutions were placed in a spectrofluorimeter (Photon Technology International), and irradiated at 280 nm. Diffusion was measured at 280 nm, while emission due to aromatic amino acids (mostly tryptophans) was measured at 330 nm. The level of aggregation was then quantified by calculating the ratio between OD measurement values at 280 nm versus 330 nm, as described in Nominé et al., 2003, Biochemistry 42: 4909-4917. A higher 280/330 nm ratio indicates a higher amount of aggregation. The concentration of antibody used was 15 μg/ml, 5 to 15 times above that used for in vitro treatments.

Results are shown in Table 7 below and FIG. 4.

TABLE 7

| Sample | 280/330 nm Ratio |
|---|---|
| Bovine Serum Albumin (n = 1) | 6.4 |
| Anti-hPG MAb 1 (n = 1) | 15.42 |
| Anti-hPG MAb 2 (n = 2) | 9.81 |
| Anti-hPG MAb 3 (n = 2) | 3.08 |
| Anti-hPG MAb 4 (n = 2) | 1.94 |

Example 4: Binding Specificity of Anti-hPG Monoclonal Antibodies

PG is only one of the peptide products of the gastrin gene. Other gastrin gene products have roles in normal homeostasis, but it is PG's role in CRC that makes it a useful target for therapeutic and diagnostic purposes. The monoclonal antibodies described herein are specific to full length progastrin over all other peptides resulting from the expression and processing of the gastrin gene, such as glycine-extended (G17-gly), amidated (Gastrin17) gastrins, and the C-terminal flanking peptide (CTFP). These peptides are present in the circulation. Binding specificity of anti-hPG monoclonal antibodies was determined by assaying the antibodies against human progastrin and other gastrin gene-derived peptides, using the ELISA assay described above in Example 1.

Specifically, wells coated with a solution containing one of the following peptides at the indicated amounts: progastrin, Keyhole Limpet hemocyanin (KLH), amidated gastrin-17 (G17), glycine-extended gastrin 17 (Ggly), or C-terminal Flanking Peptide (CTFP):

| Screening peptides | Test quantity |
|---|---|
| Recombinant Progastrin | 50 ng (expt 1)<br>25 ng (expt 2) |
| Human amidated gastrin I (G-17) | 50 and 250 ng |
| Glycine-extended gastrin 17 (G17-Gly) | 50 and 250 ng |
| KLH | 50 and 250 ng |
| C-terminal flanking peptide (CTFP) | 50 and 250 ng |

In a first experiment, 3 ng/ml (0.3 ng) of anti-hPG MAb 3 and 1 μg/ml (0.1 μg) each of anti-hPG MAbs 1, 2, and 4 were used. See FIG. 5A. In a second experiment, the binding specificity of anti-hPG MAbs 5 to 14 and 21-23 were tested at 0.3 ng/mL, see FIG. 5B, and the binding specificity of anti-hPG MAbs 3, 15-20 were tested at 1 ng/mL, see FIG. 5C.

Antibodies displayed a weak reaction to high quantities of KLH which was coupled to the antigenic peptide used in some of the immunogens to immunize the mice in Example 1 above. There was no detectable effect of BSA on PG binding of any antibodies, including those raised against immunogens that included BSA as a carrier.

All antibodies displayed high specificity for binding to full length hPG (tested at 50 and then 25 ng) as compared to other gastrin-gene derived peptides, such as amidated gastrin-17, glycine extended gastrin 17, and the C-terminal flanking peptide, a 5 amino acid peptide that is cleaved from progastrin during the normal processing of the polypeptide to form gastrin. The exemplary antibodies showed no detectable binding (signal above "PBS alone" background) to any the gastrin-gene derived peptides other than hPG.

Example 5: Competition Assay

The ability of an anti-hPG monoclonal antibody to compete with an anti-hPG polyclonal antibody for binding to progastrin was determined using an ELISA with a "capture" anti-hPG antibody and a "detection" anti-hPG antibody. Anti-hPG MAb 3 was assayed as follows: 96-well plates were pre-coated with C-terminal progastrin polyclonal antibodies raised against a peptide consisting of residues 71 to 80 of hPG. The plates were then incubated with 100 pM progastrin was incubated, followed by addition of 10 μg/ml biotinylated N-terminal anti-hPG polyclonal antibody, raised against a peptide consisting of the amino acid sequence of SEQ ID NO:25, and increasing concentrations of anti-hPG MAb 3 monoclonal antibody. Binding of the biotinylated N-terminal anti-hPG polyclonal antibody was detected by incubating the plates with streptavidin-HRP followed by OPD, according to standard protocols. Binding was measured by quantifying luminescence.

Results show that increasing concentrations (μg/ml) of Anti-hPG MAb 3 decrease the ability of polyclonal anti-hPG antibodies to bind to progastrin, showing that the monoclonal antibody competes with the polyclonal antibody. See, FIG. 6.

Example 6: Epitope Mapping

The specific epitopes bound by exemplary monoclonal antibodies were mapped using the SPOT® technique and alanine scanning, as described in Laune, D., et al., 2002, *J. Immunol. Methods* 267:53-70 and Laune, D., 1997, *J. Biol. Chem.* 272:30937-30944, respectively. In the SPOT® technique, 15 amino acid peptide sequences spanning a putative epitope are generated and spotted onto a nitrocellulose membrane which is then probed with the test antibody to determine the minimal epitope sequence recognized by the antibody. Alanine scanning is used to determine residues within an epitope that are critical for antibody binding: each residue within a putative epitope is mutated one by one to an alanine, and the alanine-containing peptides are then probed with the test antibody.

Families of epitope were identified for exemplary antibodies of the present disclosure. For N-terminal anti-hPG monoclonal antibodies MAbs 1-4 and 15-20, epitopes comprise at least the following sequences: DAPLG (SEQ ID NO:28), PDAPLG (SEQ ID NO:29), PRSQQPD (SEQ ID NO:30), WKPRSQQPD (SEQ ID NO:31), or WKPRSQQPDAPLG (SEQ ID NO:32), as shown in Table 8 below.

TABLE 8

| MAb | PG peptide antigen:<br>SWKPRSQQPDAPLG | SEQ ID NO |
|---|---|---|
| MAb 2 | WKPRSQQPDAPLG | 32 |
| MAb 4 | WKPRSQQPDAPLG | 32 |
| MAb 1 | PDAPLG | 29 |
| MAb 3 | DAPLG | 28 |
| MAb 17 | WKPRSQQPD | 31 |
| MAb 18 | WKPRSQQPD | 31 |
| MAb 19 | WKPRSQQPD | 31 |
| MAb 20 | WKPRSQQPD | 31 |
| MAb 15 | PRSQQPD | 30 |
| MAb 16 | PRSQQPD | 30 |

For C-terminal anti-hPG monoclonal antibodies MAbs 5-7, 9-12, 14 and 21-23, epitopes comprise at least the following sequences: FGRR (SEQ ID NO:33), MDFGR (SEQ ID NO:34), AEDEN (SEQ ID NO:35), and GWMDFGRR (SEQ ID NO:36), as shown in Table 9 below.

TABLE 9

| MAb | PG peptide antigen:<br>QGPWLEEEEEAYGWMDFGRRSAEDEN | SEQ ID NO |
|---|---|---|
| MAb 14 | GWMDFGRR | 36 |
| MAb 11 | MDFGR | 34 |
| MAb 5 | FGRR | 33 |
| MAb 6 | FGRR | 33 |

TABLE 9-continued

| MAb | PG peptide antigen: QGPWLEEEEEAYGWMDFGRRSAEDEN | SEQ ID NO |
|---|---|---|
| MAb 7 | FGRR | 33 |
| MAb 9 | FGRR | 33 |
| MAb 10 | FGRR..E | 33 |
| MAb 12 | FGRR | 33 |
| MAb 23 | AEDEN | 35 |

Example 7: Neutralizing Activity of Anti-hPG Antibodies on Cancer Cell Lines (A) Neutralizing Activity of Anti-hPG Monoclonal Antibodies Anti-hPG monoclonal antibodies decrease cell survival in representative colorectal cancer cell lines. Suitable colorectal cancer cell lines are known in the art. For example, HCT116, LS174T, SW480, and SW620 are cell lines commonly used to study colon cancer, which produce and secrete progastrin. Monoclonal antibodies to PG were tested for their ability to inhibit proliferation in these different cell lines. Survival of cells from each HCT116, LST174T, SW480, and SW620 was tested using different anti-hPG monoclonal antibodies.

For each experiment, 50,000 cells were seeded into 6-well plates in medium containing fetal calf serum and incubated for 8 hours. Cells were serum-starved overnight, and starting at 24 hours after seeding (time "T0"), cells were treated in duplicates every 12 h for 48 hours, in the absence of fetal calf serum, with 1 μg/ml of monoclonal control antibodies (mouse anti-human IgG1, Calbiochem®, Ref #411451)(CT mAb), or with 1 μg/ml anti-hPG MAb 1-4 as indicated. Upon further quantitation of monoclonal antibodies, antibodies were determined to have been used at approximately 3 to 5 μg/ml. The number of cells at T0 was counted in a control well, for each experiment. For HCT116 cells, experiments were conducted in the presence of 0.5% fetal calf serum. 48 h after the start of the treatment, the number of surviving cells in each well was counted three times in a blinded experiment. Reduction in CRC cell proliferation or survival was determined by calculating surviving anti-hPG MAB-treated cells as a percentage of control MAb-treated cells. Cell counts at the start of treatment (T0) were subtracted from test and control cell counts measured at 48 hours. Specifically, the number of live cells in both control and anti-hPG MAb treated wells was counted at 48 hours, then the difference between each cell count and the cell count determined at T0, was calculated. The resulting number of anti-hPG MAB-treated cells was then expressed as a percentage of the number of control MAb-treated cells.

FIGS. 7A-7C show the effect of anti-hPG MAb 3 and anti-hPG MAb 4 on the survival of SW480 cells, LS174T cells, and HCT116 cells from representative experiments. Results are mean+/−S.E. from 4 wells coming from two independent experiments. Treatment with anti-hPG monoclonal antibodies significantly reduced cell number as compared to treatment with control antibody. Statistical significance was determined using a Student's T-test: *=$p<0.05$, =$p<0.01$, and *=$p<0.001$. In each cell line, anti-hPG antibodies reduced cell survival. In one cell line, LST174T, cell numbers at the end of 48 hours of treatment with anti-hPG antibodies were lower than the cell numbers at the start of the experiment, suggesting that the antibodies caused cells to die, in addition to inhibiting cell proliferation.

Table 10 shows the percent surviving SW480 colorectal cancer cells treated with each of four monoclonal anti-hPG antibodies as compared to a control monoclonal antibody (mouse anti-human IgG1, Calbiochem®, Ref #411451)(CT mAb).

TABLE 10

| SW480 (T0 = 26 667) | Cell numbers - T0 | % of control | p (Treated vs Control) Mann Whitney, two-tailed |
|---|---|---|---|
| Control mAb | 36050 +/− 3228 | | |
| Anti-hPG MAb 1 | 30425 +/− 3098 | 84.4 | 0.3556 |
| Anti-hPG MAb 2 | 28925 +/− 2757 | 80.2 | 0.0476 |
| Anti-hPG MAb 3 | 6050 +/− 1788 | 16.8 | <0.0001 |
| Anti-hPG MAb 4 | 17560 +/− 3439 | 48.7 | 0.0002 |

As compared to control, treatment with anti-hPG monoclonal antibodies reduced survival of cancer cells by 83.2% (Anti-hPG MAb 3), 51.3% (Anti-hPG MAb 4), 19.8% (Anti-hPG MAb 2), and 15.6% (Anti-hPG MAb 1).

The tables below show the percent surviving LS174T and HCT-116 cells treated with anti-hPG MAb 3 and 4 as compared to the control monoclonal antibody. The data are represented graphically in the corresponding panels of FIGS. 7A-7I.

TABLE 11

| HCT-116 (T0 = 42 750) | Cell numbers -T0 | % of control | P (Treated vs Control) Mann Whitney, Two-tailed |
|---|---|---|---|
| Control MAb | 151 250 +/− 9071 | | |
| MAb3 | 62 750 +/− 9194 | 41.5% | <0.0001 |
| MAb4 | 82 250 +/− 7435 | 54.4% | <0.0001 |

TABLE 12

| LS 174T (T0 = 51 666) | Cell numbers - T0 | % of control | P (Treated vs Control) Mann Whitney, Two-tailed |
|---|---|---|---|
| Control MAb | 85 334 +/− 7520 | | |
| MAb3 | −6666 +/− 5000 | −8% | 0.0084 |
| MAb4 | +8334 +/− 2500 | 7% | 0.0085 |

Under in vitro assay conditions, complete inhibition of cell growth is not expected. In cell culture, progastrin is continually secreted by cancer cells and accumulates in the cell culture medium. Progastrin levels are expected to increase over time more so than would occur in circulation in the body, increasing the ratio of target protein to antibody and diluting the neutralizing effect of the antibodies. Thus, the neutralizing effect observed with the antibodies in vitro is expected to be stronger in vivo, where progastrin secreted by tumor cells is carried away in the blood stream, lessening its accumulation in situ.

Inhibition of cell proliferation by anti-hPG MAbs 5 to 23 was determined in one or more of CRC cell lines SW620, HCT116, and LS47T. Assays were performed in 6-well plates as described above using 5 μg/ml control or test (anti-hPG) monoclonal antibodies. 50,000 cells were seeded per well for HCT116 and LS174T, and 100,000 for SW620 cells. The tables below provide percent of surviving treated cells relative the control treatment from representative experiments. Average results are graphed in FIGS. 7G-7I for cell lines SW620, LS174T, and HCT-116 respectively.

TABLE 13

| | Cell numbers -T0 | % of control | P (Treated vs Control) Mann Whitney, Two-tailed |
|---|---|---|---|
| Experiment 1 SW 620 (T0 = 103 067) | | | |
| Control MAb | 82 100 +/- 15489 | — | |
| MAb 5 | 54 511 +/- 8292 | 66% | <0.0001 |
| MAb 6 | 44367 +/- 9321 | 54% | <0.0001 |
| MAb 7 | 49279 +/- 8009 | 60% | <0.0001 |
| MAb 8 | 32673 +/- 4680 | 40% | <0.0001 |
| MAb 9 | 73283 +/- 3835 | 89% | 0.1305 |
| MAb 10 | 70178 +/- 4173 | 85% | 0.0618 |
| Experiment 2 SW 620 (T0 = 118 553) | | | |
| Control MAb | 81 347 +/- 6062 | | |
| MAb 11 | 46 974 +/- 7422 | 58% | 0.0003 |
| MAb 12 | 52 980 +/- 10529 | 65% | 0.0002 |
| MAb 13 | 38 933 +/- 5284 | 48% | 0.0003 |
| MAb 14 | 83 767 +/- 9484 | 103% | 0.21 |
| MAb 21 | 59 497 +/- 2828 | 73% | 0.0002 |
| MAb 22 | 64 227 +/- 7123 | 79% | 0.0013 |
| MAb 23 | 83 914 +/- 5629 | 103% | 0.82 |
| Experiment 3 SW 620 (T0 = 116 283) | | | |
| Control MAb | 101 333 +/- 17 626 | — | |
| MAb 15 | 66 052 +/- 7739 | 65% | <0.0001 |
| MAb 16 | 58 883 +/- 9950 | 58% | <0.0001 |
| MAb 17 | 76 688 +/- 5578 | 75.5% | 0.0014 |
| MAb 18 | 75 874 +/- 10129 | 75% | 0.0005 |
| MAb 19 | 70 242 +/- 10 851 | 69% | <0.0001 |
| MAb 20 | 66 470 +/- 7557 | 66% | <0.0001 |

TABLE 14

| | Cell numbers -T0 | % of control | P (Treated vs Control) Mann Whitney, Two-tailed |
|---|---|---|---|
| Experiment 1 LS 174T (T0 = 60 944) | | | |
| Control MAb | 107 956 +/- 5859 | | |
| MAb 13 | 62 341 +/- 10 683 | 58% | 0.0003 |
| MAb 16 | 65 389 +/- 8185 | 61% | 0.0002 |
| Experiment 2 LS 174T (T0 = 86 389) | | | |
| Control Mab | 241 711 +/- 11 620 | | |
| MAb 14 | 246 444 +/- 19563 | 102% | ns |
| MAb 19 | 204 433 +/- 8946 | 84.5% | 0.0005 |
| Experiment 3 LS 174T (T0 = 79 667) | | | |
| Control MAb | 135 800 +/- 18 338 | | |
| MAb 8 | 57 333 +/- 12657 | 42% | <0.001 |

TABLE 15

| | Cell numbers -T0 | % of control | P (Treated vs Control) Mann Whitney, Two-tailed |
|---|---|---|---|
| Experiment 1 HCT-116 (T0 = 49 286) | | | |
| Control MAb | 78 214 +/- 6230 | | |
| MAb 13 | 28 805 +/- 3477 | 36% | <0.0001 |
| MAb 16 | 56 484 +/- 8333 | 72% | <0.0001 |
| MAb 19 | 68 945 +/- 8795 | 88% | 0.0302 |
| Experiment 2 HCT-116 (T0 = 60 944) | | | |
| Control MAb | 122 456 +/- 1697 | | |
| MAb 8 | 75 867 +/- 15627 | 62% | <0.0001 |
| MAb 16 | 87011 +/- 5091 | 71% | <0.0001 |

(B) Neutralizing Activity of Anti-hPG Polyclonal Antibodies

Assays were conducted as described above, with the following modifications. An N-terminal anti-hPG polyclonal antibody as described in Example 5 was used. As a control, 3 μg/ml of polyclonal (Polyclonal Rabbit anti-human IgG, Affinity BioReagents, Ref #SA1-600)(CT pAB) was used. For anti-PG treatments, 3 μg/ml anti-hPG polyclonal antibodies were used for all cell lines. SW480 and LS174T were treated with control or N-terminal anti-hPG polyclonal antibodies for 24 to 48 h in DMEM without FCS, while HCT116 were treated with anti-hPG polyclonal antibodies for 48 h in DMEM with 0.5% FCS. Surviving cells were then trypsinized and counted, in comparison with cells treated with an equivalent concentration of control (anti human IgG) polyclonal antibody.

Results of representative experiments are shown in the tables below and FIGS. 7D-7F. Treatment with anti-hPG polyclonal antibodies significantly reduced cell number as compared to treatment with control antibody. Statistical significance was determined using a Student's T-test: *=$p<0.05$, =$p<0.01$, and *=$p<0.001$. Cell numbers are expressed relative to the number of cells in culture at the start of the experiment (T0). For each experiment, the cells in each of 4 wells were counted three times. As with anti-hPG monoclonal antibodies, colorectal cancer cell proliferation is inhibited by anti-hPG polyclonal antibodies, demonstrating that anti-tumor effects seen with polyclonal antibodies to progastrin are reasonably predictive of monoclonal antibody activity in blocking progastrin's effect on cancer cells.

TABLE 16

| | Cell numbers -T0 | % of control | P (Treated vs Control) Mann Whitney, Two-tailed |
|---|---|---|---|
| Experiment 1 SW 480 (T0 = 26 667) | | | |
| Control PAb | 37 580 +/- 4233 | | |
| PG PAb | 7833 +/- 3660 | 21% | 0.0001 |

TABLE 16-continued

| | Cell numbers -T0 | % of control | P (Treated vs Control) Mann Whitney, Two-tailed |
|---|---|---|---|
| Experiment 2 HCT-116 (T0 = 58 750) | | | |
| Control PAb | 105 350 +/− 8660 | | |
| PG PAb | 7833 +/− 3660 | 21% | <0.05 |
| Experiment 3 LS174T (T0 = 112 500) | | | |
| Control PAb | 207 500 +/− 10 000 | | |
| PG PAb | 102 500 +/− 5000 | 49.5% | <0.01 |

Example 8: Neutralizing Effect of Anti-hPG Monoclonal Antibodies is Eliminated when Antibodies are Pre-Incubated with Purified hPG To demonstrate that the neutralizing effect of anti-hPG monoclonal antibodies is mediated by binding to hPG, LS174T cells were cultured in the presence of an exemplary antibody—anti-hPG MAb 8—that had been pre-incubated with and without hPG. As positive and negative controls, cells were cultured with hPG alone, a control antibody alone, and the control antibody pre-incubated with hPG.

Specifically, 33.3 nM (5 μg/mL) anti-hPG MAb 8 was pre-incubated for 1 hour at room temperature with 20-fold molar excess recombinant hPG, or 667 nM (6.67 μg/mL). Recombinant human progastrin, prepared as described in Example 1, was used. In parallel, 33.3 nM (5 μg/mL) of murine anti-human IgG1 (General BioScience, reference no. AB23420) was similarly pre-incubated with and without hPG.

5000 LS174T cells were seeded into each well in 96-well plates in medium containing 10% Fetal Calf Serum and incubated for 8 hours, after which the cells were switched to serum-free medium and grown for another 12 hours. After growth in serum-free medium for 12 hours, cells were treated with one of the following every twelve hours: control antibody, control antibody pre-incubated with hPG, anti-hPG MAb 8 alone, anti-hPG MAb 8 pre-incubated with hPG, and hPG alone. 48 hours after the first treatment, remaining viable cells were quantified by incubating plates with Promega CellTiter 96® Aqueous One Solution and recording the absorbance at 490 nM. The absorbance measured for cells treated with the control monoclonal antibody ("control MAb") was set to 100%, and all other experimental conditions measured against the absorbance of cells treated with control MAb. Results are shown in the Table below and FIG. 8.

TABLE 17

| | Absorbance | % of control | p (Treated vs Control) Mann Whitney, two-tailed |
|---|---|---|---|
| PG treatment alone | 0.244 +/− 0.088 | 132.5% | 0.099 (n.s.) |
| Control MAb | 0.184 +/− 0.084 | 100% | N.A. |
| Anti-hPG MAb 8 | 0.057 +/− 0.06 | 31% | 0.001 |
| Control MAb + hPG | 0.321 +/− 0.079 | 174.5% | 0.002 |
| Anti-hPG MAb8 + hPG | 0.271 +/− 0.076 | 147.6% | 0.0229 |

Addition of, or incubation of antibodies with, hPG increases the number of live cells in culture. In contrast, treatment of the cells with anti-hPG MAb 8 alone causes a significant reduction in the number of viable cells. Thus, the ability of anti-hPG monoclonal antibodies to neutralize PG activity is abolished by the addition of hPG, which is thought to bind to and saturate the antibody. This result confirms the specificity of the neutralizing activity of anti-hPG monoclonal antibodies.

Example 9: In Vivo Anti-Tumor Activity of Anti-hPG Antibodies

A number of experimental in vivo models have been developed for the study of colorectal cancer. Mouse xenograft studies, in which tumor tissue or cells from human cancer cell lines are transplanted into an immunodeficient (so-called "nude") mouse, have been developed. Pocard M., et al., In vivo (1996) 10(5): 463-469. Several transgenic mouse models have also been developed. Murine models include heterozygous mutations in the adenomatous polyposis coli (APC) gene, such as $Apc^{Min}$, Apc1638N, Apc716, or ApcΔ14. The APC tumor suppressor gene encodes a cytosolic protein, APC, which, when intact, binds to and sequesters β-catenin in the cytosol within a multi-protein complex targeting β-catenin to the proteasome for degradation, thereby preventing β-catenin from activating the transcription factor Tcf-4 in the nucleus. Heyer et al., Oncogene 18:5325-5333 (1999). APCΔ14 mice carry a heterozygous deletion of exon 14 within the adenomateous polyposis coli (APC) gene. Similar to what occurs in more than 70% of patients with sporadic colorectal cancer, somatic loss of heterozygocity (LOH) in the second Apc allele occurs in intestinal cells, leading to a constitutive activation of the β-catenin/Tcf-4 transcriptional complex, and to the spontaneous development of intestinal tumors in these animals. The molecular origin of these adenomas and carcinomas, as well as tumor morphology (including vascularization, inflammatory response and presence of immune cells) with much greater similarity to that of human tumors compared with mouse xenograft models, make APCΔ14 a highly relevant model for human colorectal cancer therapy studies. Colnot et al., 2004, Lab. Invest. 84:1619-1630. Other transgenic mouse models are based on mutations in genes such as MSH2, MSH6, CDX2, K-RAS, as well as lines combining mutations in APC with mutations in other oncogenes. Heyer et al., 1999, Oncogene 18:5325-5333, Janssen K P et al., 2002, Gastroenterology 123: 492-504. These models are widely used to study colorectal cancer and test hypotheses regarding the treatment of colorectal cancer.

Transgenic mice carrying a heterozygous deletion of exon 14 with the adenomatous polyposis coli gene (APCΔ14) serve as a model for colorectal cancer, developing tumors similar to those found in human colon cancers. In a first experiment, APCΔ14 mice were treated with a preparation containing equal amounts of anti-hPG polyclonal antibodies raised against (1) a peptide corresponding to SEQ ID NO:25 and (2) a C-terminal peptide as described in Hollande et al., WO 07/135542. 3.5 month old mice were treated for 5 weeks with either control polyclonal antibody or anti-hPG polyclonal antibody (two mice per treatment). Antibodies were administered by intra-peritoneal injection twice a week at a dose of 10 mg/kg (150 μl injection volume). At the end of the treatment, mice were sacrificed and the intestines were washed with PBS, dissected for digital imaging and fixed in 4% para-formaldehyde for immuno-histochemical analysis. Tumor number and images of colorectal tissue were recorded.

Morphological assessment of intestinal tissue showed that anti-hPG antibodies did not affect the renewal of healthy murine intestinal epithelium. Tumors were counted in the treatment and control groups. The total number of tumors for the mice treated with control antibodies was 27, as compared to 4 in the mice treated with anti-hPG antibodies. Thus, anti-hPG antibodies reduce tumor count by more than 6.5 fold as compared to control antibodies while not affected the renewal of healthy epithelium in the mouse intestine.

In a second experiment, effect of anti-hPG antibodies in APCΔ14 mice and normal (control) mice (C57BL6J) was examined. 4-month old mice were treated twice a week for 6 weeks with either control polyclonal antibody—a rabbit anti-human IgG antiserum (Jackson ImmunoResearch (reference no. 309-005-0089)—or anti-hPG polyclonal antibody, by intra-peritoneal injection twice a week at a dose of 9 mg/kg (150 μl injection volume). After six weeks of treatment, two hours before sacrifice, mice were injected with Bromo-deoxy-uridine (BrdU) (2 mg per mouse, intraperitoneal injection). 6 APCΔ14 mice were treated with anti-hPG polyclonal and 4 with control polyclonal antibodies. Control and anti-hPG antibodies were administered to 6 normal (C57BL6J) mice each. No intestinal abnormalities were detected in any of the mice from either group, further demonstrating the safety and lack of adverse effect of anti-hPG antibodies on normal intestinal tissue.

Tumor numbers and size (height and length) was examined in treated versus control groups of APCΔ14 mice. Tumor size was determined by measurements of images taken from intestines of each animal, prepared as follows. Intestines were rinsed as described above, dissected longitudinally, embedded in paraffin, and processed for immunohistochemistry using the "Swiss roll" technique. Measurements of tumor length and height were performed using Image J software.

Results are shown in Table 18 and FIGS. 9A and 9B. Results for tumor size show a statistically significant difference between control-treated and anti-hPG-treated groups. Statistical significance was determined using a Mann Whitney test: *=p<0.05, =p<0.01, and *=p<0.001. Mice treated with control antibody exhibited a total of 125 tumors, with 31.25 tumors on average per mouse. Anti-hPG treated mice exhibited 46 tumors or an average of 7.6 tumors per mouse. This difference is statistically significant (Mann-Whitney test, P=0.0095) showing that anti-hPG antibodies significantly reduces the number of colorectal cancer tumors in vivo.

TABLE 18

| Treatment (no. of mice) | Number of tumors per mouse | | | | | |
|---|---|---|---|---|---|---|
| Control PAb (4) | 23 | 48 | 28 | 26 | | |
| Anti-hPG PAb (6) | 2 | 16 | 15 | 9 | 2 | 2 |

Anti-hPG antibodies significantly reduce colorectal cancer tumors in vivo as measured by reduction in both tumor number and tumor size in a murine model of colorectal cancer, without any apparent adverse affect on normal colorectal epithelium. Thus, treatment of colorectal cancer tumors with anti-hPG provides a therapeutic benefit in vivo.

Example 10: Design of Humanized Anti-hPG Antibodies

Humanized antibodies were designed "in silico" from murine anti-hPG monoclonal antibodies MAbs 3, 4, 8, 13, 16, and 19. Design of humanized antibodies was carried out carried out according to the methodology described in Lefranc et al., 2003, Dev. Comp. Immunol. 27:55-77; Lefranc et al., 2009, Nucl. Acids Res. 37: D1006-1012; Lefranc, 2008, Mol. Biotechnol. 40: 101-111. For each of the murine monoclonal antibodies, corresponding humanized $V_H$ and $V_L$ peptide sequences were determined by: identifying the CDR and framework regions in the murine sequences using the IMGT®-ONTOLOGY database (Duroux et al., 2008, Biochimie, 90:570-583; Giudicelli and Lefranc, 1999, Bioinformatics, 15: 1047-1054) and IMGT® databases and tools (Ehrenmann et al., 2010, Nucl. Acids. Res., 38: D301-307; Brochet et al., 2008, Nucl. Acids. Res., 36: W503-508) followed by identification of the amino acid sequence of the closest human framework region sequences in the IMGT®/GENE-DB (Giudicelli et al., 2005, Nucl. Acids. Res., 33: D256-261), and grafting of the murine CDR sequences onto the human framework regions. More particularly, nucleotide and amino acid sequences of murine $V_H$ and $V_L$ domains were analyzed using IMGT®/V-QUEST and IMGT®/DomainGapAlign to delimit the murine CDRs and framework regions, define CDR lengths and identify anchor amino acids. Anchor amino acids are residues at position 26, 39, 55, 66, 104 and 118 of IMGT® "Collier de Perles" that support the CDR1-IMGT®, CDR2-IMGT®, CDR3-IMGT® (Kaas and Lefranc, 2007, Current Bioinformatics, 2: 21-30; Kaas et al., Brief. Funct. Genomic Proteomic, 2007, 6: 253-264). The closest human V (variable) and J (joining) genes to the murine sequences were identified and the most suitable genes chosen. Individual amino acids in the murine framework region were maintained if they were considered to possibly contribute to the specificity of the antibody by comparison with known 3D structures (Kaas et al., 2004, Nucl. Acids. Res. 32: 208-210) using IMGT® Collier de Perles on two layers.

$V_H$ CDRs for MAb 3 were determined to be 8, 8, and 8 amino acids long for CDR 1, 2, and 3 respectively. The closest germline mouse gene to the sequence of the murine MAb 3 $V_H$, IGHV1-5*01, differed at 10 residues, 3 of which were mapped to the CDRs and were kept in the design of humanized anti-hPG monoclonal antibodies (129 in CDR1, F56 and S65 in CDR2). In addition, V39, G55, and R66 were considered potentially important for preserving specificity and were kept in the design. The closest human germline gene was IGHV1-3*01 (63.3% identical at the amino acid level based on and IMGT®/DomainGapAlign). 27 sequence differences in the framework regions 1 to 3 were found between the murine and human germline genes. In framework region 4, Threonine-123 and Leucine-124 were changed to Leucine-123 and Valine-124, so as to match the human IGHJ1*01 gene. Overall, the humanized $V_H$ for MAb 3 is 87.8% identical to the variable region for IGHV1-46*03 and 88 of the 91 amino acids in the four framework regions are identical.

$V_L$ CDRs for MAb 3 were determined to be 11, 3, and 9 amino acids long for CDR 1, 2, and 3 respectively. The closest germline mouse gene to the sequence of the murine MAb 3 $V_L$, IGKV1-117*01, differed at a single residue mapping to a framework region. The closest human germline gene was IGKV2-30*02 (81% identical at the amino acid level based on and IMGT®/DomainGapAlign). 14 sequence differences in the framework regions 1 to 3 were found between the murine and human germline genes. Residues E40 and F68 have been maintained in the projected humanized sequence. In framework region 4, Leucine-124 was changed to Valine-124, so as to match the human IGKJ4*01 gene. Overall, the humanized Vκ sequence for MAb 3 is 93% identical to IGKV2D-29*02 and 87 of the 89 amino acids in the four framework regions are identical.

Projected $V_H$ and Vκ sequences are provided in the table below.

TABLE 19

| SEQ ID NO: | Amino acid sequence | V chain |
|---|---|---|
| 21 | QVQLVQSGAEVKKPGASVKVSCKASGYIFTSYW VHWVRQAPGQRLEWMGGFYPGNSDSRYSQKFQG RVTITRDTSASTAYMELSSLRSEDTAVYYCTRR DSPQYWGQGTLVTVSS | $hV_H3$ |
| 22 | DVVMTQSPLSLPVTLGQPASISCRSSQSIVHSN GNTYLEWFQQRPGQSPRRLIYKVSNRFSGVPDR FSGSGSGTDFTLKISRVEAEDVGVYYCFQGSHV PFTFGGGTKVEIK | hVκ3 |

$V_H$ CDRs for MAb 4 were determined to be 8, 8, and 11 amino acids long for CDR 1, 2, and 3 respectively. The closest germline mouse gene to the sequence of the murine MAb 4 $V_H$, IGHV1-9*01, differed at 11 residues, 4 of which were mapped to the CDRs and were kept in the design of humanized anti-hPG monoclonal antibodies (S35, S36, and S37 in CDR1, F56 in CDR2). In addition, D66 was considered potentially important for preserving specificity and was kept in the design. The closest human germline gene was IGHV1-46*03 (64.9% identical at the amino acid level based on and IMGT®/DomainGapAlign). 27 sequence differences in the framework regions 1 to 3 were found between the murine and human germline genes. In framework region 4, Alanine-128 was changed to Serine-128, so as to match the human IGHJ5*01 gene. Overall, the humanized $V_H$ for MAb 4 is 91.8% identical to the variable region for IGHV1-46*03 and 90 of the 91 amino acids in the four framework regions are identical.

$V_L$ CDRs for MAb 4 were determined to be 11, 3, and 9 amino acids long for CDR 1, 2, and 3 respectively. The closest germline mouse gene to the sequence of the murine MAb 4 $V_L$, IGKV1-110*01, differed at 3 residues, 2 of which were mapped to CDR1 (Serine-34 and Valine-36) and were kept in the design of humanized anti-hPG monoclonal antibodies. The closest human germline gene was IGKV2D-29*02 (81% identical at the amino acid level based on and IMGT®/DomainGapAlign). 11 sequence differences in the framework regions 1 to 3 were found between the murine and human germline genes. In framework region 4, Serine-120 was changed to Glutamine-120, so as to match the human IGKJ2*01 gene. Overall, the humanized Vκ sequence for MAb 4 is 92% identical to IGKV2D-29*02 and 100% identical for the four framework regions.

Projected $V_H$ and Vκ sequences are provided in the table below.

TABLE 20

| SEQ ID NO: | Amino acid sequence | V chain |
|---|---|---|
| 23 | QVQLVQSGAEVKKPGASVKVSCKASGYTFSSSWMHW VRQAPGQGLEWMGIFLPGSGSTDYAQKFQGRVTMTR DTSTSTVYMELSSLRSEDTAVYYCATDGNYDWFAYW GQGTLVTVSS | $hV_H4$ |
| 24 | DIVMTQTPLSLSVTPGQPASISCKSSQSLVHSSGVT YLYWYLQKPGQSPQLLIYKVSNRFSGVPDRFSGSGS GTDFTLKISRVEAEDVGVYYCSQSTHVPPTFGQGTK LEIK | hVκ4 |

$V_H$ CDRs for MAb 8 were determined to be 8, 8, and 10 amino acids long for CDR 1, 2, and 3 respectively. The closest germline mouse gene to the sequence of the murine MAb8 $V_H$, IGHV5-9-3*01, differed at 5 residues, 4 of which were mapped to the CDRs and were kept in the design of humanized anti-hPG monoclonal antibodies. The closest human germline genes were IGHV3-21*01 and *02 (80.4% identical at the amino acid level based on and IMGT®/DomainGapAlign). 12 sequence differences in the framework regions 1 to 3 were found between the murine and human germline genes. In framework region 4, Serine-123 and Leucine-124 were changed to Threonine-123 and Valine-124, respectively, so as to match the human IGHJ6*01 gene. Overall, the humanized $V_H$ for MAb 8 is 92.8% identical to the variable region for IGHV3-21*01 and *02 and 100% identical for the four framework regions. There is a potential N-glycosylation site in murine $V_H$ CDR3 for MAb8.

$V_L$ CDRs for MAb 8 were determined to be 11, 3, and 9 amino acids long for CDR 1, 2, and 3 respectively. The closest germline mouse gene to the sequence of the murine MAb 8 $V_L$, IGKV2-109*01, differed at 6 residues, 4 of which were mapped to CDR1 and were kept in the design of humanized anti-hPG monoclonal antibodies. The closest human germline genes were IGKV2-28*01 and IGKV2D-28*01 (75% identical at the amino acid level based on and IMGT®/DomainGapAlign). 12 sequence differences in the framework regions 1 to 3 were found between the murine and human germline genes. In framework region 4, Alanine-120, Leucine-124, and Leucine 126 were changed to Glycine-120, Valine-124, and Isoleucine-126, respectively, so as to match the human IGKJ4*01 gene. Overall, the humanized Vκ sequence for MAb 8 is 87% identical to IGKV2-28*01 and IGKV2D-28*01 and 100% identical for the four framework regions.

Projected $V_H$ and Vκ sequences are provided in the table below.

TABLE 21

| SEQ ID NO: | Amino acid sequence | V chain |
|---|---|---|
| 75 | EVQLVESGGGLVKPGGSLRLSCAASGFT FTTYAMNWVRQAPGKGLEWVSSISSGGT YTYYADSVKGRFTISRDNAKNSLYLQMN SLRAEDTAVYYCATQGNYSLDFWGQGTT VTVSS | hVH8a |
| 76 | DIVMTQSPLSLPVTPGEPA SISCRSSKSLRHTKGITFLD WYLQKPGQSPQLLIYQMSNRASGVPD RFSGSGSGTDFTLKISRVEAEDVG VYYCAQNLELPLTFGGGTKVEIK | hVκ8a |
| 77 | EVQLVESGGGLVKPGGSLRLSCAA SGFTFTTYAMSWVRQAPGKGLEWVS SISSGGTYTYYADSVKG RFTISRDNAKNSLYLQMNSLRAEDTA VYYCATQGNYSLDFWGQGTTVTVSS | $hV_H8b$ |
| 78 | DIVMTQSPLSLPVTPGEPASISC RSSKSLRHTKGITFLYWYLQKPG QSPQLLIYQMSNRASGVPD RFSGSGSGTDFTLKISRVEAED VGVYYCAQNLELPLTFGGGTKVEIK | hVκ8b |
| 79 | EVQLVESGGGLVKPGGSLRLSCAASGF TFTTYAMSWVRQAPGKGLEWVSTISSG GTYTYYADSVKGRFTISRDNAKNSLYL QMNSLRAEDTAVYYCATQGNYSLDFWGQGTTVTVSS | $hV_H8b$ |

$V_H$ CDRs for MAb 13 were determined to be 8, 8, and 7 amino acids long for CDR 1, 2, and 3 respectively. The closest germline mouse gene to the sequence of the murine MAb 13 $V_H$, IGHV5-6-3*01, differed at 10 residues, 5 of which were mapped to the CDRs and were kept in the design of humanized anti-hPG monoclonal antibodies. The closest human germline genes were IGHV3-7*01 and *02 (78.6% identical at the amino acid level based on and IMGT®/DomainGapAlign). 13 sequence differences in the framework regions 1 to 3 were found between the murine and human germline genes. In framework region 4, Threonine-123 and Leucine-124 were changed to Leucine-123 and Valine-124, respectively, so as to match the human IGHJ4*01 gene. Overall, the humanized $V_H$ for MAb 13 is 91.8% identical to the variable region for IGHV3-7*01 and *02 and 100% identical for the four framework regions.

$V_L$ CDRs for MAb 13 were determined to be 11, 3, and 9 amino acids long for CDR 1, 2, and 3 respectively. The closest germline mouse gene to the sequence of the murine MAb 13 $V_L$, IGKV1-135*01, differed at a single residue located in a framework region. The closest human germline genes were IGKV2-30*01 and *02 (81% identical at the amino acid level based on and IMGT®/DomainGapAlign). 13 sequence differences in the framework regions 1 to 3 were found between the murine and human germline genes. In framework region 4, Leucine-124 was changed to Valine-124, so as to match the human IGKJ4*01 gene. Overall, the humanized Vκ sequence for MAb 13 is 94% identical to IGKV2-30*01 and *02 and 100% identical for the four framework regions.

Projected $V_H$ and Vκ sequences are provided in the table below.

TABLE 22

| SEQ ID NO: | Amino acid sequence | V chain |
|---|---|---|
| 80 | EVQLVESGGGLVQPGGSLRLSCAASGFIFSSYGMSW VRQAPGKGLEWVANINTFGDRTYYVDSVKGRFTISR DNAKNSLYLQMNSLRAEDTAVYYCARGTGTYWGQGT LVTVSS | $hV_H$.13a |
| 81 | DVVMTQSPLSLPVTLGQPASISCRSSQSLLDSDGKT YLNWFQQRPGQSPRRLIYLVSNRDSGVPDRFSGSGS GTDFTLKISRVEAEDVGVYYCWQGTHFPQTFGGGTK VEIK | hVκ13a |
| 82 | EVQLVESGGGLVQPGGSLRLSCAASGFIFSSYGMSW VRQAPGKGLEWVASINTFGDRTYYVDSVKGRFTISR LDNAKNSYLQMNSLRAEDTAVYYCARGTGTYWGQGT LVTVSS | $hV_H$13b |
| 83 | DVVMTQSPLSLPVTLGQPASISCRSSQSLLDSDGKT YLNWFQQRPGQSPRRLIYLVSKRDSGVPDRFSGSGS GTDFTLKISRVEAEDVGVYYCWQGTHFPQTFGGGTK VEIK | hVκ13b |

$V_H$ CDRs for MAb 16 were determined to be 8, 8, and 10 amino acids long for CDR 1, 2, and 3 respectively. The closest germline mouse gene to the sequence of the murine MAb 16, $V_H$, IGHV1-53*01, differed at 7 residues, 2 of which were mapped to the CDRs and were kept in the design of humanized anti-hPG monoclonal antibodies. The closest human germline genes were IGHV1-46*01 and *03 (71.4% identical at the amino acid level based on and IMGT®/DomainGapAlign). 25 sequence differences in the framework regions 1 to 3 were found between the murine and human germline genes. In framework region 4, Leucine-124 was changed to Valine-124, so as to match the human IGHJ6*01 gene. Overall, the humanized $V_H$ for MAb 16 is 96.9% identical to the variable region for IGHV1-46*01 and *03 and 100% identical for the four framework regions.

$V_L$ CDRs for MAb 16 were determined to be 11, 3, and 9 amino acids long for CDR 1, 2, and 3 respectively. The closest germline mouse gene to the sequence of the murine MAb 16, $V_L$, IGKV1-135*01, differed at 4 residues located in a framework region. The closest human germline genes were IGKV2-30*01 and *02 (79% identical at the amino acid level based on and IMGT®/DomainGapAlign), that differed by one amino acid in CDR1. 15 sequence differences in the framework regions 1 to 3 were found between the murine and human germline genes. In framework region 4, Glycine-120 was changed to Glutamine-120, so as to match the human IGKJ2*01 gene. Overall, the humanized Vκ sequence for MAb 16 is 94% identical to IGKV2-30*01 and *02 and 100% identical for the four framework regions.

Projected $V_H$ and Vκ sequences are provided in the table below.

TABLE 23

| SEQ ID NO: | Amino acid sequence | V chain |
|---|---|---|
| 84 | QVQLVQSGAEVKKPGASVKVSCKASGYTFTSYYMHW VRQAPGQGLEWMGIINPSNGGTSYAQKFQGRVTMTR DTSTSTVYMELSSLRSEDTAVYYCTRGGYYPFDYWG QGTTVTVSS | $hV_H$16a |
| 85 | DVVMTQSPLSLPVTLGQPASISCRSSQSLLDSDGKT YLNWFQQRPGQSPRRLIYLVSNRDSGVPDRFSGSGS GTDFTLKISRVEAEDVGVYYCWQGTHSPYTFGQGTK LEIK | hVκ16a |
| 86 | QVQLVQSGAEVKKPGASVKVSCKASGYTFTSYYMYW VRQAPGQGLEWMGIINPSNGGTSYAQKFQGRVTMTR DTSTSTVYMELSSLRSEDTAVYYCTRGGYYPFDYWG QGTTVTVSS | $hV_H$16b |
| 87 | DVVMTQSPLSLPVTLGQPASISCRSSQSLLDSDGKT YLYWFQQRPGQSPRRLIYLVSNRDSGVPDRFSGSGS GTDFTLKISRVEAEDVGVYYCWQGTHSPYTFGQGTK LEIK | hVκ16b |
| 88 | QVQLVQSGAEVKKPGASVKVSCKASGYTFTSYYMYW VRQAPGQGLEWMGEINPSNGGTNYAQKFQGRVTMTR DTSTSTVYMELSSLRSEDTAVYYCTRGGYYPFDYWG QGTTVTVSS | $hV_H$16c |
| 89 | DVVMTQSPLSLPVTLGQPASISCRSSQSLLDSDGKT YLYWFQQRPGQSPRRLIYLVSERDSGVPDRFSGSGS GTDFTLKISRVEAEDVGVYYCWQGTHSPYTFGQGTK LEIK | hVκ16c |

$V_H$ CDRs for MAb 19 were determined to be 9, 7, and 14 amino acids long for CDR 1, 2, and 3 respectively. The closest germline mouse gene to the sequence of the murine MAb 19 $V_H$, IGHV3-2*01, differed at 5 residues, 2 of which were mapped to the CDRs and were kept in the design of humanized anti-hPG monoclonal antibodies. The closest human germline gene was IGHV4-30-4*01 (72.4% identical at the amino acid level based on and IMGT®/DomainGapAlign). However, since this gene is polymorphic, IGHV4-31*02 and *03 (71.4% identical at the amino acid level based on and IMGT®/DomainGapAlign) were selected. 21 sequence differences in the framework regions 1 to 3 were found between the murine and human germline genes. In framework region 4, Isoleucine-123 was changed to Leucine-123, so as to match the human IGHJ4*01 gene. Overall, the humanized $V_H$ for MAb 19 is 91.9% identical to the variable region for IGHV4-31*02 and *03 and 100% identical for the four framework regions.

$V_L$ CDRs for MAb 19 were determined to be 7, 7, and 13 amino acids long for CDR 1, 2, and 3 respectively. The closest germline mouse gene to the sequence of the murine MAb 19 $V_L$, IGLV3*01, differed at 8 residues, 5 of which were located in a CDR. The closest human germline genes were IGLV4-69*01 and *02 (69.9% identical at the amino acid level based on and IMGT®/DomainGapAlign). 23 sequence differences in the framework regions 1 to 3 were found between the murine and human germline genes. In framework region 4, Valine-124 was changed to Leucine-124, so as to match the human IGLJ3*01 gene. Alternatively, the IGJK4*01 gene can be used for the framework 4 region. Overall, the humanized Vκ sequence for MAb 19 is 92.4% identical to IGLV4-69*01 and *02 and 100% identical for the four framework regions.

Projected $V_H$ and Vκ sequences are provided in the table below.

TABLE 24

| SEQ ID NO: | Amino acid sequence | V chain |
|---|---|---|
| 90 | QVQLQESGPGLVKPSQTLSLTCTVSGYSITSDYAW SWIRQHPGKGLEWIGYISFSGYTYYNPSLKSRVTI SVDTSKNQFSLKLSSVTAADTAVYYCAREVNYGDS YHFDYWGQGTLVTVSS | $V_H$19a |
| 91 | QLVLTQSPSASASLGASVKLTCTLSSQHRTYTIAW HQQQPEKGPRYLMKVKKDGSHSKGDGIPDRFSGSS SGAERYLTISSLQSEDEADYYCGVGDAIKGQSVFV FGGGTKVEIK | Vκ19a |
| 92 | QVQLQESGPGLVKPSQTLSLTCTVSGYSITSDYAW NWIRQHPGKGLEWIGYISFSGYTYYNPSLKSRVTI VTSVDTSKNQFSLKLSSAADTAVYYCAREVNYGDS YHFDYWGQGTLVTVSS | $V_H$19b |
| 93 | QLVLTQSPSASASLGASVKLTCTLSSQHRTYTIEW HQQQPEKGPRYLMKVKKDGSHSKGDGIPDRFSGSS SGAERYLTISSLQSEDEADYYCGVGDAIKGQSVFV FGGGTKVEIK | Vκ19b |
| 94 | QVQLQESGPGLVKPSQTLSLTCTVSGYSITSDYAW NWIRQHPGKGLEWIGYISFSGYTSYNPSLKSRVTI SVDTSKNQFSLKLSSVTAADTAVYYCAREVNYGDS YHFDYWGQGTLVTVSS | $V_H$19c |
| 95 | QLVLTQSPSASASLGASVKLTCTLSSQHRTYTIEW HQQQPEKGPRYLMEVKKDGSHSKGDGIPDRFSGSS SGAERYLTISSLQSEDEADYYCGVGDAIKGQSVFV FGGGTKVEIK | Vκ19c |

All publications, patents, patent applications and other documents cited in this application are hereby incorporated by reference in their entireties for all purposes to the same extent as if each individual publication, patent, patent application or other document were individually indicated to be incorporated by reference for all purposes. While various specific embodiments have been illustrated and described, it will be appreciated that various changes can be made without departing from the spirit and scope of the invention(s).

What is claimed is:

1. A monoclonal antibody that specifically binds a human progastrin (hPG) polypeptide having an amino acid sequence of SEQ ID NO:20, but does not detectably bind to an amidated gastrin 17 consisting of SEQ ID NO:103, a glycine-extended gastrin 17 consisting of SEQ ID NO:104, or C-terminal Flanking Peptide (CTFP) consisting of SEQ ID NO:105, wherein said monoclonal antibody is an N-terminal anti-hPG monoclonal antibody that specifically binds an N-terminal region of hPG, wherein:

(a) the antibody is obtainable using an immunogen comprising a peptide antigen having an amino acid sequence of SEQ ID NO: 25; and (b) the antibody comprises $V_H$ CDRs comprising amino acid sequences of $V_H$ CDR 1.19 (SEQ ID NO:40), $V_H$ CDR 2.19 (SEQ ID NO:44), $V_H$ CDR 3.19 (SEQ ID NO:48) and $V_L$ CDRs comprising amino acid sequences of $V_L$ CDR 1.19 (SEQ ID NO:51), $V_L$ CDR 2.19 (SEQ ID NO:54), and $V_L$ CDR 3.19 (SEQ ID NO:58).

2. The monoclonal antibody of claim 1 that comprises a $V_H$ of SEQ ID NO:62 and a $V_L$ of SEQ ID NO:66.

3. The monoclonal antibody of claim 1 that comprises $V_H$ and $V_L$ chains having sequences selected from one of the following groups of $V_H$ and $V_L$ sequences:

(i) h$V_H$ 19a (SEQ ID NO:90) and h$V_L$ 19a (SEQ ID NO:91);

(ii) h$V_H$ 19b (SEQ ID NO:92) and h$V_L$ 19b (SEQ ID NO:93); and (iii) h$V_H$ 19c (SEQ ID NO:94) and h$V_L$ 19c (SEQ ID NO:95).

4. A monoclonal antibody that specifically binds a human progastrin (hPG) polypeptide and comprises a $V_H$ chain comprising CDRs having the amino acid sequence of $V_H$ CDR 1.19 (SEQ ID NO:40), $V_H$ CDR 2.19 (SEQ ID NO:44), $V_H$ CDR 3.19 (SEQ ID NO:48), and a $V_L$ chain comprising CDRs having the amino acid sequence of $V_L$ CDR 1.19 (SEQ ID NO:51), $V_L$ CDR 2.19 (SEQ ID NO:54), and $V_L$ CDR 3.19 (SEQ ID NO:58).

5. The monoclonal antibody of claim 4, which reduces the binding of a reference antibody to hPG by at least 40% when said monoclonal antibody and the reference antibody are each used at a concentration of 10 μg/ml.

6. The monoclonal antibody of claim 5, which neutralizes hPG activity in an in vitro assay.

7. The monoclonal antibody of claim 4, which is humanized.

8. The monoclonal antibody of claim 7, which comprises $V_H$ and $V_L$ chains having amino acid sequences of:

(i) h$V_H$ 19a (SEQ ID NO:90) and h$V_L$ 19a (SEQ ID NO:91);

(ii) h$V_H$ 19b (SEQ ID NO:92) and h$V_L$ 19b (SEQ ID NO:93); and (iii) h$V_H$ 19c (SEQ ID NO:94) and h$V_L$ 19c (SEQ ID NO:95).

9. A composition comprising the monoclonal antibody according to claim 4 and an excipient, carrier, and/or diluent.

10. The composition of claim 9 which is formulated for pharmaceutical use.

11. A polynucleotide encoding a variable light chain for the monoclonal antibody according to claim 4.

12. A polynucleotide encoding a variable heavy chain for the monoclonal antibody according to claim 4.

13. An expression vector comprising a polynucleotide encoding a variable light chain for the monoclonal antibody according to claim 4.

14. An expression vector comprising a polynucleotide encoding a variable heavy chain for the monoclonal antibody according to claim 4.

15. A cell line transformed with pairs of polynucleotides suitable for expressing the monoclonal antibody according to claim 4.

16. A method of obtaining an anti-human progastrin monoclonal antibody comprising:

(a) culturing the cell line of claim 15 under suitable conditions; and (b) recovering said monoclonal antibody from the culture medium or cells of the cell line.

17. A cell line capable of secreting the monoclonal antibody according to claim 4.

18. A kit useful for detecting human progastrin (hPG) polypeptide, comprising the monoclonal antibody according to claim 4 and an antibody that specifically binds a C-terminal region of hPG.

19. The kit of claim 18, wherein the antibody that specifically binds a C-terminal region of hPG is a polyclonal antibody.

20. A cell line which recombinantly expresses an anti-human progastrin antibody comprising a $V_H$ of SEQ ID NO:62 and a $V_L$ of SEQ ID NO:66.

* * * * *

SEQUENCE LISTING

```
<160> NUMBER OF SEQ ID NOS: 105

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Ile Phe Thr Ser Tyr Trp
1               5


<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Tyr Pro Gly Asn Ser Asp Ser
1               5


<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 3

Thr Arg Arg Asp Ser Pro Gln Tyr
1 5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

Gln Ser Ile Val His Ser Asn Gly Asn Thr Tyr
1 5 10

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Lys Val Ser
1

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Phe Gln Gly Ser His Val Pro Phe Thr
1 5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Gly Tyr Thr Phe Ser Ser Ser Trp
1 5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Phe Leu Pro Gly Ser Gly Ser Thr
1 5

<210> SEQ ID NO 9

<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

```
Ala Thr Asp Gly Asn Tyr Asp Trp Phe Ala Tyr
1               5                   10
```

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

```
Gln Ser Leu Val His Ser Ser Gly Val Thr Tyr
1               5                   10
```

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

```
Ser Gln Ser Thr His Val Pro Pro Thr
1               5
```

<210> SEQ ID NO 12
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ile Phe Thr Ser Tyr
            20                  25                  30

Trp Val His Trp Val Lys Gln Arg Pro Gly Gln Gly Leu Glu Trp Ile
        35                  40                  45

Gly Gly Phe Tyr Pro Gly Asn Ser Asp Ser Arg Tyr Asn Gln Lys Phe
    50                  55                  60

Lys Gly Lys Ala Thr Leu Thr Ala Val Thr Ser Ala Ser Thr Ala Tyr
65                  70                  75                  80

Met Asp Leu Ser Ser Leu Thr Asn Glu Asp Ser Ala Val Tyr Phe Cys
                85                  90                  95

Thr Arg Arg Asp Ser Pro Gln Tyr Trp Gly Gln Gly Thr Thr Leu Thr
            100                 105                 110

Val Ser Ser
        115
```

<210> SEQ ID NO 13
<211> LENGTH: 112
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 13

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Leu Glu Ala Glu Asp Leu Gly Val Tyr Tyr Cys Phe Gln Gly
                85                  90                  95

Ser His Val Pro Phe Thr Phe Gly Gly Gly Thr Lys Leu Glu Ile Lys
            100                 105                 110


<210> SEQ ID NO 14
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Ser
            20                  25                  30

Trp Ile Glu Trp Leu Lys Gln Arg Pro Gly His Gly Leu Glu Trp Ile
        35                  40                  45

Gly Glu Phe Leu Pro Gly Ser Gly Ser Thr Asp Tyr Asn Glu Lys Phe
    50                  55                  60

Lys Gly Lys Ala Thr Phe Thr Ala Asp Thr Ser Ser Asp Thr Ala Tyr
65                  70                  75                  80

Met Leu Leu Ser Ser Leu Thr Ser Glu Asp Ser Ala Val Tyr Tyr Cys
                85                  90                  95

Ala Thr Asp Gly Asn Tyr Asp Trp Phe Ala Tyr Trp Gly Gln Gly Thr
            100                 105                 110

Leu Val Thr Val Ser Ala
        115


<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Leu Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30
```

```
Ser Gly Val Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Ser Gly Thr Lys Leu Glu Ile Lys
            100                 105                 110


<210> SEQ ID NO 16
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(345)

<400> SEQUENCE: 16

gag gtt cag ctc cag cag tct ggg act gtg ctg gca agg cct ggg gct       48
Glu Val Gln Leu Gln Gln Ser Gly Thr Val Leu Ala Arg Pro Gly Ala
1               5                   10                  15

tcc gtg aag atg tcc tgc aag gct tct ggc tac atc ttt acc agc tac       96
Ser Val Lys Met Ser Cys Lys Ala Ser Gly Tyr Ile Phe Thr Ser Tyr
            20                  25                  30

tgg gta cac tgg gtt aaa cag agg cct gga cag ggt cta gaa tgg att      144
Trp Val His Trp Val Lys Gln Arg Pro Gly Gln Gly Leu Glu Trp Ile
        35                  40                  45

ggt ggt ttt tat cct gga aat agt gat tct agg tac aac cag aaa ttc      192
Gly Gly Phe Tyr Pro Gly Asn Ser Asp Ser Arg Tyr Asn Gln Lys Phe
    50                  55                  60

aag ggc aag gcc aca ctg act gca gtc aca tcc gcc agt act gcc tac      240
Lys Gly Lys Ala Thr Leu Thr Ala Val Thr Ser Ala Ser Thr Ala Tyr
65                  70                  75                  80

atg gac ctc agc agc ctg aca aat gag gac tct gcg gtc tat ttc tgt      288
Met Asp Leu Ser Ser Leu Thr Asn Glu Asp Ser Ala Val Tyr Phe Cys
                85                  90                  95

aca aga aga gat agt ccc cag tac tgg ggc caa ggc acc act ctc aca      336
Thr Arg Arg Asp Ser Pro Gln Tyr Trp Gly Gln Gly Thr Thr Leu Thr
            100                 105                 110

gtc tcc tca                                                          345
Val Ser Ser
        115


<210> SEQ ID NO 17
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 17

gat gtt ttg atg acc caa act cca ctc tcc ctg cct gtc agt ctt gga       48
Asp Val Leu Met Thr Gln Thr Pro Leu Ser Leu Pro Val Ser Leu Gly
1               5                   10                  15
```

```
gat caa gcc tcc atc tct tgc aga tct agt cag agc att gta cat agt       96
Asp Gln Ala Ser Ile Ser Cys Arg Ser Ser Gln Ser Ile Val His Ser
            20                  25                  30

aat gga aac acc tat tta gaa tgg tac ctg cag aaa cca ggc cag tct      144
Asn Gly Asn Thr Tyr Leu Glu Trp Tyr Leu Gln Lys Pro Gly Gln Ser
        35                  40                  45

cca aag ctc ctg atc tac aaa gtt tcc aac cga ttt tct ggg gtc cca      192
Pro Lys Leu Leu Ile Tyr Lys Val Ser Asn Arg Phe Ser Gly Val Pro
    50                  55                  60

gac agg ttc agt ggc agt gga tca ggg aca gat ttc aca ctc aag atc      240
Asp Arg Phe Ser Gly Ser Gly Ser Gly Thr Asp Phe Thr Leu Lys Ile
65                  70                  75                  80

agc aga ctg gag gct gag gat ctg gga gtt tat tac tgc ttt caa ggt      288
Ser Arg Leu Glu Ala Glu Asp Leu Gly Val Tyr Tyr Cys Phe Gln Gly
                85                  90                  95

tca cat gtt ccg ttc acg ttc gga ggg ggg acc aag ctg gaa ata aaa      336
Ser His Val Pro Phe Thr Phe Gly Gly Gly Thr Lys Leu Glu Ile Lys
            100                 105                 110
```

<210> SEQ ID NO 18
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(354)

<400> SEQUENCE: 18

```
cag gtt cag ttg cag cag tct gga gct gag ctg atg aag cca ggg gcc       48
Gln Val Gln Leu Gln Gln Ser Gly Ala Glu Leu Met Lys Pro Gly Ala
1               5                   10                  15

tca gtg aag ata tcc tgc aag gct act ggc tac aca ttc agt agc tcc       96
Ser Val Lys Ile Ser Cys Lys Ala Thr Gly Tyr Thr Phe Ser Ser Ser
            20                  25                  30

tgg ata gag tgg tta aaa cag agg cct gga cat ggc ctt gag tgg att      144
Trp Ile Glu Trp Leu Lys Gln Arg Pro Gly His Gly Leu Glu Trp Ile
        35                  40                  45

gga gag ttt tta cct gga agt ggt agt aca gac tac aat gag aag ttc      192
Gly Glu Phe Leu Pro Gly Ser Gly Ser Thr Asp Tyr Asn Glu Lys Phe
    50                  55                  60

aag ggc aag gcc aca ttc act gca gac aca tcc tcc gac aca gcc tac      240
Lys Gly Lys Ala Thr Phe Thr Ala Asp Thr Ser Ser Asp Thr Ala Tyr
65                  70                  75                  80

atg cta ctc agc agc ctg aca tct gag gac tct gcc gtc tat tac tgt      288
Met Leu Leu Ser Ser Leu Thr Ser Glu Asp Ser Ala Val Tyr Tyr Cys
                85                  90                  95

gca act gat ggt aat tat gac tgg ttt gct tac tgg ggc caa ggg act      336
Ala Thr Asp Gly Asn Tyr Asp Trp Phe Ala Tyr Trp Gly Gln Gly Thr
            100                 105                 110

ctg gtc act gtc tct gca                                              354
Leu Val Thr Val Ser Ala
        115
```

<210> SEQ ID NO 19
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

```
<220> FEATURE:
<221> NAME/KEY: CDS
<222> LOCATION: (1)..(336)

<400> SEQUENCE: 19

gat ctt gtg atg acc caa act cca ctc tcc ctg cct gtc agt ctt gga       48
Asp Leu Val Met Thr Gln Thr Pro Leu Ser Leu Pro Val Ser Leu Gly
1               5                   10                  15

gat caa gcc tcc atc tct tgc aga tct agt cag agc ctt gta cac agt       96
Asp Gln Ala Ser Ile Ser Cys Arg Ser Ser Gln Ser Leu Val His Ser
            20                  25                  30

agt gga gtc acc tat tta cat tgg tac ctg cag aag cca ggc cag tct      144
Ser Gly Val Thr Tyr Leu His Trp Tyr Leu Gln Lys Pro Gly Gln Ser
        35                  40                  45

cca aag ctc ctg atc tac aaa gtt tcc aac cga ttt tct ggg gtc cca      192
Pro Lys Leu Leu Ile Tyr Lys Val Ser Asn Arg Phe Ser Gly Val Pro
    50                  55                  60

gac agg ttc agt ggc agt gga tca ggg aca gat ttc aca ctc aag atc      240
Asp Arg Phe Ser Gly Ser Gly Ser Gly Thr Asp Phe Thr Leu Lys Ile
65                  70                  75                  80

agc aga gtg gag gct gag gat ctg gga gtt tat ttc tgc tct caa agt      288
Ser Arg Val Glu Ala Glu Asp Leu Gly Val Tyr Phe Cys Ser Gln Ser
                85                  90                  95

aca cat gtt cct ccc acg ttc ggc tcg ggg aca aag ttg gaa ata aaa      336
Thr His Val Pro Pro Thr Phe Gly Ser Gly Thr Lys Leu Glu Ile Lys
            100                 105                 110


<210> SEQ ID NO 20
<211> LENGTH: 80
<212> TYPE: PRT
<213> ORGANISM: Homo sapiens

<400> SEQUENCE: 20

Ser Trp Lys Pro Arg Ser Gln Gln Pro Asp Ala Pro Leu Gly Thr Gly
1               5                   10                  15

Ala Asn Arg Asp Leu Glu Leu Pro Trp Leu Glu Gln Gln Gly Pro Ala
            20                  25                  30

Ser His His Arg Arg Gln Leu Gly Pro Gln Gly Pro Pro His Leu Val
        35                  40                  45

Ala Asp Pro Ser Lys Lys Gln Gly Pro Trp Leu Glu Glu Glu Glu Glu
    50                  55                  60

Ala Tyr Gly Trp Met Asp Phe Gly Arg Arg Ser Ala Glu Asp Glu Asn
65                  70                  75                  80


<210> SEQ ID NO 21
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
            20                  25                  30

Trp Val His Trp Val Arg Gln Ala Pro Gly Gln Arg Leu Glu Trp Met
        35                  40                  45

Gly Gly Phe Tyr Pro Gly Asn Ser Asp Ser Arg Tyr Ser Gln Lys Phe
    50                  55                  60
```

```
Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Arg Asp Ser Pro Gln Tyr Trp Gly Gln Gly Thr Leu Val Thr
            100                 105                 110

Val Ser Ser
        115


<210> SEQ ID NO 22
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gly Gly Thr Lys Val Glu Ile Lys
            100                 105                 110


<210> SEQ ID NO 23
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Ser
            20                  25                  30

Trp Met His Trp Val Arg Gln Ala Pro Gly Gln Gly Leu Glu Trp Met
        35                  40                  45

Gly Ile Phe Leu Pro Gly Ser Gly Ser Thr Asp Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Asp Gly Asn Tyr Asp Trp Phe Ala Tyr Trp Gly Gln Gly Thr
            100                 105                 110

Leu Val Thr Val Ser Ser
        115
```

```
<210> SEQ ID NO 24
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Ser
            20                  25                  30

Ser Gly Val Thr Tyr Leu Tyr Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Pro Thr Phe Gly Gln Gly Thr Lys Leu Glu Ile Lys
            100                 105                 110


<210> SEQ ID NO 25
<211> LENGTH: 14
<212> TYPE: PRT
<213> ORGANISM: Homo sapiens

<400> SEQUENCE: 25

Ser Trp Lys Pro Arg Ser Gln Gln Pro Asp Ala Pro Leu Gly
1               5                   10


<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Ahx

<400> SEQUENCE: 26

Ser Trp Lys Pro Arg Ser Gln Gln Pro Asp Ala Pro Leu Gly Xaa Cys
1               5                   10                  15


<210> SEQ ID NO 27
<211> LENGTH: 26
<212> TYPE: PRT
<213> ORGANISM: Homo sapiens

<400> SEQUENCE: 27

Gln Gly Pro Trp Leu Glu Glu Glu Glu Glu Ala Tyr Gly Trp Met Asp
1               5                   10                  15

Phe Gly Arg Arg Ser Ala Glu Asp Glu Asn
            20                  25


<210> SEQ ID NO 28
<211> LENGTH: 5
```

<212> TYPE: PRT
<213> ORGANISM: Homo sapiens

<400> SEQUENCE: 28

Asp Ala Pro Leu Gly
1 5

<210> SEQ ID NO 29
<211> LENGTH: 6
<212> TYPE: PRT
<213> ORGANISM: Homo sapiens

<400> SEQUENCE: 29

Pro Asp Ala Pro Leu Gly
1 5

<210> SEQ ID NO 30
<211> LENGTH: 7
<212> TYPE: PRT
<213> ORGANISM: Homo sapiens

<400> SEQUENCE: 30

Pro Arg Ser Gln Gln Pro Asp
1 5

<210> SEQ ID NO 31
<211> LENGTH: 9
<212> TYPE: PRT
<213> ORGANISM: Homo sapiens

<400> SEQUENCE: 31

Trp Lys Pro Arg Ser Gln Gln Pro Asp
1 5

<210> SEQ ID NO 32
<211> LENGTH: 13
<212> TYPE: PRT
<213> ORGANISM: Homo sapiens

<400> SEQUENCE: 32

Trp Lys Pro Arg Ser Gln Gln Pro Asp Ala Pro Leu Gly
1 5 10

<210> SEQ ID NO 33
<211> LENGTH: 4
<212> TYPE: PRT
<213> ORGANISM: Homo sapiens

<400> SEQUENCE: 33

Phe Gly Arg Arg
1

<210> SEQ ID NO 34
<211> LENGTH: 5
<212> TYPE: PRT
<213> ORGANISM: Homo sapiens

<400> SEQUENCE: 34

Met Asp Phe Gly Arg
1 5

<210> SEQ ID NO 35
<211> LENGTH: 5
<212> TYPE: PRT
<213> ORGANISM: Homo sapiens

<400> SEQUENCE: 35

Ala Glu Asp Glu Asn
1 5

<210> SEQ ID NO 36
<211> LENGTH: 8
<212> TYPE: PRT
<213> ORGANISM: Homo sapiens

<400> SEQUENCE: 36

Gly Trp Met Asp Phe Gly Arg Arg
1 5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Gly Phe Thr Phe Thr Thr Tyr Ala
1 5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Gly Phe Ile Phe Ser Ser Tyr Gly
1 5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

Gly Tyr Thr Phe Thr Ser Tyr Tyr
1 5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

Gly Tyr Ser Ile Thr Ser Asp Tyr Ala
1 5

<210> SEQ ID NO 41
<211> LENGTH: 8
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 41

Ile Ser Ser Gly Gly Thr Tyr Thr
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ile Asn Thr Phe Gly Asp Arg Thr
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ile Asn Pro Ser Asn Gly Gly Thr
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile Ser Phe Ser Gly Tyr Thr
1               5

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Thr Gln Gly Asn Tyr Ser Leu Asp Phe
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Arg Gly Thr Gly Thr Tyr
1               5

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Thr Arg Gly Gly Tyr Tyr Pro Phe Asp Tyr
1 5 10

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 48

Ala Arg Glu Val Asn Tyr Gly Asp Ser Tyr His Phe Asp Tyr
1 5 10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

Lys Ser Leu Arg His Thr Lys Gly Ile Thr Phe
1 5 10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Gln Ser Leu Leu Asp Ser Asp Gly Lys Thr Tyr
1 5 10

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Ser Gln His Arg Thr Tyr Thr
1 5

<210> SEQ ID NO 52
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Gln Met Ser
1

<210> SEQ ID NO 53
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Leu Val Ser
1

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Val Lys Lys Asp Gly Ser His
1 5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

Ala Gln Asn Leu Glu Leu Pro Leu Thr
1 5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

Trp Gln Gly Thr His Phe Pro Gln Thr
1 5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

Trp Gln Gly Thr His Ser Pro Tyr Thr
1 5

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 58

Gly Val Gly Asp Ala Ile Lys Gly Gln Ser Val Phe Val
1 5 10

<210> SEQ ID NO 59
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 59

Glu Val Gln Leu Val Glu Ser Gly Gly Gly Leu Val Lys Pro Gly Gly
1 5 10 15

Ser Leu Lys Leu Ser Cys Ala Ala Ser Gly Phe Thr Phe Thr Thr Tyr
20 25 30

Ala Met Ser Trp Val Arg Gln Thr Pro Glu Lys Arg Leu Glu Trp Val
35 40 45

Ala Thr Ile Ser Ser Gly Gly Thr Tyr Thr Tyr Tyr Pro Asp Ser Val
50 55 60

Lys Gly Arg Phe Thr Ile Ser Arg Asp Asn Ala Lys Asn Ala Leu Tyr
65 70 75 80

Leu Gln Met Ser Ser Leu Arg Ser Glu Asp Thr Ala Met Tyr Tyr Cys
85 90 95

Ala Thr Gln Gly Asn Tyr Ser Leu Asp Phe Trp Gly Gln Gly Thr Ser
100 105 110

Leu Thr Val Ser Ser
115

<210> SEQ ID NO 60
<211> LENGTH: 114
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 60

Glu Val Gln Leu Val Glu Ser Gly Gly Gly Leu Val Gln Pro Gly Gly
1 5 10 15

Ser Leu Lys Leu Ser Cys Ala Ala Ser Gly Phe Ile Phe Ser Ser Tyr
20 25 30

Gly Met Ser Trp Val Arg Gln Ser Pro Asp Arg Arg Leu Glu Leu Val
35 40 45

Ala Ser Ile Asn Thr Phe Gly Asp Arg Thr Tyr Tyr Pro Asp Ser Val
50 55 60

Lys Gly Arg Phe Thr Ile Ser Arg Asp Asn Ala Lys Asn Thr Leu Tyr
65 70 75 80

Leu Gln Met Thr Ser Leu Lys Ser Glu Asp Thr Ala Ile Tyr Tyr Cys
85 90 95

Ala Arg Gly Thr Gly Thr Tyr Trp Gly Gln Gly Thr Thr Leu Thr Val
100 105 110

Ser Ser

<210> SEQ ID NO 61
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 61

```
Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Tyr Met Tyr Trp Val Lys Gln Arg Pro Gly Gln Gly Leu Glu Trp Ile
        35                  40                  45

Gly Glu Ile Asn Pro Ser Asn Gly Gly Thr Asn Phe Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Gly Gly Tyr Tyr Pro Phe Asp Tyr Trp Gly Gln Gly Thr Thr
            100                 105                 110

Leu Thr Val Ser Ser
        115
```

<210> SEQ ID NO 62
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 62

```
Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Phe Ser Gly Tyr Thr Ser Tyr Asn Pro Ser Leu
    50                  55                  60

Lys Ser Arg Ile Ser Val Thr Arg Asp Thr Ser Arg Asn Gln Phe Phe
65                  70                  75                  80

Leu Gln Leu Thr Ser Val Thr Thr Glu Asp Thr Ala Thr Tyr Tyr Cys
                85                  90                  95

Ala Arg Glu Val Asn Tyr Gly Asp Ser Tyr His Phe Asp Tyr Trp Gly
            100                 105                 110

Gln Gly Thr Ile Val Thr Val Ser Ser
        115                 120
```

<210> SEQ ID NO 63
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 63

Asp Ile Val Met Thr Gln Ala Ala Ser Ser Asn Pro Val Thr Leu Gly
1 5 10 15

Thr Ser Ala Ser Ile Ser Cys Arg Ser Ser Lys Ser Leu Arg His Thr
20 25 30

Lys Gly Ile Thr Phe Leu Tyr Trp Tyr Leu Gln Lys Pro Gly Gln Ser
35 40 45

Pro Gln Leu Leu Ile Tyr Gln Met Ser Asn Leu Ala Ser Gly Val Pro
50 55 60

Asp Arg Phe Ser Ser Ser Gly Ser Gly Thr Asp Phe Thr Leu Arg Ile
65 70 75 80

Ser Arg Val Glu Ala Glu Asp Leu Gly Val Tyr Tyr Cys Ala Gln Asn
85 90 95

Leu Glu Leu Pro Leu Thr Phe Gly Ala Gly Thr Lys Leu Glu Leu Lys
100 105 110

<210> SEQ ID NO 64
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 64

Asp Val Val Leu Thr Gln Thr Pro Leu Thr Leu Ser Val Thr Ile Gly
1 5 10 15

Gln Pro Ala Ser Ile Ser Cys Lys Ser Ser Gln Ser Leu Leu Asp Ser
20 25 30

Asp Gly Lys Thr Tyr Leu Asn Trp Leu Leu Gln Arg Pro Gly Gln Ser
35 40 45

Pro Lys Arg Leu Ile Tyr Leu Val Ser Lys Leu Asp Ser Gly Val Pro
50 55 60

Asp Arg Phe Thr Gly Ser Gly Ser Gly Thr Asp Phe Thr Leu Lys Ile
65 70 75 80

Ser Arg Val Glu Ala Glu Asp Leu Gly Val Tyr Tyr Cys Trp Gln Gly
85 90 95

Thr His Phe Pro Gln Thr Phe Gly Gly Gly Thr Lys Leu Glu Ile Lys
100 105 110

<210> SEQ ID NO 65
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

Asp Val Val Met Thr Gln Thr Pro Leu Thr Leu Ser Val Thr Ile Gly
1 5 10 15

Arg Pro Ala Ser Ile Ser Cys Lys Ser Ser Gln Ser Leu Leu Asp Ser
20 25 30

Asp Gly Lys Thr Tyr Leu Tyr Trp Leu Leu Gln Arg Pro Gly Gln Ser
35 40 45

Pro Lys Arg Leu Ile Tyr Leu Val Ser Glu Leu Asp Ser Gly Val Pro
50 55 60

Asp Arg Ile Thr Gly Ser Gly Ser Gly Thr Asp Phe Thr Leu Lys Ile
65 70 75 80

```
Ser Arg Val Glu Ala Glu Asp Leu Gly Val Tyr Tyr Cys Trp Gln Gly
                85                  90                  95

Thr His Ser Pro Tyr Thr Phe Gly Gly Gly Thr Lys Leu Glu Ile Lys
            100                 105                 110


<210> SEQ ID NO 66
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Leu Ala Leu Thr Gln Ser Ser Ser Ala Ser Phe Ser Leu Gly Ala
1               5                   10                  15

Ser Ala Lys Leu Thr Cys Thr Leu Ser Ser Gln His Arg Thr Tyr Thr
            20                  25                  30

Ile Glu Trp Tyr Gln Gln Gln Ser Leu Lys Pro Pro Lys Tyr Val Met
        35                  40                  45

Glu Val Lys Lys Asp Gly Ser His Ser Thr Gly His Gly Ile Pro Asp
    50                  55                  60

Arg Phe Ser Gly Ser Ser Ser Gly Ala Asp Arg Tyr Leu Ser Ile Ser
65                  70                  75                  80

Asn Ile Gln Pro Glu Asp Glu Ala Ile Tyr Ile Cys Gly Val Gly Asp
                85                  90                  95

Ala Ile Lys Gly Gln Ser Val Phe Val Phe Gly Gly Gly Thr Lys Val
            100                 105                 110

Thr Val Leu
        115


<210> SEQ ID NO 67
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(351)

<400> SEQUENCE: 67

gaa gtg cag ctg gtg gag tct ggg gga ggc tta gtg aag cct gga ggg       48
Glu Val Gln Leu Val Glu Ser Gly Gly Gly Leu Val Lys Pro Gly Gly
1               5                   10                  15

tcc ctg aaa ctc tcc tgt gca gcc tct gga ttc act ttc act acc tat       96
Ser Leu Lys Leu Ser Cys Ala Ala Ser Gly Phe Thr Phe Thr Thr Tyr
            20                  25                  30

gcc atg tct tgg gtt cgc cag act ccg gag aag agg ctg gag tgg gtc      144
Ala Met Ser Trp Val Arg Gln Thr Pro Glu Lys Arg Leu Glu Trp Val
        35                  40                  45

gca acc att agt agt ggt ggt act tac acc tac tat cca gac agt gtg      192
Ala Thr Ile Ser Ser Gly Gly Thr Tyr Thr Tyr Tyr Pro Asp Ser Val
    50                  55                  60

aag ggt cga ttc acc atc tcc aga gac aat gcc aag aac gcc cta tac      240
Lys Gly Arg Phe Thr Ile Ser Arg Asp Asn Ala Lys Asn Ala Leu Tyr
65                  70                  75                  80

ctg caa atg agc agt ctg agg tct gag gac acg gcc atg tat tac tgt      288
Leu Gln Met Ser Ser Leu Arg Ser Glu Asp Thr Ala Met Tyr Tyr Cys
                85                  90                  95
```

```
gca aca cag ggg aat tac tct ttg gac ttc tgg ggc caa ggc acc tct      336
Ala Thr Gln Gly Asn Tyr Ser Leu Asp Phe Trp Gly Gln Gly Thr Ser
            100                 105                 110

ctc aca gtc tcc tca                                                  351
Leu Thr Val Ser Ser
        115


<210> SEQ ID NO 68
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(342)

<400> SEQUENCE: 68

gag gtg cag ctg gtg gag tct ggg gga ggc ttg gtg cag cct gga ggg       48
Glu Val Gln Leu Val Glu Ser Gly Gly Gly Leu Val Gln Pro Gly Gly
1               5                   10                  15

tcc ctg aaa ctc tcc tgt gca gcc tct gga ttc att ttc agt agc tat       96
Ser Leu Lys Leu Ser Cys Ala Ala Ser Gly Phe Ile Phe Ser Ser Tyr
            20                  25                  30

ggc atg tct tgg gtt cgc cag tct cca gac agg agg ctg gag ttg gtc      144
Gly Met Ser Trp Val Arg Gln Ser Pro Asp Arg Arg Leu Glu Leu Val
        35                  40                  45

gca agt att aat act ttt ggt gat aga acc tat tat cca gac agt gtg      192
Ala Ser Ile Asn Thr Phe Gly Asp Arg Thr Tyr Tyr Pro Asp Ser Val
    50                  55                  60

aag ggc cga ttc acc atc tcc aga gac aat gcc aag aac acc ctg tac      240
Lys Gly Arg Phe Thr Ile Ser Arg Asp Asn Ala Lys Asn Thr Leu Tyr
65                  70                  75                  80

ctg caa atg acc agt ctg aag tct gag gac aca gcc att tat tac tgt      288
Leu Gln Met Thr Ser Leu Lys Ser Glu Asp Thr Ala Ile Tyr Tyr Cys
                85                  90                  95

gca aga ggg acc gga acc tac tgg ggc caa ggc acc act ctc aca gtc      336
Ala Arg Gly Thr Gly Thr Tyr Trp Gly Gln Gly Thr Thr Leu Thr Val
            100                 105                 110

tcc tca                                                              342
Ser Ser


<210> SEQ ID NO 69
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(351)

<400> SEQUENCE: 69

cag gtc caa ctg cag cag tct ggg gct gaa ctg gtg aag cct ggg gct       48
Gln Val Gln Leu Gln Gln Ser Gly Ala Glu Leu Val Lys Pro Gly Ala
1               5                   10                  15

tca gtg aag ttg tcc tgc aag gct tct ggc tac acc ttc acc agc tac       96
Ser Val Lys Leu Ser Cys Lys Ala Ser Gly Tyr Thr Phe Thr Ser Tyr
            20                  25                  30

tat atg tac tgg gtg aag cag agg cct gga caa ggc ctt gag tgg att      144
Tyr Met Tyr Trp Val Lys Gln Arg Pro Gly Gln Gly Leu Glu Trp Ile
        35                  40                  45
```

```
gga gag att aat cct agc aat ggt ggt act aac ttc aat gag aag ttc      192
Gly Glu Ile Asn Pro Ser Asn Gly Gly Thr Asn Phe Asn Glu Lys Phe
    50                  55                  60

aag agc aag gcc aca ctg act gta gac aaa tcc tcc agc aca gca tac      240
Lys Ser Lys Ala Thr Leu Thr Val Asp Lys Ser Ser Ser Thr Ala Tyr
65                  70                  75                  80

atg caa ctc agc agc ctg aca tct gag gac tct gcg gtc tat tac tgt      288
Met Gln Leu Ser Ser Leu Thr Ser Glu Asp Ser Ala Val Tyr Tyr Cys
                85                  90                  95

aca aga ggc ggt tac tac ccc ttt gac tac tgg ggc caa ggc acc act      336
Thr Arg Gly Gly Tyr Tyr Pro Phe Asp Tyr Trp Gly Gln Gly Thr Thr
            100                 105                 110

ctc aca gtc tcc tca                                                  351
Leu Thr Val Ser Ser
        115


<210> SEQ ID NO 70
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(363)

<400> SEQUENCE: 70

gat gtg cag ctt cag gag tcg gga cct ggc ctg gtg aaa cct tct cag       48
Asp Val Gln Leu Gln Glu Ser Gly Pro Gly Leu Val Lys Pro Ser Gln
1               5                   10                  15

tct ctg tcc ctc aca tgc act gtc act ggc tac tca atc acc agt gat       96
Ser Leu Ser Leu Thr Cys Thr Val Thr Gly Tyr Ser Ile Thr Ser Asp
            20                  25                  30

tat gcc tgg aat tgg atc cgg cag ttt cca gga aac aaa ctg gag tgg      144
Tyr Ala Trp Asn Trp Ile Arg Gln Phe Pro Gly Asn Lys Leu Glu Trp
        35                  40                  45

atg ggc tac ata agc ttc agt ggt tac act agt tac aac cca tct ctc      192
Met Gly Tyr Ile Ser Phe Ser Gly Tyr Thr Ser Tyr Asn Pro Ser Leu
    50                  55                  60

aaa agt cga atc tct gtc act cgg gac aca tcc agg aac caa ttc ttc      240
Lys Ser Arg Ile Ser Val Thr Arg Asp Thr Ser Arg Asn Gln Phe Phe
65                  70                  75                  80

ctc cag ttg act tct gtg act act gag gac aca gcc aca tat tac tgt      288
Leu Gln Leu Thr Ser Val Thr Thr Glu Asp Thr Ala Thr Tyr Tyr Cys
                85                  90                  95

gca aga gag gtc aac tat ggg gac tcc tac cac ttt gac tac tgg ggc      336
Ala Arg Glu Val Asn Tyr Gly Asp Ser Tyr His Phe Asp Tyr Trp Gly
            100                 105                 110

caa ggc acc att gtc aca gtc tcc tca                                  363
Gln Gly Thr Ile Val Thr Val Ser Ser
        115                 120


<210> SEQ ID NO 71
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)
```

<400> SEQUENCE: 71

```
gac att gtg atg acg cag gct gca tcc tct aat cca gtc act ctt gga       48
Asp Ile Val Met Thr Gln Ala Ala Ser Ser Asn Pro Val Thr Leu Gly
1               5                   10                  15

aca tcc gct tcc atc tcc tgc agg tct agt aag agt ctc cga cat act       96
Thr Ser Ala Ser Ile Ser Cys Arg Ser Ser Lys Ser Leu Arg His Thr
            20                  25                  30

aaa ggc atc act ttt ttg tat tgg tat ctg cag aag cca ggc cag tct      144
Lys Gly Ile Thr Phe Leu Tyr Trp Tyr Leu Gln Lys Pro Gly Gln Ser
        35                  40                  45

cct cag ctc ctg att tat cag atg tcc aac ctt gcc tca gga gtc cca      192
Pro Gln Leu Leu Ile Tyr Gln Met Ser Asn Leu Ala Ser Gly Val Pro
    50                  55                  60

gac agg ttc agt agc agt ggg tca gga act gat ttc aca ctg aga atc      240
Asp Arg Phe Ser Ser Ser Gly Ser Gly Thr Asp Phe Thr Leu Arg Ile
65                  70                  75                  80

agc aga gtg gag gct gag gat ttg ggt gtt tat tac tgt gct caa aat      288
Ser Arg Val Glu Ala Glu Asp Leu Gly Val Tyr Tyr Cys Ala Gln Asn
                85                  90                  95

cta gaa ctt ccg ctc acg ttc ggt gct ggg acc aag ctg gag ctg aaa      336
Leu Glu Leu Pro Leu Thr Phe Gly Ala Gly Thr Lys Leu Glu Leu Lys
            100                 105                 110
```

<210> SEQ ID NO 72
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(336)

<400> SEQUENCE: 72

```
gat gtt gtg ctg acc cag act cca ctc act ttg tcg gtt acc att gga       48
Asp Val Val Leu Thr Gln Thr Pro Leu Thr Leu Ser Val Thr Ile Gly
1               5                   10                  15

caa cca gcc tcc atc tcc tgc aag tca agt cag agc ctc tta gat agt       96
Gln Pro Ala Ser Ile Ser Cys Lys Ser Ser Gln Ser Leu Leu Asp Ser
            20                  25                  30

gat gga aag aca tat ttg aat tgg ttg tta cag agg cca ggc cag tct      144
Asp Gly Lys Thr Tyr Leu Asn Trp Leu Leu Gln Arg Pro Gly Gln Ser
        35                  40                  45

cca aag cgc cta atc tat ctg gtg tct aaa ctg gac tct gga gtc cct      192
Pro Lys Arg Leu Ile Tyr Leu Val Ser Lys Leu Asp Ser Gly Val Pro
    50                  55                  60

gac agg ttc act ggc agt gga tca ggg aca gat ttc aca ctg aaa atc      240
Asp Arg Phe Thr Gly Ser Gly Ser Gly Thr Asp Phe Thr Leu Lys Ile
65                  70                  75                  80

agc aga gtg gag gct gag gat ttg gga gtt tat tat tgc tgg caa ggt      288
Ser Arg Val Glu Ala Glu Asp Leu Gly Val Tyr Tyr Cys Trp Gln Gly
                85                  90                  95

aca cat ttt cct cag acg ttc ggt gga ggc acc aag ctg gaa atc aaa      336
Thr His Phe Pro Gln Thr Phe Gly Gly Gly Thr Lys Leu Glu Ile Lys
            100                 105                 110
```

<210> SEQ ID NO 73
<211> LENGTH: 336
<212> TYPE: DNA
<213> ORGANISM: Artificial Sequence
<220> FEATURE:
<223> OTHER INFORMATION: Description of Artificial Sequence: Synthetic

```
      polynucleotide
<220> FEATURE:
<221> NAME/KEY: CDS
<222> LOCATION: (1)..(336)

<400> SEQUENCE: 73

gat gtt gtg atg acc cag act cca ctc act ttg tcg gtt acc att ggg       48
Asp Val Val Met Thr Gln Thr Pro Leu Thr Leu Ser Val Thr Ile Gly
1               5                   10                  15

cgc cca gcc tcc atc tct tgc aag tca agt cag agc ctc tta gac agt       96
Arg Pro Ala Ser Ile Ser Cys Lys Ser Ser Gln Ser Leu Leu Asp Ser
            20                  25                  30

gat gga aag aca tat ttg tat tgg ttg tta cag agg cca ggc cag tct      144
Asp Gly Lys Thr Tyr Leu Tyr Trp Leu Leu Gln Arg Pro Gly Gln Ser
        35                  40                  45

cca aag cgc cta atc tat ctg gtg tct gag ctg gac tct gga gtc cct      192
Pro Lys Arg Leu Ile Tyr Leu Val Ser Glu Leu Asp Ser Gly Val Pro
    50                  55                  60

gac agg atc act ggc agt ggg tcg ggg aca gat ttc aca ctg aag atc      240
Asp Arg Ile Thr Gly Ser Gly Ser Gly Thr Asp Phe Thr Leu Lys Ile
65                  70                  75                  80

agc aga gtg gag gct gag gat ttg gga gtt tat tat tgc tgg caa gga      288
Ser Arg Val Glu Ala Glu Asp Leu Gly Val Tyr Tyr Cys Trp Gln Gly
                85                  90                  95

aca cat tct ccg tac acg ttc gga ggg ggg acc aag ctg gaa ata aaa      336
Thr His Ser Pro Tyr Thr Phe Gly Gly Gly Thr Lys Leu Glu Ile Lys
            100                 105                 110


<210> SEQ ID NO 74
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(345)

<400> SEQUENCE: 74

caa ctt gcg ctc act cag tca tct tca gcc tct ttc tcc ctg gga gcc       48
Gln Leu Ala Leu Thr Gln Ser Ser Ser Ala Ser Phe Ser Leu Gly Ala
1               5                   10                  15

tca gca aaa cta acg tgc act ttg agt agt caa cac aga acg tac acc       96
Ser Ala Lys Leu Thr Cys Thr Leu Ser Ser Gln His Arg Thr Tyr Thr
            20                  25                  30

att gaa tgg tat cag caa cag tca ctc aag cct cct aag tat gtg atg      144
Ile Glu Trp Tyr Gln Gln Gln Ser Leu Lys Pro Pro Lys Tyr Val Met
        35                  40                  45

gag gtt aag aaa gat gga agc cac agc aca ggt cat ggg att cct gat      192
Glu Val Lys Lys Asp Gly Ser His Ser Thr Gly His Gly Ile Pro Asp
    50                  55                  60

cgc ttc tct gga tcc agt tct ggt gct gat cgc tac ctc agc att tcc      240
Arg Phe Ser Gly Ser Ser Ser Gly Ala Asp Arg Tyr Leu Ser Ile Ser
65                  70                  75                  80

aac atc cag cct gaa gat gaa gca ata tac atc tgt ggt gtg ggt gat      288
Asn Ile Gln Pro Glu Asp Glu Ala Ile Tyr Ile Cys Gly Val Gly Asp
                85                  90                  95

gca att aag gga caa tct gtg ttt gtt ttc ggc ggt ggc acc aag gtc      336
Ala Ile Lys Gly Gln Ser Val Phe Val Phe Gly Gly Gly Thr Lys Val
            100                 105                 110

act gtc cta                                                          345
Thr Val Leu
```

115

<210> SEQ ID NO 75
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 75

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
        35                  40                  45

Ser Ser Ile Ser Ser Gly Gly Thr Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
        115
```

<210> SEQ ID NO 76
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 76

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110
```

<210> SEQ ID NO 77
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 77

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Thr Thr Tyr
20 25 30

Ala Met Asn Trp Val Arg Gln Ala Pro Gly Lys Gly Leu Glu Trp Val
35 40 45

Ser Ser Ile Ser Ser Gly Gly Thr Tyr Thr Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Thr Gln Gly Asn Tyr Ser Leu Asp Phe Trp Gly Gln Gly Thr Thr
100 105 110

Val Thr Val Ser Ser
115

<210> SEQ ID NO 78
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 78

Asp Ile Val Met Thr Gln Ser Pro Leu Ser Leu Pro Val Thr Pro Gly
1 5 10 15

Glu Pro Ala Ser Ile Ser Cys Arg Ser Ser Lys Ser Leu Arg His Thr
20 25 30

Lys Gly Ile Thr Phe Leu Asp Trp Tyr Leu Gln Lys Pro Gly Gln Ser
35 40 45

Pro Gln Leu Leu Ile Tyr Gln Met Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Ala Gln Asn
85 90 95

Leu Glu Leu Pro Leu Thr Phe Gly Gly Gly Thr Lys Val Glu Ile Lys
100 105 110

<210> SEQ ID NO 79
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 79

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Thr Thr Tyr
20 25 30

Ala Met Ser Trp Val Arg Gln Ala Pro Gly Lys Gly Leu Glu Trp Val
35 40 45

Ser Thr Ile Ser Ser Gly Gly Thr Tyr Thr Tyr Tyr Ala Asp Ser Val
50 55 60

```
Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
        115


<210> SEQ ID NO 80
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Gly Met Ser Trp Val Arg Gln Ala Pro Gly Lys Gly Leu Glu Trp Val
        35                  40                  45

Ala Asn Ile Asn Thr Phe Gly Asp Arg Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Thr Tyr Trp Gly Gln Gly Thr Leu Val Thr Val
            100                 105                 110

Ser Ser


<210> SEQ ID NO 81
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gly Gly Thr Lys Val Glu Ile Lys
            100                 105                 110
```

<210> SEQ ID NO 82
<211> LENGTH: 114
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 82

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ile Phe Ser Ser Tyr
20 25 30

Gly Met Ser Trp Val Arg Gln Ala Pro Gly Lys Gly Leu Glu Trp Val
35 40 45

Ala Ser Ile Asn Thr Phe Gly Asp Arg Thr Tyr Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Gly Thr Gly Thr Tyr Trp Gly Gln Gly Thr Leu Val Thr Val
100 105 110

Ser Ser

<210> SEQ ID NO 83
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 83

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Leu Asp Ser
20 25 30

Asp Gly Lys Thr Tyr Leu Asn Trp Phe Gln Gln Arg Pro Gly Gln Ser
35 40 45

Pro Arg Arg Leu Ile Tyr Leu Val Ser Lys Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Trp Gln Gly
85 90 95

Thr His Phe Pro Gln Thr Phe Gly Gly Gly Thr Lys Val Glu Ile Lys
100 105 110

<210> SEQ ID NO 84
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 84

Gln Val Gln Leu Val Gln Ser Gly Ala Glu Val Lys Lys Pro Gly Ala
1 5 10 15

```
Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Ile Ile Asn Pro Ser Asn Gly Gly Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115


<210> SEQ ID NO 85
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110


<210> SEQ ID NO 86
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Asn Gly Gly Thr Ser Tyr Ala Gln Lys Phe
    50                  55                  60

Gln Gly Arg Val Thr Met Thr Arg Asp Thr Ser Thr Ser Thr Val Tyr
65                  70                  75                  80
```

```
Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115


<210> SEQ ID NO 87
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110


<210> SEQ ID NO 88
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Glu Ile Asn Pro Ser Asn Gly Gly Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115


<210> SEQ ID NO 89
```

<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 89

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Leu Asp Ser
20 25 30

Asp Gly Lys Thr Tyr Leu Tyr Trp Phe Gln Gln Arg Pro Gly Gln Ser
35 40 45

Pro Arg Arg Leu Ile Tyr Leu Val Ser Glu Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Trp Gln Gly
85 90 95

Thr His Ser Pro Tyr Thr Phe Gly Gln Gly Thr Lys Leu Glu Ile Lys
100 105 110

<210> SEQ ID NO 90
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 90

Gln Val Gln Leu Gln Glu Ser Gly Pro Gly Leu Val Lys Pro Ser Gln
1 5 10 15

Thr Leu Ser Leu Thr Cys Thr Val Ser Gly Tyr Ser Ile Thr Ser Asp
20 25 30

Tyr Ala Trp Asn Trp Ile Arg Gln His Pro Gly Lys Gly Leu Glu Trp
35 40 45

Ile Gly Tyr Ile Ser Phe Ser Gly Tyr Thr Tyr Tyr Asn Pro Ser Leu
50 55 60

Lys Ser Arg Val Thr Ile Ser Val Asp Thr Ser Lys Asn Gln Phe Ser
65 70 75 80

Leu Lys Leu Ser Ser Val Thr Ala Ala Asp Thr Ala Val Tyr Tyr Cys
85 90 95

Ala Arg Glu Val Asn Tyr Gly Asp Ser Tyr His Phe Asp Tyr Trp Gly
100 105 110

Gln Gly Thr Leu Val Thr Val Ser Ser
115 120

<210> SEQ ID NO 91
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 91

Gln Leu Val Leu Thr Gln Ser Pro Ser Ala Ser Ala Ser Leu Gly Ala
1 5 10 15

```
Ser Val Lys Leu Thr Cys Thr Leu Ser Ser Gln His Arg Thr Tyr Thr
            20                  25                  30

Ile Glu Trp His Gln Gln Gln Pro Glu Lys Gly Pro Arg Tyr Leu Met
        35                  40                  45

Lys Val Lys Lys Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110

Glu Ile Lys
        115


<210> SEQ ID NO 92
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Ser Trp Ile Arg Gln His Pro Gly Lys Gly Leu Glu Trp
        35                  40                  45

Ile Gly Tyr Ile Ser Phe Ser Gly Tyr Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120


<210> SEQ ID NO 93
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Ala Trp His Gln Gln Gln Pro Glu Lys Gly Pro Arg Tyr Leu Met
        35                  40                  45

Lys Val Lys Lys Asp Gly Ser His Ser Lys Gly Asp Gly Ile Pro Asp
    50                  55                  60
```

```
Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110

Glu Ile Lys
        115
```

<210> SEQ ID NO 94
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 94

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Phe Ser Gly Tyr Thr Ser Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120
```

<210> SEQ ID NO 95
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 95

```
Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Glu Trp His Gln Gln Gln Pro Glu Lys Gly Pro Arg Tyr Leu Met
        35                  40                  45

Glu Val Lys Lys Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110
```

```
Glu Ile Lys
        115


<210> SEQ ID NO 96
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Ahx

<400> SEQUENCE: 96

Cys Xaa Xaa Gln Gly Pro Trp Leu Glu Glu Glu Glu Glu Ala Tyr Gly
1               5                   10                  15

Trp Met Asp Phe Gly Arg Arg Ser Ala Glu Asp Glu Asn
            20                  25


<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Ahx

<400> SEQUENCE: 97

Cys Xaa Xaa Phe Gly Arg Arg Ser Ala Glu Asp Glu Asn
1               5                   10


<210> SEQ ID NO 98
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(12)
<223> OTHER INFORMATION: Ahx

<400> SEQUENCE: 98

Phe Gly Arg Arg Ser Ala Glu Asp Glu Asn Xaa Xaa Cys
1               5                   10


<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Gly Gly Gly Ser Gly Gly Gly Gly Ser Gly Gly Gly Gly Ser
1               5                   10                  15


<210> SEQ ID NO 100
<211> LENGTH: 101
<212> TYPE: PRT
<213> ORGANISM: Homo sapiens
```

```
<220> FEATURE:
<221> NAME/KEY: SIGNAL
<222> LOCATION: (1)..(21)
<220> FEATURE:
<221> NAME/KEY: mat_peptide
<222> LOCATION: (22)..(101)

<400> SEQUENCE: 100

Met Gln Arg Leu Cys Val Tyr Val Leu Ile Phe Ala Leu Ala Leu Ala
    -20                 -15                 -10

Ala Phe Ser Glu Ala Ser Trp Lys Pro Arg Ser Gln Gln Pro Asp Ala
-5              -1  1               5                   10

Pro Leu Gly Thr Gly Ala Asn Arg Asp Leu Glu Leu Pro Trp Leu Glu
            15                  20                  25

Gln Gln Gly Pro Ala Ser His His Arg Arg Gln Leu Gly Pro Gln Gly
        30                  35                  40

Pro Pro His Leu Val Ala Asp Pro Ser Lys Lys Gln Gly Pro Trp Leu
    45                  50                  55

Glu Glu Glu Glu Glu Ala Tyr Gly Trp Met Asp Phe Gly Arg Arg Ser
60                  65                  70                  75

Ala Glu Asp Glu Asn
                80


<210> SEQ ID NO 101
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term NH2

<400> SEQUENCE: 101

Gln Leu Gly Pro Gln Gly Pro Pro His Leu Val Ala Asp Pro Ser Lys
1               5                   10                  15

Lys Glu Gly Pro Trp Leu Glu Glu Glu Glu Glu Ala Tyr Gly Trp Met
            20                  25                  30

Asp Phe


<210> SEQ ID NO 102
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Leu Gly Pro Gln Gly Pro Pro His Leu Val Ala Asp Pro Ser Lys
1               5                   10                  15

Lys Glu Gly Pro Trp Leu Glu Glu Glu Glu Glu Ala Tyr Gly Trp Met
            20                  25                  30

Asp Phe Gly
        35


<210> SEQ ID NO 103
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

-continued

```
<220> FEATURE:
<223> OTHER INFORMATION: C-term NH2

<400> SEQUENCE: 103

Glu Gly Pro Trp Leu Glu Glu Glu Glu Glu Ala Tyr Gly Trp Met Asp
1               5                   10                  15

Phe


<210> SEQ ID NO 104
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Glu Gly Pro Trp Leu Glu Glu Glu Glu Glu Ala Tyr Gly Trp Met Asp
1               5                   10                  15

Phe Gly


<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ser Ala Glu Asp Glu Asn
1               5
```